United States Patent
Armitage et al.

(10) Patent No.: US 8,679,487 B2
(45) Date of Patent: *Mar. 25, 2014

(54) ANTI-INTERLEUKIN-4 RECEPTOR ANTIBODIES

(75) Inventors: Richard J. Armitage, Bainbridge Island, WA (US); Jose Carlos Escobar, Sammamish, WA (US); Arvia E. Morris, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 336 days.

This patent is subject to a terminal disclaimer.

(21) Appl. No.: 12/829,231

(22) Filed: Jul. 1, 2010

(65) Prior Publication Data

US 2011/0002913 A1 Jan. 6, 2011

Related U.S. Application Data

(60) Continuation of application No. 12/291,702, filed on Nov. 13, 2008, now abandoned, which is a continuation of application No. 11/588,696, filed on Oct. 27, 2006, now Pat. No. 7,465,450, which is a division of application No. 10/324,493, filed on Dec. 19, 2002, now Pat. No. 7,186,809, which is a continuation of application No. 09/847,816, filed on May 1, 2001, now abandoned.

(51) Int. Cl.
*C07K 16/28* (2006.01)
*A61K 39/395* (2006.01)

(52) U.S. Cl.
USPC .......... 424/130.1; 530/387.1; 530/387.3; 530/388.22; 530/389.1; 530/389.2; 424/135.1

(58) Field of Classification Search
None
See application file for complete search history.

(56) References Cited

U.S. PATENT DOCUMENTS

| | | | |
|---|---|---|---|
| 5,717,072 | A | 2/1998 | Mosley et al. |
| 6,716,587 | B2 | 4/2004 | Mosley et al. |
| 2002/0076409 | A1* | 6/2002 | March et al. .......... 514/12 |

FOREIGN PATENT DOCUMENTS

| | | |
|---|---|---|
| EP | 0 604 693 | 7/1994 |
| WO | WO 90/05183 | 5/1990 |
| WO | WO 91/09059 | 6/1991 |
| WO | WO 94 21282 | 9/1994 |
| WO | WO 96/33735 | 10/1996 |
| WO | WO 96/34096 | 10/1996 |
| WO | WO 00/18932 | 4/2000 |
| WO | WO 01/92340 | 12/2001 |

OTHER PUBLICATIONS

Beckmann et al, Journal of Immunology, 1990, vol. 144, No. 11, pp. 4212-4217.*
Aya Jakobovits, Expert Opinion on Investigational Drugs, 1998, vol. 7; No. 4; pp. 607-614.*
Tony et al. Eur. J. Biochem, 2005, vol. 225, pp. 659-665.*
Hultgren O et al. "*Staphylococcus aureus*-induced septic arthritis and septic death is decreased in IL-4 -eficient mice: role of IL-4 as promoter for bacterial growth." *J. Immunol* 1998:160(10):5082-5087, May 1998.
Holt et al. "Domain antibodies: proteins for therapy," *Trends in Biotechnology*, 21(11):484-490, Nov. 2003.
Zurawski S. et al., "The primary binding subunit of the human interleukin-4 receptor is also a component of the interleukin-13 receptor," *J. Biol Chem* 270(23):13869-13878, Jun. 9, 1995.
Database EPOP: Accession No. AX365126.1, Feb. 15, 2002.
Related International Search Report for PCT/US01/17094, Feb. 2002.
Willis-Karp et al. Science, vol. 282, pp. 2258-2261, Dec. 18, 1998.
Paul et al., Fundamental Immunology, $3^{rd}$ Edition, 1993, pp. 292-295.
Casset et al., Biochemical and Biophysical Research Communications, 2003, vol. 307, pp. 198-205.
Munitz et al., PNAS, May 2008, vol. 105, No. 20, pp. 7240-7245.
Product Data Sheet for R&D Systems Catalog No. MAB230 (Rev. Jan. 2, 2008) (http://www.rndsystems.com/pdf/mab230.pdf).
Kitamura et al., "Establishment and Characterization of a Unique Human Cell Line That Proliferates Dependently on GM-CSF, IL-3, or Erythropoietin," Journal of Cellular Physiology, 1989, 140:323-334.
Rudikoff et al. "Single amino acid substitution altering antigen-binding specificty", Proc. Natl. Acad. Sci. USA, 1982, vol. 79: pp. 1979-1983.
Schnyder et al. "Interleukin-4 (IL-4) and IL-13 Bind to a Shared Heterodimeric Complex on Endothelial Cells Mediating Vascular Cell Adhesion Molecule-1 Induction in the Absence of the Common y Chain", Blood, 1996, vol. 87, No. 10: pp. 4288-4295.

* cited by examiner

*Primary Examiner* — Bridget E Bunner
*Assistant Examiner* — Fozia Hamud
(74) *Attorney, Agent, or Firm* — Nathan A. Machin

(57) ABSTRACT

Methods for treating medical conditions induced by interleukin-4 involve administering an IL-4 antagonist to a patient afflicted with such a condition. Suitable IL-4 antagonists include, but are not limited to, IL-4 receptors (such as a soluble human IL-4 receptor), antibodies that bind IL-4, antibodies that bind IL-4R, IL-4 muteins that bind to IL-4R but do not induce a biological response, molecules that inhibit IL-4-induced signal transduction, and other compounds that inhibit a biological effect that results from the binding of IL-4 to a cell surface IL-4R. Particular antibodies provided herein include human monoclonal antibodies generated by procedures involving immunization of transgenic mice. Such human antibodies may be raised against human IL-4 receptor. Certain of the antibodies inhibit both IL-4-induced and IL-13-induced biological activities.

17 Claims, 6 Drawing Sheets

FIGURE 1A

```
ATG GGG TGG CTT TGC TCT GGG CTC CTG TTC CCT GTG AGC TGC CTG  -31
Met Gly Trp Leu Cys Ser Gly Leu Leu Phe Pro Val Ser Cys Leu  -11

GTC CTG CTG CAG GTG GCA AGC TCT GGG AAC ATG AAG GTC TTG CAG   15
Val Leu Leu Gln Val Ala Ser Ser Gly Asn Met Lys Val Leu Gln    5

GAG CCC ACC TGC GTC TCC GAC TAC ATG AGC ATC TCT ACT TGC GAG   60
Glu Pro Thr Cys Val Ser Asp Tyr Met Ser Ile Ser Thr Cys Glu   20

TGG AAG ATG AAT GGT CCC ACC AAT TGC AGC ACC GAG CTC CGC CTG  105
Trp Lys Met Asn Gly Pro Thr Asn Cys Ser Thr Glu Leu Arg Leu   35

TTG TAC CAG CTG GTT TTT CTG CTC TCC GAA GCC CAC ACG TGT ATC  150
Leu Tyr Gln Leu Val Phe Leu Leu Ser Glu Ala His Thr Cys Ile   50

CCT GAG AAC AAC GGA GGC GCG GGG TGC GTG TGC CAC CTG CTC ATG  195
Pro Glu Asn Asn Gly Gly Ala Gly Cys Val Cys His Leu Leu Met   65

GAT GAC GTG GTC AGT GCG GAT AAC TAT ACA CTG GAC CTG TGG GCT  240
Asp Asp Val Val Ser Ala Asp Asn Tyr Thr Leu Asp Leu Trp Ala   80

GGG CAG CAG CTG CTG TGG AAG GGC TCC TTC AAG CCC AGC GAG CAT  285
Gly Gln Gln Leu Leu Trp Lys Gly Ser Phe Lys Pro Ser Glu His   95

GTG AAA CCC AGG GCC CCA GGA AAC CTG ACA GTT CAC ACC AAT GTC  330
Val Lys Pro Arg Ala Pro Gly Asn Leu Thr Val His Thr Asn Val  110

TCC GAC ACT CTG CTG CTG ACC TGG AGC AAC CCG TAT CCC CCT GAC  375
Ser Asp Thr Leu Leu Leu Thr Trp Ser Asn Pro Tyr Pro Pro Asp  125

AAT TAC CTG TAT AAT CAT CTC ACC TAT GCA GTC AAC ATT TGG AGT  420
Asn Tyr Leu Tyr Asn His Leu Thr Tyr Ala Val Asn Ile Trp Ser  140

GAA AAC GAC CCG GCA GAT TTC AGA ATC TAT AAC GTG ACC TAC CTA  465
Glu Asn Asp Pro Ala Asp Phe Arg Ile Tyr Asn Val Thr Tyr Leu  155

GAA CCC TCC CTC CGC ATC GCA GCC AGC ACC CTG AAG TCT GGG ATT  510
Glu Pro Ser Leu Arg Ile Ala Ala Ser Thr Leu Lys Ser Gly Ile  170

TCC TAC AGG GCA CGG GTG AGG GCC TGG GCT CAG TGC TAT AAC ACC  555
Ser Tyr Arg Ala Arg Val Arg Ala Trp Ala Gln Cys Tyr Asn Thr  185

ACC TGG AGT GAG TGG AGC CCC AGC ACC AAG TGG CAC AAC TCC TAC  600
Thr Trp Ser Glu Trp Ser Pro Ser Thr Lys Trp His Asn Ser Tyr  200

AGG GAG CCC TTC GAG CAG CAC CTC CTG CTG GGC GTC AGC GTT TCC  645
Arg Glu Pro Phe Glu Gln His Leu Leu Leu Gly Val Ser Val Ser  215

TGC ATT GTC ATC CTG GCC GTC TGC CTG TTG TGC TAT GTC AGC ATC  690
Cys Ile Val Ile Leu Ala Val Cys Leu Leu Cys Tyr Val Ser Ile  230

ACC AAG ATT AAG AAA GAA TGG TGG GAT CAG ATT CCC AAC CCA GCC  735
Thr Lys Ile Lys Lys Glu Trp Trp Asp Gln Ile Pro Asn Pro Ala  245
```

FIGURE 1B

```
CGC AGC CGC CTC GTG GCT ATA ATA ATC CAG GAT GCT CAG GGG TCA  780
Arg Ser Arg Leu Val Ala Ile Ile Ile Gln Asp Ala Gln Gly Ser  260

CAG TGG GAG AAG CGG TCC CGA GGC CAG GAA CCA GCC AAG TGC CCA  825
Gln Trp Glu Lys Arg Ser Arg Gly Gln Glu Pro Ala Lys Cys Pro  275

CAC TGG AAG AAT TGT CTT ACC AAG CTC TTG CCC TGT TTT CTG GAG  870
His Trp Lys Asn Cys Leu Thr Lys Leu Leu Pro Cys Phe Leu Glu  290

CAC AAC ATG AAA AGG GAT GAA GAT CCT CAC AAG GCT GCC AAA GAG  915
His Asn Met Lys Arg Asp Glu Asp Pro His Lys Ala Ala Lys Glu  305

ATG CCT TTC CAG GGC TCT GGA AAA TCA GCA TGG TGC CCA GTG GAG  960
Met Pro Phe Gln Gly Ser Gly Lys Ser Ala Trp Cys Pro Val Glu  320

ATC AGC AAG ACA GTC CTC TGG CCA GAG AGC ATC AGC GTG GTG CGA 1005
Ile Ser Lys Thr Val Leu Trp Pro Glu Ser Ile Ser Val Val Arg  335

TGT GTG GAG TTG TTT GAG GCC CCG GTG GAG TGT GAG GAG GAG GAG 1050
Cys Val Glu Leu Phe Glu Ala Pro Val Glu Cys Glu Glu Glu Glu  350

GAG GTA GAG GAA GAA AAA GGG AGC TTC TGT GCA TCG CCT GAG AGC 1095
Glu Val Glu Glu Glu Lys Gly Ser Phe Cys Ala Ser Pro Glu Ser  365

AGC AGG GAT GAC TTC CAG GAG GGA AGG GAG GGC ATT GTG GCC CGG 1140
Ser Arg Asp Asp Phe Gln Glu Gly Arg Glu Gly Ile Val Ala Arg  380

CTA ACA GAG AGC CTG TTC CTG GAC CTG CTC GGA GAG GAG AAT GGG 1185
Leu Thr Glu Ser Leu Phe Leu Asp Leu Leu Gly Glu Glu Asn Gly  395

GGC TTT TGC CAG CAG GAC ATG GGG GAG TCA TGC CTT CTT CCA CCT 1230
Gly Phe Cys Gln Gln Asp Met Gly Glu Ser Cys Leu Leu Pro Pro  410

TCG GGA AGT ACG AGT GCT CAC ATG CCC TGG GAT GAG TTC CCA AGT 1275
Ser Gly Ser Thr Ser Ala His Met Pro Trp Asp Glu Phe Pro Ser  425

GCA GGG CCC AAG GAG GCA CCT CCC TGG GGC AAG GAG CAG CCT CTC 1320
Ala Gly Pro Lys Glu Ala Pro Pro Trp Gly Lys Glu Gln Pro Leu  440

CAC CTG GAG CCA AGT CCT CCT GCC AGC CCG ACC AGT CCA GAC 1365
His Leu Glu Pro Ser Pro Pro Ala Ser Pro Thr Gln Ser Pro Asp  455

AAC CTG ACT TGC ACA GAG ACG CCC CTC GTC ATC GCA GGC AAC CCT 1410
Asn Leu Thr Cys Thr Glu Thr Pro Leu Val Ile Ala Gly Asn Pro  470

GCT TAC CGC AGC TTC AGC AAC TCC CTG AGC CAG TCA CCG TGT CCC 1455
Ala Tyr Arg Ser Phe Ser Asn Ser Leu Ser Gln Ser Pro Cys Pro  485

AGA GAG CTG GGT CCA GAC CCA CTG CTG GCC AGA CAC CTG GAG GAA 1500
Arg Glu Leu Gly Pro Asp Pro Leu Leu Ala Arg His Leu Glu Glu  500

GTA GAA CCC GAG ATG CCC TGT GTC CCC CAG CTC TCT GAG CCA ACC 1545
Val Glu Pro Glu Met Pro Cys Val Pro Gln Leu Ser Glu Pro Thr  515
```

FIGURE 1C

```
ACT GTG CCC CAA CCT GAG CCA GAA ACC TGG GAG CAG ATC CTC CGC  1590
Thr Val Pro Gln Pro Glu Pro Glu Thr Trp Glu Gln Ile Leu Arg   530

CGA AAT GTC CTC CAG CAT GGG GCA GCT GCA GCC CCC GTC TCG GCC  1635
Arg Asn Val Leu Gln His Gly Ala Ala Ala Ala Pro Val Ser Ala   545

CCC ACC AGT GGC TAT CAG GAG TTT GTA CAT GCG GTG GAG CAG GGT  1680
Pro Thr Ser Gly Tyr Gln Glu Phe Val His Ala Val Glu Gln Gly   560

GGC ACC CAG GCC AGT GCG GTG GTG GGC TTG GGT CCC CCA GGA GAG  1725
Gly Thr Gln Ala Ser Ala Val Val Gly Leu Gly Pro Pro Gly Glu   575

GCT GGT TAC AAG GCC TTC TCA AGC CTG CTT GCC AGC AGT GCT GTG  1770
Ala Gly Tyr Lys Ala Phe Ser Ser Leu Leu Ala Ser Ser Ala Val   590

TCC CCA GAG AAA TGT GGG TTT GGG GCT AGC AGT GGG GAA GAG GGG  1815
Ser Pro Glu Lys Cys Gly Phe Gly Ala Ser Ser Gly Glu Glu Gly   605

TAT AAG CCT TTC CAA GAC CTC ATT CCT GGC TGC CCT GGG GAC CCT  1860
Tyr Lys Pro Phe Gln Asp Leu Ile Pro Gly Cys Pro Gly Asp Pro   620

GCC CCA GTC CCT GTC CCC TTG TTC ACC TTT GGA CTG GAC AGG GAG  1905
Ala Pro Val Pro Val Pro Leu Phe Thr Phe Gly Leu Asp Arg Glu   635

CCA CCT CGC AGT CCG CAG AGC TCA CAT CTC CCA AGC AGC TCC CCA  1950
Pro Pro Arg Ser Pro Gln Ser Ser His Leu Pro Ser Ser Ser Pro   650

GAG CAC CTG GGT CTG GAG CCG GGG GAA AAG GTA GAG GAC ATG CCA  1995
Glu His Leu Gly Leu Glu Pro Gly Glu Lys Val Glu Asp Met Pro   665

AAG CCC CCA CTT CCC CAG GAG CAG GCC ACA GAC CCC CTT GTG GAC  2040
Lys Pro Pro Leu Pro Gln Glu Gln Ala Thr Asp Pro Leu Val Asp   680

AGC CTG GGC AGT GGC ATT GTC TAC TCA GCC CTT ACC TGC CAC CTG  2085
Ser Leu Gly Ser Gly Ile Val Tyr Ser Ala Leu Thr Cys His Leu   695

TGC GGC CAC CTG AAA CAG TGT CAT GGC CAG GAG GAT GGT GGC CAG  2130
Cys Gly His Leu Lys Gln Cys His Gly Gln Glu Asp Gly Gly Gln   710

ACC CCT GTC ATG GCC AGT CCT TGC TGT GGC TGC TGC TGT GGA GAC  2175
Thr Pro Val Met Ala Ser Pro Cys Cys Gly Cys Cys Cys Gly Asp   725

AGG TCC TCG CCC CCT ACA ACC CCC TTG AGG GCC CCA GAC CCC TCT  2220
Arg Ser Ser Pro Pro Thr Thr Pro Leu Arg Ala Pro Asp Pro Ser   740

CCA GGT GGG GTT CCA CTG GAG GCC AGT CTG TGT CCG GCC TCC CTG  2265
Pro Gly Gly Val Pro Leu Glu Ala Ser Leu Cys Pro Ala Ser Leu   755

GCA CCC TCG GGC ATC TCA GAG AAG AGT AAA TCC TCA TCA TCC TTC  2310
Ala Pro Ser Gly Ile Ser Glu Lys Ser Lys Ser Ser Ser Ser Phe   770

CAT CCT GCC CCT GGC AAT GCT CAG AGC TCA AGC AGA CCC CCA AAA  2355
His Pro Ala Pro Gly Asn Ala Gln Ser Ser Ser Gln Thr Pro Lys   785

ATC GTG AAC TTT GTC TCC GTG GGA CCC ACA TAC ATG AGG GTC TCT  2400
Ile Val Asn Phe Val Ser Val Gly Pro Thr Tyr Met Arg Val Ser   800
```

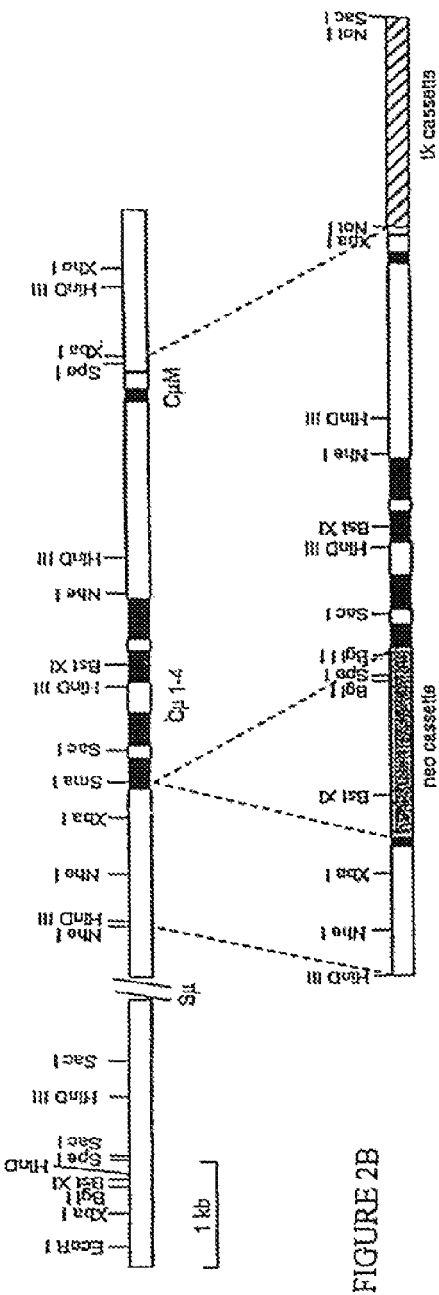
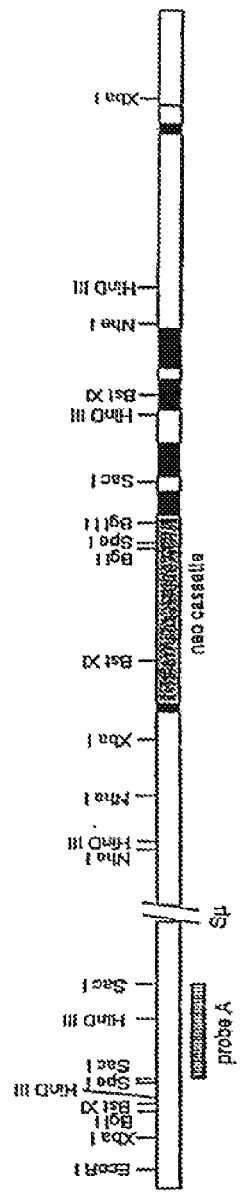
FIGURE 2A  FIGURE 2B  FIGURE 2C

FIGURE 3A

```
AATTAGCGGC CGCTGTCGAC AAGCTTCGAA TTCAGTATCG ATGTGGGGTA    50
CCTACTGTCC CGGGATTGCG GATCCGCGAT GATATCGTTG ATCCTCGAGT   100
GCGGCCGCAG TATGCAAAAA AAAGCCCGCT CATTAGGCGG GCTCTTGGCA   150
GAACATATCC ATCGCGTCCG CCATCTCCAG CAGCCGCACG CGGCGCATCT   200
CGGGCAGCGT TGGGTCCTGG CCACGGGTGC GCATGATCGT GCTCCTGTCG   250
TTGAGGACCC GGCTAGGCTG GCGGGGTTGC CTTACTGGTT AGCAGAATGA   300
ATCACCGATA CGCGAGCGAA CGTGAAGCGA CTGCTGCTGC AAAACGTCTG   350
CGACCTGAGC AACAACATGA ATGGTCTTCG GTTTCCGTGT TTCGTAAAGT   400
CTGGAAACGC GGAAGTCAGC GCCCTGCACC ATTATGTTCC GGATCTGCAT   450
CGCAGGATGC TGCTGGCTAC CCTGTGGAAC ACCTACATCT GTATTAACGA   500
AGCGCTGGCA TTGACCCTGA GTGATTTTTC TCTGGTCCCG CCGCATCCAT   550
ACCGCCAGTT GTTTACCCTC ACAACGTTCC AGTAACGGGG CATGTTCATC   600
ATCAGTAACC CGTATCGTGA GCATCCTCTC TCGTTTCATC GGTATCATTA   650
CCCCCATGAA CAGAAATTCC CCCTTACACG GAGGCATCAA GTGACCAAAC   700
AGGAAAAAAC CGCCCTTAAC ATGGCCCGCT TTATCAGAAG CCAGACATTA   750
ACGCTTCTGG AGAAACTCAA CGAGCTGGAC GCGGATGAAC AGGCAGACAT   800
CTGTGAATCG CTTCACGACC ACGCTGATGA GCTTTACCGC AGCTGCCTCG   850
CGCGTTTCGG TGATGACGGT GAAAACCTCT GACACATGCA GCTCCCGGAG   900
ACGGTCACAG CTTGTCTGTA AGCGGATGCC GGGAGCAGAC AAGCCCGTCA   950
GGGCGCGTCA GCGGGTGTTG GCGGGTGTCG GGGCGCAGCC ATGACCCAGT  1000
CACGTAGCGA TAGCGGAGTG TATACTGGCT TAACTATGCG GCATCAGAG   1050
AGATTGTACT GAGAGTGCAC CATATGCGGT GTGAAATACC GCACAGATGC  1100
GTAAGGAGAA AATACCGCAT CAGGCGCTCT TCCGCTTCCT CGCTCACTGA  1150
CTCGCTGCGC TCGGTCGTTC GGCTGCGGCG AGCGGTATCA GCTCACTCAA  1200
AGGCGGTAAT ACGGTTATCC ACAGAATCAG GGGATAACGC AGGAAAGAAC  1250
ATGTGAGCAA AAGGCCAGCA AAAGGCCAGG AACCGTAAAA AGGCCGCGTT  1300
GCTGGCGTTT TTCCATAGGC TCCGCCCCCC TGACGAGCAT CACAAAAATC  1350
GACGCTCAAG TCAGAGGTGG CGAAACCCGA CAGGACTATA AAGATACCAG  1400
GCGTTTCCCC CTGGAAGCTC CCTCGTGCGC TCTCCTGTTC CGACCCTGCC  1450
GCTTACCGGA TACCTGTCCG CCTTTCTCCC TTCGGGAAGC GTGGCGCTTT  1500
CTCATAGCTC ACGCTGTAGG TATCTCAGTT CGGTGTAGGT CGTTCGCTCC  1550
AAGCTGGGCT GTGTGCACGA ACCCCCCGTT CAGCCCGACC GCTGCGCCTT  1600
ATCCGGTAAC TATCGTCTTG AGTCCAACCC GGTAAGACAC GACTTATCGC  1650
CACTGGCAGC AGCCAGGCGC GCCTTGGCCT AAGAGGCCAC TGGTAACAGG  1700
ATTAGCAGAG CGAGGTATGT AGGCGGTGCT ACAGAGTTCT TGAAGTGGTG  1750
GCCTAACTAC GGCTACACTA GAAGGACAGT ATTTGGTATC TGCGCTCTGC  1800
TGAAGCCAGT TACCTTCGGA AAAAGAGTTG GTAGCTCTTG ATCCGGCAAA  1850
CAAACCACCG CTGGTAGCGG TGGTTTTTTT GTTTGCAAGC AGCAGATTAC  1900
GCGCAGAAAA AAAGGATCTC AAGAAGATCC TTTGATCTTT TCTACGGGGT  1950
CTGACGCTCA GTGGAACGAA AACTCACGTT AAGGGATTTT GGTCATGAGA  2000
TTATCAAAAA GGATCTTCAC CTAGATCCTT TTAAATTAAA AATGAAGTTT  2050
TAAATCAATC TAAAGTATAT ATGAGTAAAC TTGGTCTGAC AGTTACCAAT  2100
GCTTAATCAG TGAGGCACCT ATCTCAGCGA TCTGTCTATT TCGTTCATCC  2150
ATAGTTGCCT GACTCCCCGT CGTGTAGATA ACTACGATAC GGGAGGGCTT  2200
ACCATCTGGC CCCAGTGCTG CAATGATACC GCGAGACCCA CGCTCACCGG  2250
CTCCAGATTT ATCAGCAATA AACCAGCCAG CCGGAAGGGC CGAGCGCAGA  2300
AGTGGTCCTG CAACTTTATC CGCCTCCATC CAGTCTATTA ATTGTTGCCG  2350
GGAAGCTAGA GTAAGTAGTT CGCCAGTTAA TAGTTTGCGC AACGTTGTTG  2400
```

FIGURE 3B

```
CCATTGCTGC AGGCATCGTG GTGTCACGCT CGTCGTTTGG TATGGCTTCA 2450
TTCAGCTCCG GTTCCCAACG ATCAAGGCGA GTTACATGAT CCCCCATGTT 2500
GTGCAAAAAA GCGGTTAGCT CCTTCGGTCC TCCGATCGTT GTCAGAAGTA 2550
AGTTGGCCGC AGTGTTATCA CTCATGGTTA TGGCAGCACT GCATAATTCT 2600
CTTACTGTCA TGCCATCCGT AAGATGCTTT TCTGTGACTG GTGAGTACTC 2650
AACCAAGTCA TTCTGAGAAT AGTGTATGCG GCGACCGAGT TGCTCTTGCC 2700
CGGCGTCAAC ACGGGATAAT ACCGCGCCAC ATAGCAGAAC TTTAAAAGTG 2750
CTCATCATTG GAAAACGTTC TTCGGGGCGA AAACTCTCAA GGATCTTACC 2800
GCTGTTGAGA TCCAGTTCGA TGTAACCCAC TCGTGCACCC AACTGATCTT 2850
CAGCATCTTT TACTTTCACC AGCGTTTCTG GGTGAGCAAA AACAGGAAGG 2900
CAAAATGCCG CAAAAAAGGG AATAAGGGCG ACACGGAAAT GTTGAATACT 2950
CATACTCTTC CTTTTTCAAT ATTATTGAAG CATTTATCAG GGTTATTGTC 3000
TCATGAGCGG ATACATATTT GAATGTATTT AGAAAAATAA ACAAATAGGG 3050
GTTCCGCGCA CATTTCCCCG AAAAGTGCCA CCTGACGTCT AAGAAACCAT 3100
TATTATCATG ACATTAACCT ATAAAAATAG GCGTATCACG AGGCCCTTTC 3150
GTCTTCAAG                                             3159
```

ANTI-INTERLEUKIN-4 RECEPTOR ANTIBODIES

CROSS-REFERENCE TO RELATED APPLICATIONS

This application is a continuation of U.S. application Ser. No. 12/291,702, filed Nov. 13, 2008, now abandoned, which is a continuation of U.S. application Ser. No. 11/588,696, filed Oct. 27, 2006, now U.S. Pat. No. 7,465,450, which is a divisional of U.S. application Ser. No. 10/324,493, filed Dec. 19, 2002, now U.S. Pat. No. 7,186,809, which is a continuation of U.S. application Ser. No. 09/847,816, filed May 1, 2001, abandoned. The above-identified applications are incorporated herein by reference.

REFERENCE TO THE SEQUENCE LISTING

The present application is being filed along with a Sequence Listing in electronic format via EFS-Web. The Sequence Listing is provided as a text file entitled 3005USCNT3st25.txt, created Jun. 30, 2010, which is 55,527 bytes in size. The information in the electronic format of the Sequence Listing is incorporated herein by reference in its entirety.

BACKGROUND OF THE INVENTION

Interleukin-4 (IL-4), previously known as B cell stimulating factor, or BSF-1, was originally characterized by its ability to stimulate the proliferation of B cells in response to low concentrations of antibodies directed to surface immunoglobulin. IL-4 has been shown to possess a far broader spectrum of biological activities, including growth co-stimulation of T cells, mast cells, granulocytes, megakaryocytes, and erythrocytes. In addition, IL-4 stimulates the proliferation of several IL-2- and IL-3-dependent cell lines, induces the expression of class II major histocompatibility complex molecules on resting B cells, and enhances the secretion of IgE and IgG1 isotypes by stimulated B cells. IL-4 is associated with a TH2-type immune response, being one of the cytokines secreted by TH2 cells.

Murine and human IL-4 have been identified and characterized, including cloning of IL-4 cDNAs and determination of the nucleotide and encoded amino acid sequences. (See Yokota et al., *Proc. Natl. Acad. Sci. USA* 83:5894, 1986; Noma et al., *Nature* 319:640, 1986; Grabstein et al., *J. Exp. Med.* 163:1405, 1986; and U.S. Pat. No. 5,017,691.)

IL-4 binds to particular cell surface receptors, which results in transduction of a biological signal to cells such as various immune effector cells. IL-4 receptors are described, and DNA and amino acid sequence information presented, in Mosley et al., *Cell* 59:335-348, Oct. 20, 1989 (murine IL-4R); Idzerda et al., *J. Exp. Med.* 171:861-873, March 1990 (human IL-4R); and U.S. Pat. No. 5,599,905. The IL-4 receptor described in these publications is sometimes referred to as IL-4Rα.

Other proteins have been reported to be associated with IL-4Rα on some cell types, and to be components of multi-subunit IL-4 receptor complexes. One such subunit is IL-2Rγ, also known as IL-2Rγ$_c$. (See the discussion of IL-4R complexes in Sato et al., *Current Opinion in Cell Biology*, 6:174-179, 1994.) IL-4Rα has been reported to be a component of certain multi-subunit IL-13 receptor complexes (Zurawski et al., *J. Biol. Chem.* 270 (23), 13869, 1995; de Vries, *J. Allergy Clin. Immunol.* 102(2):165, August 1998; and Callard et al. *Immunology Today*, 17(3):108, March 1996).

IL-4 has been implicated in a number of disorders, examples of which are allergy and asthma. Studies of biological properties of IL-4 continue, in an effort to identify additional activities associated with this pleiotrophic cytokine, and to elucidate the role IL-4 may play in various biological processes and diseases.

SUMMARY OF THE INVENTION

The present invention provides methods for treating certain conditions induced by IL-4, comprising administering an IL-4 antagonist to a patient afflicted with such a condition. Also provided are compositions for use in such methods, comprising an effective amount of an IL-4 antagonist and a suitable diluent, excipient, or carrier. Endogenous IL-4 may be contacted with an IL-4 antagonist in alternative methods, such as those involving ex vivo procedures.

Among the conditions to be treated in accordance with the present invention are septic arthritis, dermatitis herpetiformis, chronic idiopathic urticaria, ulcerative colitis, scleroderma, hypertrophic scarring, Whipple's Disease, benign prostate hyperplasia, lung disorders in which IL-4 plays a role, conditions in which IL-4-induced epithelial barrier disruption plays a role, disorders of the digestive system in which IL-4 plays a role, allergic reactions to medication, Kawasaki disease, sickle cell crisis, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, and nephrosis. IL-4 antagonists also find use as adjuvants to allergy immunotherapy and as vaccine adjuvants.

IL-4 antagonists include, but are not limited to, IL-4 receptors (IL-4R), antibodies that bind IL-4, antibodies that bind IL-4R, IL-4 muteins that bind to IL-4R but do not induce a biological response, molecules that inhibit IL-4-induced signal transduction, and other compounds that inhibit a biological effect that results from the binding of IL-4 to a cell surface IL-4R.

Examples of IL-4 receptors are soluble forms of the human IL-4 receptor of SEQ ID NO:2. Particular antibodies provided herein include human monoclonal antibodies generated by procedures involving immunization of transgenic mice. Such human antibodies may be directed against human IL-4 receptor, for example.

BRIEF DESCRIPTION OF THE DRAWINGS

FIGS. 1A-C present the nucleotide sequence of the coding region of a human IL-4 receptor cDNA. The amino acid sequence encoded by the cDNA is presented as well. The cDNA clone was isolated from a cDNA library derived from a human T cell line T22. The encoded protein comprises (from N- to C-terminus) an N-terminal signal peptide, followed by an extracellular domain, a transmembrane region (underlined), and a cytoplasmic domain, as discussed further below. The DNA and amino acid sequences of FIGS. 1A to 1C are also presented in SEQ ID NOS:1 and 2, respectively.

FIGS. 2A to 2C depict targeted insertion of a neo cassette into the Sma I site of the µ1 exon. The construct was employed in generating transgenic mice, as described in Example 2. FIG. 2A is a schematic diagram of the genomic structure of the µ locus. The filled boxes represent the µ exons. FIG. 2B is a schematic diagram of the CmD targeting vector. The dotted lines denote those genomic p sequences included in the construct. Plasmid sequences are not shown. FIG. 2C is a schematic diagram of the targeted μ locus in which the neo cassette has been inserted into μ1.

FIGS. 3A and 3B present the nucleotide sequence of a vector designated pGP1k, as described in Example 3 below. This nucleotide sequence also is presented in SEQ ID NO:4.

DETAILED DESCRIPTION OF THE INVENTION

The present invention provides methods for treating certain conditions induced by IL-4, and for inhibiting biological activities of interleukin-4 (IL-4) in vivo. One method comprises administering an IL-4 antagonist to a patient afflicted with such a condition. Compositions for use in such methods for treating IL-4-induced conditions also are provided.

Among the conditions to be treated in accordance with the present invention are septic/reactive arthritis, dermatitis herpetiformis, chronic idiopathic urticaria, scleroderma, hypertrophic scarring, Whipple's Disease, benign prostate hyperplasia, lung disorders in which IL-4 plays a role, conditions in which IL-4-induced epithelial barrier disruption plays a role, disorders of the digestive system in which IL-4 plays a role, including inflammatory bowel disease and other inflammatory conditions in the gastrointestinal tract, allergic reactions to medication, Kawasaki disease, sickle cell disease (including sickle cell crisis), Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, and nephrosis, as described in more detail below. IL-4 antagonists also find use as adjuvants to allergy immunotherapy and as vaccine adjuvants.

IL-4 antagonists that may be employed include those compounds that inhibit a biological activity of IL-4. Biological activity(ies) of IL-4 that are inhibited by an antagonist in accordance with methods provided herein are activities that play a role in the particular disease to be treated.

Suitable antagonists include, but are not limited to, IL-4 receptors (IL-4R), antibodies that bind IL-4, antibodies that bind IL-4R, IL-4 muteins that bind to IL-4R but do not induce biological responses, molecules that inhibit IL-4-induced signal transduction, and other compounds that inhibit a biological effect that results from the binding of IL-4 to a cell surface IL-4R. Examples of such IL-4 antagonists are described in more detail below. Particular embodiments of the invention are directed to novel antibodies, polypeptides, and nucleic acid molecules, as described below. Antibodies provided herein include, but are not limited to, human monoclonal antibodies that bind to human IL-4 receptor, and that function as antagonists of both IL-4 and IL-13.

Indications

The present invention provides methods comprising administering an IL-4 antagonist to a patient afflicted with any of a number of conditions induced by IL-4. IL-4-induced conditions include conditions caused or exacerbated, directly or indirectly, by IL-4. Other factors or cytokines also may play a role in such conditions, but IL-4 induces or mediates the condition to some degree, i.e., at least in part.

The biological activities of IL-4 are mediated through binding to specific cell surface receptors, referred to as interleukin-4 receptors (IL-4R). IL-4-induced conditions include those arising from biological responses that result from the binding of IL-4 to a native IL-4 receptor on a cell, or which may be inhibited or suppressed by preventing IL-4 from binding to an IL-4 receptor. Conditions that may be treated include, but are not limited to, medical disorders characterized by abnormal or excess expression of IL-4, or by an abnormal host response to IL-4 production. Further examples are conditions in which IL-4-induced antibody production, or proliferation or influx of a particular cell type, plays a role. IL-4-induced disorders include those in which IL-4 induces upregulation of IL-4 receptors or enhanced production of another protein that plays a role in a disease (e.g., another cytokine).

A method for treating a mammal, including a human patient, who has such a medical disorder comprises administering an IL-4 antagonist to the mammal or otherwise contacting endogenous IL-4 with an antagonist, e.g., in an ex vivo procedure. Conditions that may be treated in accordance with the present invention include, but are not limited to, septic/reactive arthritis, dermatitis herpetiformis, urticaria (especially chronic idiopathic urticaria), ulcers, gastric inflammation, mucosal inflammation, ulcerative colitis, Crohn's Disease, inflammatory bowel disease, other disorders of the digestive system in which IL-4 plays a role (e.g., IL-4-induced inflammation of part of the gastrointestinal tract), conditions in which IL-4-induced barrier disruption plays a role (e.g., conditions characterized by decreased epithelial barrier function in the lung or gastrointestinal tract), scleroderma, hypertrophic scarring, Whipple's Disease, benign prostate hyperplasia, IL-4-induced pulmonary conditions (including those listed below), allergic reactions to medication, Kawasaki disease, sickle cell disease or crisis, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, nephrosis, pemphigus vulgaris or bullous pemphigoid (autoimmune blistering diseases), and myasthenia gravis (an autoimmune muscular disease). IL-4 antagonists also find use as adjuvants to allergy immunotherapy and as vaccine adjuvants, especially when directing the immune response toward a TH1 response would be beneficial in treating or preventing the disease in question.

Septic/Reactive Arthritis

IL-4 antagonists may be employed in treating septic arthritis, which also is known as reactive arthritis or bacterial arthritis. Septic arthritis can be triggered by (result from, or develop subsequent to) infection with such microbes as *Staphylococcus aureus, Chlamydia trachomatis, Yersinia* e.g., *Y. enterocolitica, Salmonella*, e.g., *S. enteritidis, Shigella* and *Campylobacter. S. aureus* has been reported to be the major human pathogen in septic arthritis, responsible for the majority of cases.

IL-4 and IL-4-dependent Th2 responses play roles in promoting septic arthritis. IL-4 antagonist(s) are employed in accordance with the invention, to inhibit IL-4 and also to suppress the Th2 response in patients having septic arthritis or at risk for developing septic arthritis.

IL-4 increases bacterial burden and bacterial persistence in joints, by inhibiting clearance of the bacteria. IL-4 antagonists may be employed to assist in the clearance of bacteria associated with reactive arthritis, thereby reducing clinical manifestations such as swelling in joints. IL-4 antagonists may be administered to a human patient afflicted with septic arthritis, to reduce IL-4-mediated joint inflammation. In one approach, an antagonist is injected into a joint, e.g., into synovial fluid in the knee.

The use of IL-4 antagonists may benefit patients having (or at risk for) septic arthritis by suppressing a TH2 response and promoting a TH1 response against the infection. TH2 cytokines may contribute to bacterial persistence in the joint, whereas a TH1 response plays a role in eliminating the bacteria.

The antagonists may be administered to patients infected with bacteria or other microbes such as those listed above, to prevent development of septic arthritis. Antagonist(s) may be administered after diagnosis with such an infection, but before development of clinical symptoms of septic arthritis.

Whipple's Disease

*Tropheryma whippelii* is the causative bacterium for Whipple's Disease, also known as intestinal lipodystrophy and lipophagia granulomatosis. The disease is characterized by steatorrhea, frequently generalized lymphadenopathy, arthritis, fever, and cough. Also reported in Whipple's Disease patients are an abundance of "foamy" macrophages in the jejunal lamina propria, and lymph nodes containing periodic acid-schiff positive particles appearing bacilliform by electron microscopy (*Steadman's Medical Dictionary*, 26$^{th}$ Edition, Williams & Wilkins, Baltimore, Md., 1995).

The use of IL-4 antagonist(s) may benefit patients having (or at risk for developing) Whipple's Disease, by restoring a normal balance between the TH1 and TH2 components of the patient's immune response. Increased production of IL-4 (a TH2-type cytokine) and decreased levels of certain TH1-type cytokines have been associated with Whipple's Disease. TH2 cytokines may contribute to bacterial persistence, whereas a TH1 response plays a role in clearing the causative bacteria. IL-4 antagonists may be administered to patients infected with *T. whippelii*, whether or not the patient exhibits clinical symptoms of Whipple's Disease.

Dermatitis Herpetiformis

Dermatitis herpetiformis, also known as Duhring's disease, is a chronic skin condition characterized by blistering skin lesions, cutaneous IgA deposits, and itching. Patients have an immunobullous skin disorder with an associated gluten sensitive enteropathy, which is mediated by a Th2 immune response. IL-4 antagonist(s) are administered in accordance with the present invention, to inhibit IL-4 and the Th2 response, thus promoting healing of current lesions and reducing or preventing the formation of blisters on the extensor body surfaces.

Hypertrophic Scarring

In accordance with the present invention, IL-4 antagonist(s) are administered to patients who have, or are susceptible to developing, hypertrophic scarring. In one method provided herein, an IL-4 antagonist is administered to a burn patient. An immune response to burns and other injury is believed to play a role in the pathogenesis of hypertrophic scarring. Increased production of TH2-type cytokines, including IL-4, and reduced levels of certain TH1-type cytokines have been reported in burn patients who have hypertropic scarring. The use of IL-4 antagonists may benefit patients having (or at risk for developing) hypertrophic scarring, by suppressing a TH2-type immune response.

Urticaria

Urticaria, especially chronic forms thereof such as chronic idiopathic urticaria (CIU), may be treated with an IL-4 antagonist in accordance with the present invention. CIU patients have higher serum levels of IL-4 than controls, and may have a predominantly TH2-type cytokine profile. Mast cells and Th2-type T cells are implicated as primary effector cells in chronic urticaria. IL-4 stimulates mast cell proliferation. Mast cell degranulation leads to histamine release, subsequent erythema, eosinophilia, redness of skin, and itching. IL-4 antagonists are administered to inhibit IL-4 and reduce the TH2-type response, thereby helping to control a patient's urticaria.

Ulcerative Colitis; Other Disorders of the Gastrointestinal Tract

IL-4 is implicated in the pathogenesis of ulcerative colitis. Th2-type cytokines including IL-4 may predominate in the colonic mucosa of patients with this disorder. The use of IL-4 antagonist(s) to suppress the TH2 response may alleviate this condition.

In addition to ulcerative colitis, other disorders of the gastrointestinal tract or digestive system may be treated with IL-4 antagonist(s). Examples of such disorders include, but are not limited to, inflammatory bowel disease (IBD), with ulcerative colitis and Crohn's Disease being forms of IBD, gastritis, ulcers, and mucosal inflammation.

Any gastrointestinal condition in which IL-4 plays a role may be treated with an IL-4 antagonist in accordance with the present invention. For example, conditions involving IL-4-induced inflammation of part of the gastrointestinal tract may be treated with an IL-4 antagonist. Particular embodiments are directed to treatment of chronic inflammatory conditions in the gastrointestinal tract.

Other embodiments are directed to conditions in which IL-4-induced barrier disruption plays a role, e.g., conditions characterized by decreased epithelial barrier function in at least a portion of the gastrointestinal tract. Such conditions may, for example, involve damage to the epithelium that is induced by IL-4, directly or indirectly.

The intestinal epithelium forms a relatively impermeable barrier between the lumen and the submucosa. Disruption of the epithelial barrier has been associated with conditions such as inflammatory bowel disease. See the discussion in Youakim, A. and M. Ahdieh (*Am. J. Physiol.* 276 (*Gastrointest. Liver Physiol.* 39):G1279-G1288, 1999), hereby incorporated by reference in its entirety. A damaged or "leaky" barrier can allow antigens to cross the barrier, which in turn elicits an immune response that may cause further damage to gastrointestinal tissue. Such an immune response may include recruitment of neutrophils or T cells, for example. An IL-4 antagonist may be administered to inhibit undesirable stimulation of an immune response.

Lung Disorders

Methods for treating IL-4-induced pulmonary disorders are provided herein. Such disorders include, but are not limited to, lung fibrosis, including chronic fibrotic lung disease, other conditions characterized by IL-4-induced fibroblast proliferation or collagen accumulation in the lungs, pulmonary conditions in which a TH2-type immune response plays a role, conditions characterized by decreased barrier function in the lung (e.g., resulting from IL-4-induced damage to the epithelium), or conditions in which IL-4 plays a role in an inflammatory response.

Cystic fibrosis is characterized by the overproduction of mucus and development of chronic infections. Inhibiting IL-4 and the Th2 response will reduce mucus production and help control infections such as allergic bronchopulmonary aspergillosis (ABPA).

Allergic bronchopulmonary mycosis occurs primarily in patients with cystic fibrosis or asthma, where a Th2 immune response is dominant. Inhibiting IL-4 and the Th2 response will help clear and control these infections.

Chronic obstructive pulmonary disease is associated with mucus hypersecretion and fibrosis. Inhibiting IL-4 and the Th2 response will reduce the production of mucus and the development of fibrous thereby improving respiratory function and delaying disease progression.

Bleomycin-induced pneumopathy and fibrosis, and radiation-induced pulmonary fibrosis are disorders characterized by fibrosis of the lung which is manifested by the influx of Th2, $CD4^+$ cells and macrophages, which produce IL-4 which in turn mediates the development of fibrosis. Inhibiting IL-4 and the Th2 response will reduce or prevent the development of these disorders.

Pulmonary alveolar proteinosis is characterized by the disruption of surfactant clearance. IL-4 increases surfactant product. Use of IL-4 antagonists will decrease surfactant production and decrease the need for whole lung lavage.

Adult respiratory distress syndrome (ARDS) may be attributable to a number of factors, one of which is exposure to toxic chemicals. One patient population susceptible to ARDS is critically ill patients who go on ventilators. ARDS is a frequent complication in such patients. IL-4 antagonists may alleviate ARDS by reducing inflammation and adhesion molecules, although methods for treating such patients in accordance with the present invention are not limited by a particular mechanism of action. IL-4 antagonists may be used to prevent or treat ARDS.

Sarcoidosis is characterized by granulomatus lesions. Use of IL-4 antagonists to treat sarcoidosis, particularly pulmonary sarcoidosis, is contemplated herein.

Conditions in which IL-4-induced barrier disruption plays a role (e.g., conditions characterized by decreased epithelial barrier function in the lung) may be treated with IL-4 antagonist(s). Damage to the epithelial barrier in the lungs may be induced by IL-4 directly or indirectly. The epithelium in the lung functions as a selective barrier that prevents contents of the lung lumen from entering the submucosa. A damaged or "leaky" barrier allows antigens to cross the barrier, which in turn elicits an immune response that may cause further damage to lung tissue. Such an immune response may include recruitment of eosinophils or mast cells, for example. An IL-4 antagonist may be administered to inhibit such undesirable stimulation of an immune response.

IL-4 antagonists may be employed to promote healing of lung epithelium, thus restoring barrier function. IL-4 antagonists may be employed to promote healing of lung epithelium in asthmatics, for example. Alternatively, the antagonist is administered for prophylactic purposes, to prevent IL-4-induced damage to lung epithelium.

Tuberculosis

A TH2-type immune response is implicated in playing a role in causing tissue damage (e.g., necrosis of lung tissue) in tuberculosis (TB) patients. Elevated levels of IL-4 are associated with TB. IL-4 production may be particularly elevated in cavitary tuberculosis (i.e., in TB patients who have developed pulmonary cavities, which can be detected/visualized by such techniques as radiographs of the chest).

IL-4 antagonists may benefit TB patients (especially those with cavitary TB) by suppressing a TH2-type immune response, or by binding (and inactivating) excess secreted IL-4. Methods for treating such patients in accordance with the present invention are not limited by a particular mechanism of action, however. IL-4 antagonists advantageously are administered in an amount that restores the desired balance between the TH1 and TH2 components of the immune response, and reduces IL-4-induced tissue damage in a patient.

Churg-Strauss Syndrome

Churg-Strauss syndrome, a disease also known as allergic granulomatous angiitis, is characterized by inflammation of the blood vessels in persons with a history of asthma or allergy, and by eosinophilia. IL-4 antagonist(s) may be administered to alleviate inflammation in patients with this syndrome. The use of IL-4 antagonists to suppress a TH2-type immune response, and to combat eosinophilia, would benefit the patients.

Pre-Eclampsia

Pre-eclampsia is a toxemia of late pregnancy. The condition is characterized by a sharp rise in blood pressure, generally accompanied by edema and albuminuria, during the third term of pregnancy.

Elevated TH1-type and TH2-type immune responses may play a role in the condition. One method provided herein comprises administering an IL-4 antagonist to a pregnant woman who has developed pre-eclampsia. The IL-4 antagonist is administered in an amount, and for a period of time, sufficient to reduce the level of IL-4 (or of TH2-type cytokines collectively) to a level that is considered normal during pregnancy. In general, the IL-4 antagonist is administered repeatedly throughout the duration of the pregnancy.

Scleroderma

IL-4 antagonist(s) are administered to scleroderma patients in accordance with the invention. The antagonists reduce IL-4-induced collagen synthesis by fibroblasts in the patients. The antagonists may be employed in preventing or reducing fibrosis in skin and lung tissues, as well as other tissues in which fibrosis occurs in scleroderma patients, suppressing collagen synthesis in such tissues, and in treating scleroderma-related pulmonary disease.

Benign Prostate Hyperplasia

Benign prostate hyperplasia (BPH), also known as benign prostate hypertrophy, may be treated with IL-4 antagonist(s). While not wishing to be bound by a particular mechanism of action, administration of an IL-4 inhibitor may benefit a patient with BPH by suppressing IL-4-induced inflammation, or by suppressing a TH2-type immune response.

Grave's Disease

Antibodies directed against thyrotropin receptor play an important role in Grave's Disease, a disorder characterized by hyperthyroidism. Studies of cytokine production in Grave's Disease patients show a shift toward a TH2-type cytokine response. Use of an IL-4 antagonist to suppress the TH2-type immune response, and suppress antibody production, would benefit Grave's Disease patients.

Sickle Cell Disease

Sickle cell disease patients typically experience intermittent periods of acute exacerbation called crises, with the crises being categorized as anemic or vaso-occlusive. IL-4 antagonists find use in treating or preventing sickle cell crisis, especially in patients with elevated IL-4 levels or in whom the immune response has shifted toward a TH2-type response. Sickle cell disease (especially sickle cell crisis) has been associated with increased susceptibility to infectious diseases, including bacterial infections. Administering IL-4 antagonists to sickle cell disease patients may help the patient mount an immune response against infectious diseases.

Sjogren's Syndrome

The autoimmune disease known as Sjogren's syndrome or sicca syndrome typically combines dry eyes and dry mouth with a disorder of the connective tissues, such as rheumatoid arthritis, lupus, scleroderma, or polymyositis. The vast majority of patients are middle age (or older) females. Sjogren's syndrome is an inflammatory disease of glands (e.g., lacrimal and salivary glands) and other tissues of the body. The syndrome typically is associated with autoantibody production.

IL-4 antagonists may be administered to reduce the inflammatory response (such as inflammation of glands, including lacrimal glands) in such patients. IL-4 antagonists may benefit Sjogren's syndrome patients by suppressing a TH2-type immune response, or by binding (and inactivating) excess IL-4 at inflammatory lesions. Methods for treating patients in accordance with the present invention are not limited by a particular mechanism of action, however.

Autoimmune Lymphoproliferative Syndrome Manifestations of autoimmune lymphoproliferative syndrome include lymphoproliferation and autoantibody production. Patients with the syndrome reportedly have an inherited deficiency in apoptosis. IL-4 antagonists may benefit patients with this syndrome by suppressing a TH2-type immune response, or by binding (and inactivating) excess IL-4 at sites of inflammation. Methods for treating such patients in accordance with the present invention are not limited by a particular mechanism of action, however.

Autoimmune Hemolytic Anemia

Excessive IL-4 secretion, and a deficiency in TH1-type cytokines, are implicated in contributing to the pathogenesis of autoimmune hemolytic anemia. IL-4 antagonists are administered in accordance with the present invention, to benefit the patients by reducing autoantibody production, and by restoring a more normal balance between the TH1 and TH2 components of the immune response.

Autoimmune Uveitis

Uveitis involves inflammation of the uvea (generally considered to include the iris, ciliary body, and choroid, considered together). Excess IL-4 secretion is implicated as playing a role in pathogenesis of this sight-threatening inflammatory eye disease. In accordance with the present invention, IL-4 antagonist(s) are administered to a uveitis patient to reduce disease severity. In one embodiment, IL-4 antagonist(s) are administered to an individual who has autoimmune uveoretinitis.

Kawasaki Disease

Also known as the mucocutaneous lymph node syndrome, Kawasaki disease (KD) mainly afflicts young children. The disease is characterized by particular changes in the mucus membranes lining the lips and mouth, and by enlarged, tender lymph glands. Symptoms typically include fever, conjunctivitis, inflammation of the lips and mucous membranes of the mouth, swollen glands in the neck, and a rash covering the hands and feet, leading to hardened, swollen and peeling skin on hands and feet. In children with Kawasaki Disease (KD), inflammation of arteries (vasculitis) may develop. Due to the effect of the disease on the vascular system, KD reportedly is the main cause of acquired heart disease in children.

IL-4 antagonists may be administered to patients with Kawasaki Disease, to reduce the elevated levels of IL-4 in the patient. Excessive IL-4 secretion and a deficiency in TH1-type cytokines contribute to the pathogenesis of the disease.

Barrett's Esophagus

Barrett's esophagus is a condition characterized by alteration (subsequent to irritation) of the cells in the epithelial tissue that lines the lower portion of the esophagus. Frequent reflux of the stomach contents into the esophagus, over time, can lead to Barrett esophagus. Patients with Barrett esophagus are at risk for developing esophageal cancer (e.g., adenocarcinoma). While not wishing to be bound by a particular mechanism of action, administration of an IL-4 antagonist may benefit a patient with Barrett's esophagus by suppressing a TH2-type immune response. In one embodiment, an IL-4 antagonist is administered to a patient with esophagitis, to inhibit progression to Barrett's esophagus.

Nephrosis

Nephrosis, also known as nephrotic syndrome, is kidney disease that is non-inflammatory and non-malignant. In the condition known as minimal change nephrosis, glomerular damage (believed to arise from structural changes in glomerular visceral epithelial cells) results in abnormalities that include proteinuria. A TH2-type immune response (especially secretion of the TH2-type cytokines IL-4 and IL-13) are implicated as playing a role in pathogenesis of minimal change nephrosis.

Other Indications

Additional examples of conditions that may be treated in accordance with the present invention include but are not limited to the following. IL-4 antagonists may be employed in treating or preventing hyper IgE syndrome, idiopathic hypereosinophil syndrome, allergic reactions to medication, autoimmune blistering diseases (e.g., pemphigus vulgaris or bullous pemphigoid), myasthenia gravis (an autoimmune muscular disease), and chronic fatigue syndrome. IL-4 inhibitors may be employed in treating GVHD; particular methods for treating GVHD combination therapy with other therapeutic agents as described below. IL-4 inhibitors also find use in treating or preventing hepatotoxicity induced by drugs such as diclofenac (a non-steroidal anti-inflammatory drug).

An IL-4 antagonist may be employed as an adjuvant to allergy immunotherapy treatment. IL-4 antagonists find further use as vaccine adjuvants, such as adjuvants for cancer vaccines and infectious disease vaccines. The use of IL-4 antagonists is especially advantageous when favoring a TH1-type immune response would be beneficial in preventing or treating the condition for which the vaccine is being administered. IL-4 antagonists may be employed when reducing an antibody-mediated immune response and/or promoting a T-cell-mediated immune response is desired.

IL-4 Antagonists

IL-4 antagonists that may be employed in accordance with the present invention include compounds that inhibit a biological activity of IL-4. The IL-4-induced biological activities to be inhibited by the methods provided herein are activities that directly or indirectly play a role in the condition to be treated.

Examples of IL-4 antagonists include, but are not limited to, IL-4 receptors (IL-4R), antibodies, other IL-4-binding molecules, and IL-4 muteins as discussed further below. The antibodies may bind IL-4 or may bind an IL-4 receptor, for example.

Antagonists that bind IL-4 include but are not limited to IL-4 receptors and anti-IL-4 antibodies. Endogenous IL-4 that becomes bound to such an antagonist is thereby prevented from binding its natural receptor on cell surfaces in vivo, and thus cannot manifest IL-4-mediated biological activities.

Different types of antagonists may act at different sites or by different mechanisms of action. Examples include but are not limited to antagonists that interfere with binding of IL-4 to cell surface receptors or that inhibit signal transduction. The site of action may be intracellular (e.g., by interfering with an intracellular signaling cascade), on a cell surface, or extracellular. Antagonists that act by interfering with the interaction of IL-4 with IL-4R may bind to either IL-4 or to the receptor. An antagonist need not completely inhibit an IL-4 induced activity to find use in the present invention; rather, antagonists that reduce a particular activity of IL-4 are contemplated for use as well.

The above-presented discussions of particular mechanisms of action for IL-4 antagonists in treating particular diseases are illustrative only, and the methods presented herein are not bound thereby. The mechanisms of action by which IL-4 antagonists ameliorate diseases are not limited to those discussed above.

In treating particular disorders, an IL-4 antagonist may reduce the amount of active IL-4 at a particular site within the body that is involved in the disorder. Antagonists that bind IL-4 such that it no longer can bind to endogenous cellular receptors functionally reduce the amount of active IL-4 available for inducing biological responses.

An IL-4 antagonist may alleviate a disorder by reducing the amount of free endogenous IL-4 that is circulating in the body, e.g., in the bloodstream or in a particular tissue. When the action of IL-4 on such tissue plays a role in pathogenesis of the disease, the antagonist serves to block action of IL-4 in the tissue, thereby alleviating the disorder. In a further example, antagonists may inhibit IL-4-induced recruitment of cells to a site or tissue within the body, wherein such recruitment plays a role in causing or exacerbating a disease. The antagonists may inhibit an IL-4-mediated influx of cells involved in an immune or inflammatory response. An antagonist may act by reducing proliferation, activation, migration, influx, or accumulation of a particular cell type, or by inhibiting a biological response directly or indirectly attributable to a particular cell type. Examples of particular cell types are fibroblasts, mast cells, and eosinophils.

As discussed above, some conditions may be treated by suppressing a TH2-type immune response. IL-4 is associated with a TH2 response, and is one of the cytokines secreted by T-helper cells of type 2 (TH2 cells). An IL-4 antagonist may be administered to reduce a TH2-type immune response. The IL-4 antagonist may be said to reduce proliferation of TH2 cells, to suppress a TH2 response, to shift the immune response toward a TH1 response, or to favor a TH1-type response. The use of antagonists of other cytokines associated with a TH2-type immune response is discussed below. Antagonists of other TH2-type cytokine(s), such as IL-5, IL-10, or IL-13, may be administered to patients who have a disorder involving elevated levels of such cytokines. Techniques for measuring the amount of such cytokines in a patient, e.g., in the patient's serum, are well known.

One embodiment of the invention is directed to a method for inhibiting IL-4-induced damage to epithelium, comprising administering an IL-4 antagonist to an individual who has, or is at risk of developing, a condition in which IL-4-mediated epithelial barrier disruption plays a role. In accordance with the present invention, barrier function studies revealed that IL-4 plays a role in reduction of barrier function in models of lung epithelium and intestinal epithelium, and that a soluble human IL-4 receptor polypeptide (an IL-4 antagonist) inhibits the IL-4-mediated reduction of barrier function (see example 7).

Particular embodiments of methods provided herein comprise administering an IL-4 antagonist to inhibit IL-4-induced damage to epithelium in the gastrointestinal tract or lung. Such methods may be employed to prevent epithelial damage, or to restore epithelial barrier function (i.e., promote repair or healing of the epithelium). The ability of an IL-4 antagonist to inhibit IL-4-induced damage to epithelium may be confirmed in any of a number of suitable assays, such as those described in example 7 below.

Any inflammation associated with (or subsequent to) an infection also may be treated with an IL-4 antagonist. The antagonist may be administered to inhibit any IL-4-induced component of an inflammatory response resulting from microbial infection in the gastrointestinal tract, for example.

Combinations of two or more antagonists may be employed in methods and compositions of the present invention. Examples of suitable IL-4 antagonists are as follows.

IL-4 Receptor

A preferred IL-4 antagonist is an IL-4 receptor (IL-4R). When administered in vivo, IL-4R polypeptides circulate in the body and bind to circulating endogenous IL-4 molecules, preventing interaction of IL-4 with endogenous cell surface IL-4 receptors, thus inhibiting transduction of IL-4-induced biological signals.

IL-4 receptors are described in U.S. Pat. No. 5,599,905; Idzerda et al., *J. Exp. Med.* 171:861-873, March 1990 (human IL-4R); and Mosley et al., *Cell* 59:335-348, Oct. 20, 1989 (murine IL-4R); each of which is hereby incorporated by reference. The protein described in those three references is sometimes referred to in the scientific literature as IL-4Rα. Unless otherwise specified, the terms "IL-4R" and "IL-4 receptor" as used herein encompass this protein in various forms that are capable of functioning as IL-4 antagonists, including but not limited to soluble fragments, fusion proteins, oligomers, and variants that are capable of binding IL-4, as described in more detail below.

The nucleotide sequence of a human IL-4R cDNA, and the amino acid sequence encoded thereby, are set forth in FIGS. 1A-1C. The cDNA clone was isolated from a cDNA library derived from a CD4$^+$/CD8$^-$ human T cell clone designated T22, as described in Idzerda et al., *J. Exp. Med.,* 171:861, March 1990, and in U.S. Pat. No. 5,599,905, which are hereby incorporated by reference in their entirety. The DNA and amino acid sequences of FIGS. 1A-1C are presented in SEQ ID NO:1 and SEQ ID NO:2, respectively.

The encoded human IL-4R protein comprises (from N- to C-terminus) an N-terminal signal peptide, followed by an extracellular domain, a transmembrane region, and a cytoplasmic domain. The transmembrane region, which is underlined in FIG. 1A, corresponds to amino acids 208 through 231. The cytoplasmic domain comprises amino acids 232 through 800.

A signal peptide includes amino acids −25 to −1 of SEQ ID NO:2. An alternative signal peptide cleavage site occurs between residues −3 and −2 of SEQ ID NO:2, such that the signal peptide corresponds to residues −25 through −3.

As is recognized in the pertinent field, the signal peptide cleavage site for a given protein may vary according to such factors as the particular expression system (especially the host cells) in which the protein is expressed. The exact boundaries of the signal peptide, and thus the extracellular domain, of a given recombinant protein thus may depend on the expression system employed. Further, the signal peptide may be cleaved at more than one position, generating more than one species of polypeptide in a preparation of recombinant protein.

In one embodiment, in which an expression vector comprises DNA encoding amino acids −25 through 207 of SEQ ID NO:2, the expressed recombinant IL-4R includes two species of mature soluble human IL-4R. The expressed polypeptides include a major species corresponding to amino acids −2 to 207 and a minor species corresponding to amino acids 1 to 207 of SEQ ID NO:2. Two alternate forms of the extracellular domain of human IL-4R thus correspond to residues −2 to 207 and 1 to 207 of SEQ ID NO:2. The term "mature" refers to a protein in a form lacking a signal peptide or leader sequence, as is understood in the pertinent art.

Among the IL-4 receptors suitable for use herein are IL-4R fragments. Truncated IL-4R polypeptides may occur naturally, e.g., as a result of proteolytic cleavage, post-translational processing, or alternative splicing of mRNA. Alternatively, fragments may be constructed by deleting terminal or internal portions of an IL-4R sequence, e.g., via recombinant DNA technology. Fragments that retain the ability to bind IL-4 may be identified in conventional binding assays. Such fragments may be soluble fragments, as discussed below.

In a preferred embodiment of the invention, the antagonist comprises a soluble form of the IL-4R. A soluble IL-4 receptor is a polypeptide that is secreted from the cell in which it is expressed, rather than being retained on the cell surface. The full length human IL-4R protein of SEQ ID NO:2 is a transmembrane protein, which, as described above, comprises an N-terminal signal peptide, followed by an extracellular domain, a transmembrane region, and a C-terminal cytoplasmic domain. Soluble IL-4R polypeptides lack the transmembrane region that would cause retention on the cell, and the soluble polypeptides consequently are secreted into the culture medium. The transmembrane region and intracellular domain of IL-4R may be deleted or substituted with hydrophilic residues to facilitate secretion of the receptor into the cell culture medium.

Particular embodiments of soluble IL-4R polypeptides lack the transmembrane region but comprise the extracellular domain (the complete extracellular domain or a fragment thereof that is capable of binding IL-4). As one option, the polypeptide comprises all or part of the cytoplasmic domain, as well as the extracellular domain (or fragment of the extracellular domain), but lacks the transmembrane region.

Examples of soluble human IL-4R polypeptides include, but are not limited to, polypeptides comprising amino acid residues x to y of SEQ ID NO:2, wherein x represents 1 or −2 and y represents an integer from 197 to 207. Preferred embodiments include polypeptides comprising residues 1 to 207 or −2 to 207 of SEQ ID NO:2.

A protein preparation administered as an IL-4 antagonist may comprise more than one form of IL-4R. For example, the preparation may comprise polypeptide molecules consisting of amino acids 1 to 207 of SEQ ID NO:2, as well as polypeptides consisting of amino acids −2 to 207 of SEQ ID NO:2.

IL-4R polypeptides arising from alternative mRNA constructs, e.g., which can be attributed to different mRNA splicing events following transcription, and which yield polypeptide translates capable of binding IL-4, are among the IL-4R polypeptides disclosed herein. Such alternatively spliced mRNAs may give rise to soluble polypeptides.

Further examples of IL-4 receptors that may be employed in the methods provided herein are variants having amino acid sequences which are substantially similar to the native interleukin-4 receptor amino acid sequence of SEQ ID NO:2, or fragments thereof. Variant IL-4 receptor polypeptides that are capable of functioning as IL-4 antagonists may be employed in the methods of the present invention.

Any of a number of conventional assay techniques may be employed to confirm that a given form of IL-4R (e.g., an IL-4R fragment or variant) functions as an IL-4 antagonist. Examples include binding assays or assays that test the ability of a given IL-4R polypeptide to inhibit transduction of an IL-4-induced biological signal. Examples of suitable in vitro assays are described below.

"Substantially similar" IL-4 receptors include those having amino acid or nucleic acid sequences that vary from a native sequence by one or more substitutions, deletions, or additions, but retain a desired biological activity of the IL-4R protein. Examples of nucleic acid molecules encoding IL-4 receptors include, but are not limited to: (a) DNA derived from the coding region of a native mammalian IL-4R gene; (b) DNA that is capable of hybridization to a DNA of (a) under moderately stringent conditions and which encodes an IL-4R having a biological activity of a native IL-4R; or (c) DNA that is degenerate as a result of the genetic code to a DNA defined in (a) or (b) and which encodes an IL-4R having a biological activity of a native IL-4R. Due to code degeneracy, there can be considerable variation in nucleotide sequences encoding the same amino acid sequence.

Variants may be naturally occurring, such as allelic variants or those arising from alternative splicing of mRNA. Alternatively, variants may be prepared by such well known techniques as in vitro mutagenesis.

A variant sequence identified by Idzerda et al., supra, comprises a GTC codon encoding the amino acid valine (Val) at position 50, instead of isoleucine (Ile). The variant sequence is otherwise identical to the sequence of SEQ ID NOS:1 and 2. IL-4R fragments, such as soluble fragments, comprising Val at position 50 are provided herein.

In particular embodiments, an IL-4 receptor DNA or amino acid sequence is at least 80 percent identical to the sequence of a native IL-4R. Preferably, an IL-4R DNA or polypeptide comprises a sequence that is at least 90 percent identical to a native IL-4R DNA or amino acid sequence. One example is a human IL-4R comprising an amino acid sequence that is at least 80 percent identical to the sequence presented in SEQ ID NO:2. Another example is a soluble IL-4R comprising an amino acid sequence at least 80 percent identical to the sequence of the extracellular domain of human IL-4R. Further examples are polypeptides comprising amino acid sequences that are at least 90 percent identical to the sequence presented in SEQ ID NO:2, or a fragment thereof. In a particular embodiment, the polypeptide comprises no more than 10 amino acid substitutions. IL-4R polypeptides that retain the ability to bind IL-4 may be identified in conventional binding assays.

Percent similarity or percent identity may be determined, for example, by comparing DNA or amino acid sequence information using the GAP computer program, version 6.0, available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math.* 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, ed., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

IL-4R polypeptides that vary from native proteins but possess a desired property may be constructed by, for example, substituting or deleting residues not needed for the particular biological activity. Substitutions may be conservative substitutions, such that a desired biological property of the protein is retained. Amino acids may be replaced with residues having similar physicochemical characteristics.

Cysteine residues can be deleted or replaced with other amino acids to prevent formation of incorrect intramolecular disulfide bridges upon renaturation. Other alterations of a native sequence involve modification of adjacent dibasic amino acid residues, to enhance expression in yeast host cells in which KEX2 protease activity is present.

The present invention also includes IL-4R with or without associated native-pattern glycosylation. The glycosylation pattern may vary according to the type of host cells in which the protein is produced. Another option is inactivation of N-glycosylation sites by site-specific mutagenesis. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

Oligonucleotide-directed site-specific mutagenesis procedures can be employed to provide an altered gene having particular codons altered according to the substitution, deletion, or insertion required. Examples of techniques for making such alterations are described in Walder et al. (*Gene* 42:133, 1986); Bauer et al. (*Gene* 37:73, 1985); Craik (*BioTechniques, January* 1985, 12-19); Smith et al. (*Genetic Engineering: Principles and Methods*, Plenum Press, 1981); and U.S. Pat. Nos. 4,518,584 and 4,737,462.

IL-4 receptors that may be employed also include derivatives, e.g., various structural forms of the primary protein which retain a desired biological activity. Due to the presence of ionizable amino and carboxyl groups, for example, an IL-4R protein may be in the form of acidic or basic salts, or in neutral form. Individual amino acid residues may also be modified by oxidation or reduction. The primary amino acid structure may be modified by forming covalent or aggregative conjugates with other chemical moieties, such as glycosyl groups, lipids, phosphate, acetyl groups and the like, or by creating amino acid sequence mutants. PEGylated derivatives (modified with polyethylene glycol) are contemplated. Covalent derivatives may be prepared by linking particular functional groups to IL-4R amino acid side chains or at the N- or C-termini. IL-4R derivatives may also be obtained by cross-linking agents, such as M-maleimidobenzoyl succinimide ester and N-hydroxysuccinimide, at cysteine and lysine residues. IL-4R proteins may also be covalently bound through reactive side groups to various insoluble substrates, such as cyanogen bromide-activated, bisoxirane-activated, carbonyl-diimidazole-activated or tosyl-activated agarose structures, or by adsorbing to polyolefin surfaces (with or without glutaraldehyde cross-linking).

Other derivatives of IL-4R within the scope of this invention include covalent or aggregative conjugates of IL-4R or its fragments with other proteins or polypeptides, such as by expression of recombinant fusion proteins comprising heterologous polypeptides fused to the N-terminus or C-terminus of an IL-4R polypeptide. For example, the conjugated peptide may be a heterologous signal (or leader) polypeptide, e.g., the yeast α-factor leader, or a peptide such as an epitope tag. IL-4R-containing fusion proteins can comprise peptides added to facilitate purification or identification of IL-4R (e.g., poly-His). Specific examples of poly-His fusion constructs that is biologically active are soluble human IL-4R (e.g., comprising residues −2 to 207 or 1-207 of SEQ ID NO:2) His His and soluble human IL-4R His His His His His His. An amino acid sequence of IL-4 receptor can also be linked to the Flag® peptide Asp-Tyr-Lys-Asp-Asp-Asp-Asp-Lys (DYKDDDDK) (SEQ ID NO:3) as described in Hopp et al., *Bio/Technology* 6:1204, 1988, and U.S. Pat. No. 5,011,912. The Flag® peptide is highly antigenic and provides an epitope reversibly bound by a specific monoclonal antibody, enabling rapid assay and facile purification of expressed recombinant protein. Reagents useful for preparing fusion proteins in which the Flag® peptide is fused to a given polypeptide are commercially available (Sigma, St. Louis, Mo.).

Oligomers that contain IL-4R polypeptides may be employed as IL-4 antagonists. Oligomers may be in the form of covalently-linked or non-covalently-linked dimers, trimers, or higher oligomers. Oligomers comprising two or more IL-4R polypeptides are contemplated for use, with one example being a homodimer. Other oligomers include heterodimers, heterotrimers, and the like, which comprise an IL-4R polypeptide as well as at least one polypeptide that is not derived from the IL-4R of SEQ ID NO:2.

One embodiment is directed to oligomers comprising multiple IL-4R polypeptides joined via covalent or non-covalent interactions between peptide moieties fused to the IL-4R polypeptides. Such peptides may be peptide linkers (spacers), or peptides that have the property of promoting oligomerization. Leucine zippers and certain polypeptides derived from antibodies are among the peptides that can promote oligomerization of IL-4R polypeptides attached thereto, as described in more detail below.

In particular embodiments, the oligomers comprise from two to four IL-4R polypeptides. The IL-4R moieties of the oligomer may be in any of the forms described above, e.g., variants or fragments. Preferably, the oligomers comprise soluble IL-4R polypeptides.

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1-10.19.11, 1992).

One embodiment of the present invention is directed to a dimer comprising two fusion proteins created by fusing IL-4R to the Fc region of an antibody. A gene fusion encoding the IL-4R/Fc fusion protein is inserted into an appropriate expression vector. IL-4R/Fc fusion proteins are expressed in host cells transformed with the recombinant expression vector, and allowed to assemble much like antibody molecules, whereupon interchain disulfide bonds form between the Fc moieties to yield divalent IL-4R.

The term "Fc polypeptide" as used herein includes native and mutein forms of polypeptides derived from the Fc region of an antibody. Truncated forms of such polypeptides containing the hinge region that promotes dimerization are also included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992-4001, 1994). The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, IL-4R may be substituted for the variable portion of an antibody heavy or light chain. If fusion proteins are made with both heavy and light chains of an antibody, it is possible to form an oligomer with as many as four IL-4R extracellular regions.

Soluble recombinant fusion proteins comprising an IL-4R and various portions of the constant region of an immunoglobulin are described in EP 464,533, along with procedures for preparing such fusion proteins and dimers thereof. Among the fusion proteins described in EP 464,533 are those comprising the extracellular portion of human IL-4R and an Fc polypeptide.

Alternatively, the oligomer is a fusion protein comprising multiple IL-4R polypeptides, with or without peptide linkers (spacer peptides). Among the suitable peptide linkers are those described in U.S. Pat. Nos. 4,751,180 and 4,935,233.

Another method for preparing oligomeric IL-4R involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267-278, 1994). In one approach, recombinant fusion proteins comprising a soluble IL-4R polypeptide fused to a leucine zipper peptide are expressed in suitable host cells, and the soluble oligomeric IL-4R that forms is recovered from the culture supernatant.

One example of a heterodimer comprises an IL-4R polypeptide derived from the human IL-4R of SEQ ID NO:2, and an IL-2Rγ polypeptide. IL-2Rγ (also known as IL-2Rγ$_c$) is described in U.S. Pat. No. 5,510,259 and in Takeshita et al. (*Science* 257:379, 17 Jul. 1992), which are incorporated by reference herein. The polypeptides may be in one of the various forms described herein, e.g., soluble fragments, variants, and the like, derived from the indicated proteins. One embodiment of such a heterodimer comprises a soluble IL-4R/Fc fusion protein and a soluble IL-2Rγ/Fc fusion protein. Such heterodimers are described in WO 96/11213, along with IL-4R homodimers.

Other examples of heterodimers comprise an IL-4R subunit (preferably a soluble fragment of the protein of SEQ ID NO:2) and at least one IL-13 receptor subunit. IL-13 receptor (IL-13R) complexes and IL-13R polypeptides (such as polypeptides designated IL-13Rα1 and IL-13Rα2) are described in Zurawski et al., *J. Biol. Chem.* 270 (23), 13869, 1995; de Vries, *J. Allergy Clin. Immunol.* 102(2):165, August 1998; Callard et al. Immunology Today, 17(3):108, March 1996, and U.S. Pat. No. 5,710,023, each of which is incorporated by reference herein. In one embodiment, a heterodimer comprises a soluble human IL-4R and a soluble IL-13R (preferably a soluble form of the polypeptide described in U.S. Pat. No. 5,710,023 or IL-13Rα1). The components of heterodimers may be any suitable form of the polypeptides that retains the desired activity, such as fragments, variants, or fusion proteins (e.g., fusions of soluble receptor polypeptides with Fc polypeptides, leucine zipper peptides, peptide linkers, or epitope tags).

IL-4 receptor polypeptides and fusion proteins described herein may be prepared by any of a number of conventional techniques. IL-4R polypeptides may be purified from cells that naturally express the receptor (such as the cells discussed in Park et al., *Proc. Natl. Acad. Sci. USA* 84:1669-673, 1987), or may be produced in recombinant expression systems, using well known techniques. Expression systems for use in producing IL-4R include those described in U.S. Pat. No. 5,599,905, which is hereby incorporated by reference.

A variety of expression systems are known for use in producing recombinant proteins. In general, host cells are transformed with a recombinant expression vector that comprises DNA encoding a desired IL-4R polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., *Cell* 23:175, 1981), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al. (*EMBO J.* 10: 2821, 1991). Appropriate cloning and expression vectors for use with bacterial, fungal, yeast, and mammalian cellular hosts are described by Pouwels et al. (*Cloning Vectors: A Laboratory Manual*, Elsevier, N.Y., 1985).

The transformed cells are cultured under conditions that promote expression of the IL-4R, and the polypeptide is recovered by conventional protein purification procedures. One such purification procedure includes the use of affinity chromatography, e.g., over a matrix having IL-4 bound thereto. Expressed IL-4R will be deposited in the cell membrane or secreted into the culture supernatant, depending on the IL-4R DNA selected. Polypeptides contemplated for use herein include substantially homogeneous recombinant mammalian IL-4R polypeptides substantially free of contaminating endogenous materials.

Antibodies

Antibodies that function as IL-4 antagonists may be employed in the methods of the present invention. The antibodies preferably are monoclonal antibodies or antigen-binding fragments thereof. Advantageously, humanized or chimeric monoclonal antibodies are employed. Most preferred are human monoclonal antibodies prepared using transgenic mice, as described below.

Examples of suitable antibodies are those that interfere with the binding of IL-4 to an IL-4 receptor. Such antibodies, referred to herein as blocking antibodies, may be raised against either IL-4 or IL-4R, and screened in conventional assays for the ability to interfere with binding of IL-4 to IL-4 receptors. Examples of suitable assays are assays that test the antibodies for the ability to inhibit binding of IL-4 to cells expressing IL-4R, or that test antibodies for the ability to reduce a biological or cellular response that results from the binding of IL-4 to cell surface IL-4 receptors.

It has been reported that IL-4Rα is a component of certain multi-subunit IL-13 receptor complexes (Zurawski et al., *J. Biol. Chem.* 270 (23), 13869, 1995; de Vries, *J. Allergy Clin. Immunol.* 102(2):165, August 1998; and Callard et al. Immunology Today, 17(3):108, March 1996, each incorporated by reference herein). Thus, some antibodies raised against IL-4Rα may interfere with the binding of IL-13 to such receptor complexes.

In one embodiment, antibodies directed against IL-4R block binding of IL-4 and also IL-13 to cells. The antibodies inhibit IL-4-induced biological activity and also inhibit IL-13-induced activity, and thus may be employed in treating conditions induced by either or both cytokines. Examples of such conditions include but are not limited to IgE-mediated conditions, asthma, allergic conditions, allergic rhinitis, and dermatitis including atopic dermatitis.

Antibodies that bind to IL-4R and inhibit IL-4 binding may be screened in various conventional assays to identify those antibodies that also interfere with the binding of IL-13 to such receptor complexes. Antibodies may be screened in binding assays or tested for the ability to inhibit an IL-4-induced and an IL-13-induced biological activity. An example of a suitable assay is illustrated in Example 5 below.

Antibodies specific for IL-4 or IL-4R may be prepared by well known procedures. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Antigen-binding fragments of such antibodies may be produced by conventional techniques. Examples of such fragments include, but are not limited to, Fab and F(ab')$_2$ fragments. Antibody fragments and derivatives produced by genetic engineering techniques are also contemplated for use. Unless otherwise specified, the terms "antibody" and "monoclonal antibody" as used herein encompass both whole antibodies and antigen-binding fragments thereof.

Additional embodiments include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993).

A method for producing an antibody comprises immunizing a non-human animal, such as a transgenic mouse, with an IL-4R polypeptide, whereby antibodies directed against the IL-4R polypeptide are generated in said animal. Procedures have been developed for generating human antibodies in non-human animals. The antibodies may be partially human, or preferably completely human. For example, transgenic mice into which genetic material encoding one or more human immunoglobulin chains has been introduced may be employed. Such mice may be genetically altered in a variety of ways. The genetic manipulation may result in human immunoglobulin polypeptide chains replacing endogenous immunoglobulin chains in at least some (preferably virtually all) antibodies produced by the animal upon immunization.

Mice in which one or more endogenous immunoglobulin genes have been inactivated by various means have been prepared. Human immunoglobulin genes have been introduced into the mice to replace the inactivated mouse genes. Antibodies produced in the animals incorporate human immunoglobulin polypeptide chains encoded by the human genetic material introduced into the animal.

Examples of techniques for production and use of such transgenic animals are described in U.S. Pat. Nos. 5,814,318, 5,569,825, and 5,545,806, which are incorporated by reference herein. Examples 2-4 below provide further description of the preparation of transgenic mice useful for generating human antibodies directed against an antigen of interest.

Antibodies produced by immunizing transgenic non-human animals with an IL-4R polypeptide are provided herein. Transgenic mice into which genetic material encoding human immunoglobulin polypeptide chain(s) has been introduced are among the suitable transgenic animals. Examples of such mice include, but are not limited to, those containing the genetic alterations described in the examples below. One example of a suitable immunogen is a soluble human IL-4R, such as a polypeptide comprising the extracellular domain of the protein of SEQ ID NO:2, or other immunogenic fragment of the protein of SEQ ID NO:2.

Monoclonal antibodies may be produced by conventional procedures, e.g., by immortalizing spleen cells harvested from the transgenic animal after completion of the immunization schedule. The spleen cells may be fused with myeloma cells to produce hybridomas, by conventional procedures.

A method for producing a hybridoma cell line comprises immunizing such a transgenic animal with an IL-4R immunogen; harvesting spleen cells from the immunized animal; fusing the harvested spleen cells to a myeloma cell line, thereby generating hybridoma cells; and identifying a hybridoma cell line that produces a monoclonal antibody that binds an IL-4R polypeptide. Such hybridoma cell lines, and anti-IL-4R monoclonal antibodies produced therefrom, are encompassed by the present invention. Monoclonal antibodies secreted by the hybridoma cell line are purified by conventional techniques. Hybridomas or MAbs may be further screened to identify MAbs with particular properties, such as the ability to block an IL-4-induced activity, and to block an IL-13-induced activity (see the assay in example 5).

Human antibodies that bind IL-4R are provided by the present invention. In one embodiment of the invention, human antibodies raised against IL-4R and produced by techniques involving use of transgenic mice, block binding of IL-4 and also IL-13 to cells. Such antibodies are IL-4 antagonists and additionally function as IL-13 antagonists.

Among the uses of antibodies directed against an IL-4R is use in assays to detect the presence of IL-4R polypeptides, either in vitro or in vivo. The antibodies also may be employed in purifying IL-4R proteins by immunoaffinity chromatography. Those antibodies that additionally can block binding of IL-4 to IL-4R may be used to inhibit a biological activity that results from such binding. Blocking antibodies find use in the methods of the present invention. Such antibodies which function as IL-4 antagonists may be employed in treating any IL-4-induced condition, including but not limited to asthma and allergies, e.g., allergic rhinitis, contact dermatitis, and atopic dermatitis. In one embodiment, a human anti-IL-4R monoclonal antibody generated by procedures involving immunization of transgenic mice is employed in treating such conditions.

Antibodies may be employed in an in vitro procedure, or administered in vivo to inhibit an IL-4-induced biological activity. Disorders caused or exacerbated (directly or indirectly) by the interaction of IL-4 with cell surface IL-4 receptors thus may be treated. A therapeutic method involves in vivo administration of a blocking antibody to a mammal in an amount effective for reducing an IL-4-induced biological activity.

Antibodies of the invention include, but are not limited to, partially human (preferably fully human) monoclonal antibodies that inhibit a biological activity of IL-4 and also inhibit a biological activity of IL-13. One embodiment is directed to a human monoclonal antibody that at least partially blocks binding of IL-4 to a cell, and at least partially blocks binding of IL-13 to a cell.

Antibodies of the present invention include but are not limited to antibodies generated by immunizing a transgenic mouse with an IL-4 receptor immunogen, wherein the transgenic mouse is selected from the mouse strains described in example 3 below. The desired antibodies are at least partially human, and preferably fully human. In one embodiment, the immunogen is a human IL-4 receptor polypeptide. Hybridoma cell lines derived from the thus-immunized mice, wherein the hybridoma secretes a monoclonal antibody that binds IL-4R, also are provided herein. Examples of antibodies produced by immunizing such transgenic mice are the human monoclonal antibodies designated 6-2 (described in example 6); 12B5 (described in example 8); and MAbs 63, 1B7, 5A1, and 27A1 (all described in example 9). Monoclonal antibodies 6-2, 12B5, 63, 1B7, 5A1, and 27A1 are fully human antibodies, and are capable of inhibiting activity of both IL-4 and IL-13. MAbs 12B5, 63, and 1B7 are preferred antagonists of human IL-4 and human IL-13.

Particular monoclonal antibodies of the invention are selected from the group consisting of MAb 6-2; a Mab that is cross-reactive with 6-2; a MAb that binds to the same epitope as 6-2; a MAb that competes with 6-2 for binding to a cell that expresses human IL-4R; a MAb that possesses a biological activity of 6-2; and an antigen-binding fragment of any of the foregoing antibodies. In one embodiment, the antibody has a binding affinity for human IL-4R that is substantially equivalent to the binding affinity of 6-2 for human IL-4R. MAb 6-2 is an IgM antibody. MAbs of other isotypes (including but not limited to IgG1 and IgG4), derived from 6-2, also are encompassed by the present invention. Hybridoma cell lines that produce any such monoclonal antibodies also are provided by the present invention.

One example of a biological activity of 6-2 is the ability to function as both an IL-4 antagonist and an IL-13 antagonist. In one embodiment, a MAb of the invention possesses IL-4-blocking activity substantially equivalent to that of 6-2; and possesses IL-13-blocking activity substantially equivalent to that of 6-2. Such activity may be measured in any suitable conventional assay (e.g., as measured in the CD23 expression assay described in example 5).

The DNA sequence of the variable region of the light chain of MAb 6-2 is presented in SEQ ID NO:5, and the encoded amino acid sequence is presented in SEQ ID NO:6. The DNA sequence for the variable region of the heavy chain of MAb 6-2 is presented as SEQ ID NO:7, and the encoded amino acid sequence is presented in SEQ ID NO:8. Antibodies of the present invention include, but are not limited to, monoclonal antibodies that comprise, in their light chain, residues 1 to 107 of SEQ ID NO:6; and antibodies that additionally or alternatively comprise, in their heavy chain, residues 1 to 118 of SEQ ID NO:8.

Complementarity determining regions (CDRs) of a given antibody may be identified using the system described by Kabat et al. in *Sequences of Proteins of Immunological Interest*, 5$^{th}$ Ed., US Dept. of Health and Human Services, PHS, NIH, NIH Publication no. 91-3242, 1991). Particular embodiments of antibodies of the present invention comprise, within the variable region of their light chain, at least one of the complementarity determining regions (CDRs), or hypervariable regions, found in the light chain of 6-2. CDRs of 6-2 are discussed in example 6. Thus, among the antibodies provided herein are those comprising from one to all three of the following sequences in the light chain variable region: amino acid residues 24-35 of SEQ ID NO:6; residues 51-57 of SEQ ID NO:6; and residues 90-97 of SEQ ID NO:6. Particular antibodies provided herein comprise, within the variable region of their heavy chain, at least one of the CDRs found in the heavy chain of 6-2. Thus, among the antibodies provided herein are those comprising from one to all three of the following sequences in the heavy chain variable region: residues 31-35; residues 50-66; and residues 99-107 of SEQ ID NO:8.

Particular monoclonal antibodies of the invention are selected from the group consisting of MAb 12B5; a Mab that is cross-reactive with 12B5; a MAb that binds to the same epitope as 12B5; a MAb that competes with 12B5 for binding to a cell that expresses human IL-4R; a MAb that possesses a biological activity of 12B5; and an antigen-binding fragment of any of the foregoing antibodies. In one embodiment, the antibody has a binding affinity for human IL-4R that is substantially equivalent to the binding affinity of 12B5 for human IL-4R. MAb 12B5 is an IgG1 antibody. MAbs of other isotypes, derived from 12B5, also are encompassed by the present invention. In particular embodiments, the isotype of the MAb is IgG1, IgG4, or IgM. Hybridoma cell lines that produce any such monoclonal antibodies also are provided by the present invention.

One example of a biological activity of 12B5 is the ability to function as both an IL-4 antagonist and an IL-13 antagonist. In one embodiment, a MAb of the invention possesses IL-4-blocking activity substantially equivalent to that of 12B5, and possesses IL-13-blocking activity substantially equivalent to that of 12B5. Such activity may be measured in any suitable conventional assay (e.g., as measured in the CD23 expression assay described in example 5).

IgG4 monoclonal antibodies derived from 12B5 are provided herein. Another embodiment is directed to IgM monoclonal antibodies derived from 12B5. Procedures for switching (altering) the subclass or isotype of an antibody are known in the pertinent field. Such procedures may involve, for example, recombinant DNA technology, whereby DNA encoding antibody polypeptide chains that confer the desired subclass is substituted for DNA encoding the corresponding polypeptide chain of the parent antibody.

The DNA sequence of the variable region of the light chain of MAb 12B5 is presented in SEQ ID NO:9, and the encoded amino acid sequence is presented in SEQ ID NO:10. The DNA sequence for the variable region of the heavy chain of MAb 12B5 is presented as SEQ ID NO:11, and the encoded amino acid sequence is presented in SEQ ID NO:12. Antibodies of the present invention include, but are not limited to, monoclonal antibodies that comprise, in their light chain, residues 1 to 109 of SEQ ID NO:10; and antibodies that additionally or alternatively comprise, in their heavy chain, residues 1 to 115 of SEQ ID NO:12.

Particular embodiments of antibodies of the present invention comprise, within the variable region of their light chain, at least one of the complementarity determining regions (CDRs), or hypervariable regions, found in the light chain of 12B5. CDRs of 12B5 are discussed in example 8. Thus, among the antibodies provided herein are those comprising from one to all three of the following sequences in the light chain variable region: amino acid residues 24-35 of SEQ ID NO:10; residues 51-57 of SEQ ID NO:10; and residues 90-99 of SEQ ID NO:10. Particular antibodies provided herein comprise, within the variable region of their heavy chain, at least one of the CDRs found in the heavy chain of 12B5. Thus, among the antibodies provided herein are those comprising from one to all three of the following sequences in the heavy chain variable region: residues 31-35; residues 50-65; and residues 98-104 of SEQ ID NO:12.

Particular monoclonal antibodies of the invention are selected from the group consisting of MAb 27A1; a Mab that is cross-reactive with 27A1; a MAb that binds to the same epitope as 27A1; a MAb that competes with 27A1 for binding to a cell that expresses human IL-4R; a MAb that possesses a biological activity of 27A1; and an antigen-binding fragment of any of the foregoing antibodies. In one embodiment, the antibody has a binding affinity for human IL-4R that is substantially equivalent to the binding affinity of 27A1 for human IL-4R. 27A1 is an IgG1 antibody. MAbs of other isotypes, derived from 27A1, also are encompassed by the present invention. Hybridoma cell lines that produce any such monoclonal antibodies also are provided by the present invention.

One example of a biological activity of 27A1 is the ability to function as both an IL-4 antagonist and an IL-13 antagonist. In one embodiment, a MAb of the invention possesses IL-4-blocking activity substantially equivalent to that of 27A1; and possesses IL-13-blocking activity substantially equivalent to that of 27A1. Such activity may be measured in any suitable conventional assay (e.g., as measured in the CD23 expression assay described in example 5).

The DNA sequence of the variable region of the light chain of MAb 27A1 is presented in SEQ ID NO:13, and the encoded amino acid sequence is presented in SEQ ID NO:14. The DNA sequence for the variable region of the heavy chain of MAb 27A1 is presented as SEQ ID NO:15, and the encoded amino acid sequence is presented in SEQ ID NO:16. Antibodies of the present invention include, but are not limited to, monoclonal antibodies that comprise, in their light chain, residues 1 to 109 of SEQ ID NO:14; and antibodies that additionally or alternatively comprise, in their heavy chain, residues 1 to 116 of SEQ ID NO:16.

Particular embodiments of antibodies of the present invention comprise, within the variable region of their light chain, at least one of the complementarity determining regions (CDRs), or hypervariable regions, found in the light chain of 27A1. CDRs of 27A1 are discussed in example 9. Thus, among the antibodies provided herein are those comprising from one to all three of the following sequences in the light chain variable region: amino acid residues 24-35 of SEQ ID NO:14; residues 51-57 of SEQ ID NO:14; and residues 90-99 of SEQ ID NO:14. Particular antibodies provided herein comprise, within the variable region of their heavy chain, at least one of the CDRs found in the heavy chain of 27A1. Thus, among the antibodies provided herein are those comprising from one to all three of the following sequences in the heavy chain variable region: residues 31-35; residues 50-66; and residues 99-105 of SEQ ID NO:16.

Particular monoclonal antibodies of the invention are selected from the group consisting of MAb 5A1; a Mab that is cross-reactive with 5A1; a MAb that binds to the same epitope as 5A1; a MAb that competes with 5A1 for binding to a cell that expresses human IL-4R; a MAb that possesses a biological activity of 5A1; and an antigen-binding fragment of any of the foregoing antibodies. In one embodiment, the antibody has a binding affinity for human IL-4R that is substantially equivalent to the binding affinity of 5A1 for human IL-4R. 5A1 is an IgG1 antibody. MAbs of other isotypes, derived from 5A1, also are encompassed by the present invention. Hybridoma cell lines that produce any such monoclonal antibodies also are provided by the present invention.

One example of a biological activity of 5A1 is the ability to function as both an IL-4 antagonist and an IL-13 antagonist. In one embodiment, a MAb of the invention possesses IL-4-blocking activity substantially equivalent to that of 5A1; and possesses IL-13-blocking activity substantially equivalent to that of 5A1. Such activity may be measured in any suitable conventional assay (e.g., as measured in the CD23 expression assay described in example 5).

The DNA sequence of the variable region of the light chain of MAb 5A1 is presented in SEQ ID NO:17, and the encoded amino acid sequence is presented in SEQ ID NO:18. The DNA sequence for the variable region of the heavy chain of MAb 5A1 is presented as SEQ ID NO:19, and the encoded amino acid sequence is presented in SEQ ID NO:20. Antibodies of the present invention include, but are not limited to, monoclonal antibodies that comprise, in their light chain, residues 1 to 107 of SEQ ID NO:18; and antibodies that additionally or alternatively comprise, in their heavy chain, residues 1 to 123 of SEQ ID NO:20.

Particular embodiments of antibodies of the present invention comprise, within the variable region of their light chain, at least one of the complementarity determining regions (CDRs), or hypervariable regions, found in the light chain of 5A1. CDRs of 5A1 are discussed in example 9. Thus, among the antibodies provided herein are those comprising from one to all three of the following sequences in the light chain variable region: amino acid residues 24-34 of SEQ ID NO:18; residues 50-56 of SEQ ID NO:18; and residues 89-97 of SEQ ID NO:18. Particular antibodies provided herein comprise, within the variable region of their heavy chain, at least one of the CDRs found in the heavy chain of 5A1. Thus, among the antibodies provided herein are those comprising from one to all three of the following sequences in the heavy chain variable region: residues 31-35; residues 50-65; and residues 98-112 of SEQ ID NO:20.

Particular monoclonal antibodies of the invention are selected from the group consisting of MAb 63; a Mab that is cross-reactive with MAb 63; a MAb that binds to the same epitope as 63; a MAb that competes with 63 for binding to a cell that expresses human IL-4R; a MAb that possesses a biological activity of 63; and an antigen-binding fragment of any of the foregoing antibodies. In one embodiment, the antibody has a binding affinity for human IL-4R that is substantially equivalent to the binding affinity of 63 for human IL-4R. MAb 63 is an IgM antibody. MAbs of other isotypes, derived from 63, also are encompassed by the present invention. Hybridoma cell lines that produce any such monoclonal antibodies also are provided by the present invention.

One example of a biological activity of 63 is the ability to function as both an IL-4 antagonist and an IL-13 antagonist. In one embodiment, a MAb of the invention possesses IL-4-blocking activity substantially equivalent to that of 63; and possesses IL-13-blocking activity substantially equivalent to that of 63. Such activity may be measured in any suitable conventional assay (e.g., as measured in the CD23 expression assay described in example 5).

The DNA sequence of the variable region of the light chain of MAb 63 is presented in SEQ ID NO:21, and the encoded amino acid sequence is presented in SEQ ID NO:22. The DNA sequence for the variable region of the heavy chain of MAb 63 is presented as SEQ ID NO:23, and the encoded amino acid sequence is presented in SEQ ID NO:24. Antibodies of the present invention include, but are not limited to, monoclonal antibodies that comprise, in their light chain, residues 1 to 107 of SEQ ID NO:22; and antibodies that additionally or alternatively comprise, in their heavy chain, residues 1 to 117 of SEQ ID NO:24.

Particular embodiments of antibodies of the present invention comprise, within the variable region of their light chain, at least one of the complementarity determining regions (CDRs), or hypervariable regions, found in the light chain of 63. CDRs of 63 are discussed in example 9. Thus, among the antibodies provided herein are those comprising from one to all three of the following sequences in the light chain variable region: amino acid residues 24-34 of SEQ ID NO:22; residues 50-56 of SEQ ID NO:22; and residues 89-97 of SEQ ID NO:22. Particular antibodies provided herein comprise, within the variable region of their heavy chain, at least one of the CDRs found in the heavy chain of 63. Thus, among the antibodies provided herein are those comprising from one to all three of the following sequences in the heavy chain variable region: residues 31-35; residues 50-66; and residues 99-106 of SEQ ID NO:24.

Particular monoclonal antibodies of the invention are selected from the group consisting of MAb 1B7; a Mab that is cross-reactive with 1B7; a MAb that binds to the same epitope as 1B7; a MAb that competes with 1B7 for binding to a cell that expresses human IL-4R; a MAb that possesses a biological activity of 1B7; and an antigen-binding fragment of any of the foregoing antibodies. In one embodiment, the antibody has a binding affinity for human IL-4R that is substantially equivalent to the binding affinity of 1B7 for human IL-4R. MAbs of other isotypes, derived from 1B7, also are encompassed by the present invention. Hybridoma cell lines that produce any such monoclonal antibodies also are provided by the present invention.

One example of a biological activity of 1B7 is the ability to function as both an IL-4 antagonist and an IL-13 antagonist. In one embodiment, a MAb of the invention possesses IL-4-blocking activity substantially equivalent to that of 1B7; and possesses IL-13-blocking activity substantially equivalent to that of 1B7. Such activity may be measured in any suitable conventional assay (e.g., as measured in the CD23 expression assay described in example 5).

MAb 1B7 was derived from MAb 63. The amino acid sequence of the heavy chain of MAb 1B7 is identical to that of MAb 63. The only differences between the two antibodies are in the light chain. The DNA sequence of the variable region of the light chain of MAb 1B7 is presented in SEQ ID NO:25, and the encoded amino acid sequence is presented in SEQ ID NO:26. The DNA sequence for the variable region of the heavy chain of MAb 1B7 is presented as SEQ ID NO:23, and the encoded amino acid sequence is presented in SEQ ID NO:24 (same as for MAb 63). Antibodies of the present invention include, but are not limited to, monoclonal antibodies that comprise, in their light chain, residues 1 to 107 of SEQ ID NO:26; and antibodies that additionally or alternatively comprise, in their heavy chain, residues 1 to 117 of SEQ ID NO:24.

Particular embodiments of antibodies of the present invention comprise, within the variable region of their light chain, at least one of the complementarity determining regions (CDRs), or hypervariable regions, found in the light chain of 1B7. CDRs of 1B7 are discussed in example 9. Thus, among the antibodies provided herein are those comprising from one to all three of the following sequences in the light chain variable region: amino acid residues 24-34 of SEQ ID NO:26; residues 50-56 of SEQ ID NO:26; and residues 89-97 of SEQ ID NO:26. Particular antibodies provided herein comprise, within the variable region of their heavy chain, at least one of the CDRs found in the heavy chain of 1B7. Thus, among the antibodies provided herein are those comprising from one to all three of the following sequences in the heavy chain variable region: residues 31-35; residues 50-66; and residues 99-106 of SEQ ID NO:24.

Derivatives of monoclonal antibodies directed against IL-4R may be prepared, and screened for desired properties, by any of a number of known techniques. Certain of the techniques involve isolating DNA encoding a polypeptide chain (or portion thereof) of a MAb of interest, and manipulating the DNA through recombinant DNA technology. The DNA may be fused to another DNA of interest, or altered (e.g., by mutagenesis or other conventional techniques) to add, delete, or substitute one or more amino acid residues, for example.

DNA encoding antibody polypeptides (e.g., heavy or light chain, variable region only or full length) may be isolated from B-cells of mice that have been immunized with IL-4R. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Single chain antibodies may be formed by linking heavy and light chain variable region (Fv region) fragments via an amino acid bridge (short peptide linker), resulting in a single polypeptide chain. Such single-chain Fvs (scFvs) have been prepared by fusing DNA encoding a peptide linker between DNAs encoding the two variable region polypeptides ($V_L$ and $V_H$). The resulting antibody fragments can form dimers or trimers, depending on the length of a flexible linker between the two variable domains (Kortt et al., *Protein Engineering* 10:423, 1997). Techniques developed for the production of single chain antibodies include those described in U.S. Pat. No. 4,946,778; Bird (*Science* 242:423, 1988); Huston et al. (*Proc. Natl. Acad. Sci. USA* 85:5879, 1988); and Ward et al. (*Nature* 334:544, 1989). Single chain antibodies derived from antibodies provided herein (including but not limited to scFvs derived from MAbs 6-2, 12B5, 63, 1B7, 5A1, and 27A1) are encompassed by the present invention.

Techniques are known for deriving an antibody of a different subclass or isotype from an antibody of interest, i.e., subclass switching. Thus, IgG1 or IgG4 monoclonal antibodies may be derived from an IgM monoclonal antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant region of an antibody of the desired isotype.

In particular embodiments, antibodies raised against IL-4R have a binding affinity (Ka) for IL-4R of at least $1 \times 10^8$. In other embodiments, the antibodies exhibit a Ka of at least $1 \times 10^9$ or at least $1 \times 10^{10}$.

PEGylated derivatives of antibodies (modified with polyethylene glycol) also are contemplated, and may be prepared by conventional techniques. Also provided herein are conjugates comprising a detectable (e.g., diagnostic) or therapeutic agent, attached to an antibody directed against IL-4R. Examples of such agents are well known, and include but are not limited to diagnostic radionuclides, therapeutic radionuclides, and cytotoxic drugs. The conjugates find use in in vitro or in vivo procedures.

Particular embodiments of the invention are directed to novel nucleic acid molecules and polypeptides. DNA and amino acid sequence information has been determined for polypeptides that are components of certain antibodies of the present invention, as discussed in examples 6, 8, and 9 below. Among the nucleic acids of the present invention is isolated DNA comprising a nucleotide sequence selected from the group consisting of the nucleotide sequence presented in SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, and SEQ ID NO:25. Among the polypeptides of the present invention is a purified polypeptide comprising an amino acid sequence selected from the group consisting of the amino acid sequence presented in SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26. For in vivo use, the polypeptides advantageously are purified. A polypeptide may be purified individually, or in the form of a purified antibody of which the polypeptide is a component.

Further examples of IL-4 antagonists are antibodies that bind IL-4 and inhibit the binding of IL-4 to cell surface receptors. Such antibodies may be prepared, and screened to identify those that are blocking antibodies, by conventional procedures. Antigen-binding fragments of such antibodies find use as antagonists, as do humanized or genetically engineered derivatives thereof.

Examples of procedures for preparing antibodies directed against human IL-4 (including monoclonal antibodies), assays by which blocking antibodies are identified, and techniques for generating humanized or genetically engineered derivatives of anti-IL-4 antibodies, are described in U.S. Pat. Nos. 5,041,381, 5,863,537, 5,928,904, and 5,676,940, which are hereby incorporated by reference. Further examples of antibodies that may be employed as IL-4 antagonists are described in WO 91/09059, also incorporated by reference herein.

Other Antagonists

Any compound that functions as an IL-4 antagonist and is suitable for administration in accordance with the methods of the present invention may be employed. Antagonists need not completely abolish IL-4-induced biological activity to be useful. Rather, a given antagonist may reduce a biological activity of IL-4.

Derivatives, mutants/muteins, and other variants of IL-4 that function as IL-4 antagonists may be employed. Peptides (which may or may not be muteins) derived from IL-4 that bind to an IL-4R without inducing transduction of a biological signal find use herein. Such peptides function as inert blockers, interfering with the binding of biologically active endogenous IL-4 to cell surface receptors. IL-4-induced signal transduction thereby is inhibited. Muteins or other antagonists that induce a biological response at a reduced level or to a lesser degree, compared to the response induced by native IL-4, also find use as IL-4 antagonists.

Further examples of IL-4 antagonists, including IL-4 muteins, and procedures for preparation thereof are described in Muller et al., *J. Mol. Biol.*, 237:423-436, 1994; U.S. Pat. No. 6,028,176, and U.S. Pat. No. 5,723,118, which are each incorporated by reference herein.

Other options are antisense molecules (oligonucleotides) that inhibit expression of IL-4. Alternatively, the antisense molecule may suppress expression of other molecules involved in IL-4-induced signal transduction.

Any suitable assay, including in vitro assays, can be utilized to determine whether a given compound inhibits an IL-4-induced biological activity. An antagonist may be assayed for the ability to inhibit $^3$H-thymidine incorporation in cells that normally proliferate in response to IL-4.

An alternative involves use of conventional binding assay techniques to test an antagonist for the ability to inhibit binding of IL-4 to cells expressing native or recombinant IL-4 receptors. For use in such assays, recombinant human IL-4 can be expressed and purified as described in U.S. Pat. No. 5,017,691, hereby incorporated by reference herein, or in Park et al., *J. Exp. Med.* 166:476 (1987). The purified protein may be labeled with a detectable agent (e.g., radiolabeled) by any of a number of conventional techniques. A commercially available enzymobead radioiodination reagent (BioRad) may be employed in radiolabeling IL-4 with $^{125}$I for example.

The ability of an IL-4 antagonist to inhibit IL-4-induced damage to epithelium, such as lung epithelium or intestinal epithelium (which may result in loss of barrier function), may be confirmed in any of a number of suitable assays. Among the suitable assay techniques are those described in example 7 below.

Therapeutic Methods and Administration of Antagonists

Methods provided herein comprise administering an IL-4 antagonist to a patient, thereby reducing an IL-4-induced biological response that plays a role in a particular condition. In particular embodiments, methods of the invention involve contacting endogenous IL-4 with an IL-4 antagonist, e.g., in an ex vivo procedure.

Treatment encompasses alleviation of at least one symptom of a disorder, or reduction of disease severity, and the like. An antagonist need not effect a complete "cure", or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. One embodiment of the invention is directed to a method comprising administering to a patient an IL-4 antagonist in an amount and for a time sufficient to induce a sustained improvement over baseline of an indicator that reflects the severity of the particular disorder.

Antibodies that inhibit the binding of both IL-4 and IL-13 to cells are discussed herein. A method for suppressing IL-4-induced and IL-13-induced activities in humans comprises administering an effective amount of such an antibody. Conditions induced by IL-4 or by IL-13, or by both cytokines, thus may be treated.

As is understood in the pertinent field, antagonists are administered to a patient in a manner appropriate to the indication. Antagonists may be administered by any suitable technique, including but not limited to parenterally, topically, or by inhalation. If injected, the antagonist can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of IL-4 antagonists in ex vivo procedures is contemplated. For example, a patient's blood (bodily fluid containing IL-4) may be contacted with an antagonist that binds IL-4 ex vivo, thereby reducing the amount of IL-4 in the fluid when returned to the patient. The antagonist may be bound to a suitable insoluble matrix or solid support material.

Advantageously, antagonists are administered in the form of a composition comprising at least one IL-4 antagonist and one or more additional components such as a physiologically acceptable carrier, excipient or diluent. The present invention provides such compositions comprising an effective amount of an IL-4 antagonist, for use in the methods provided herein.

The compositions contain antagonist(s) in any of the forms described herein. The antagonist may be a whole antibody or an antigen-binding fragment or engineered derivative thereof, for example. For compositions containing an IL-4 receptor, the receptor may be any of the fragments, variants, or oligomers of the protein of SEQ ID NO:2 described herein, for example.

Compositions may, for example, comprise an antagonist together with a buffer, antioxidant such as ascorbic acid, low molecular weight polypeptide (such as those having fewer than 10 amino acids), protein, amino acid, carbohydrate such as glucose, sucrose or dextrins, chelating agents such as EDTA, glutathione, and other stabilizers and excipients. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in *Remington's Pharmaceutical Sciences,* 16$^{th}$ Ed., Mack Publishing Company, Easton, Pa., 1980.

Kits for use by medical practitioners include an IL-4 antagonist and a label or other instructions for use in treating any of the conditions discussed herein. The kit preferably includes a sterile preparation of one or more IL-4 antagonists, which may be in the form of a composition as disclosed above, and may be in one or more vials.

Dosages and the frequency of administration may vary according to such factors as the route of administration, the particular antagonist employed, the nature and severity of the disease to be treated, whether the condition is acute or chronic, and the size and general condition of the patient. Appropriate dosages can be determined by procedures known in the pertinent art, e.g. in clinical trials that may involve dose escalation studies.

An antagonist may be administered once, or repeatedly. In particular embodiments, the antagonist is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antagonist is administered until the patient manifests a medically relevant degree of improvement over baseline for the chosen indicator or indicators.

Particular embodiments of the present invention involve administering an antagonist at a dosage of from about 1 ng/kg/day to about 10 mg/kg/day, more preferably from about 500 ng/kg/day to about 5 mg/kg/day, and most preferably from about 5 ug/kg/day to about 2 mg/kg/day, to a patient. In additional embodiments, an antagonist such as a soluble human IL-4R polypeptide is administered to adults one time per week, two times per week, or three or more times per week, to treat the medical disorders disclosed herein. If injected, the effective amount of antagonist per adult dose may range from 1-20 mg/m$^2$, and preferably is about 5-12 mg/m$^2$. Alternatively, a flat dose may be administered; the amount may range from 5-100 mg/dose. One range for a flat dose is about 20-30 mg per dose. In one embodiment of the invention, a flat dose of 25 mg/dose is repeatedly administered by injection. If a route of administration other than injection is used, the dose is appropriately adjusted in accordance with standard medical practices. One example of a therapeutic regimen involves injecting a dose of about 20-30 mg of IL-4R or other antagonist one to three times per week over a period of at least three weeks, though treatment for longer periods may be necessary to induce the desired degree of improvement. For pediatric patients (age 4-17), one suitable regimen involves the subcutaneous injection of 0.4 mg/kg, up to a maximum dose of 25 mg of IL-4R, administered two or three times per week.

Particular embodiments of the methods provided herein involve subcutaneous injection of from 0.5 mg to 10 mg, preferably from 3 to 5 mg, of a soluble IL-4R, once or twice per week. Another embodiment is directed to pulmonary administration (e.g., by nebulizer) of 3 or more mg of a soluble IL-4R once a week.

Examples of therapeutic regimens provided herein comprise subcutaneous injection of a soluble human IL-4R once a week, at a dose of 1.5 to 3 mg, to treat pulmonary sarcoidosis, minimal change nephrosis, autoimmune uveitis, sickle cell crisis, Churg-Strauss syndrome, Sjogren's syndrome, autoimmune lymphoproliferative syndrome, pre-eclampsia, autoimmune hemolytic anemia, Barrett's esophagus, Grave's Disease, Kawasaki Disease, and cavitary buberculosis. Weekly administration of IL-4R is continued until symptoms subside. Treatment may resume as needed, or, alternatively, maintenance doses may be administered.

An antagonist is administered to the patient in an amount and for a time sufficient to induce an improvement, preferably a sustained improvement, in at least one indicator that reflects the severity of the disorder that is being treated. Various indicators that reflect the extent of the patient's illness may be assessed for determining whether the amount and time of the treatment is sufficient. Such indicators include, for example, clinically recognized indicators of disease severity, symptoms, or manifestations of the disorder in question. In most instances, an improvement is considered to be sustained if the patient exhibits the improvement on at least two occasions separated by two to four weeks. The degree of improvement generally is determined by the patient's physician, who may make this determination based on signs or symptoms, and who may also employ questionnaires that are administered to the patient, such as quality-of-life questionnaires developed for a given disease.

As one example, in treating benign prostate hyperplasia, an IL-4 inhibitor is administered to the patient in an amount and for a time effective in scar regression or complete healing. Maintenance doses may be given or treatment resumed as needed.

Elevated levels of IL-4 are associated with a number of disorders, as discussed above. Patients with a given disorder may be screened, to identify those individuals who have elevated IL-4 levels, or to identify those with an elevated TH2-type immune response, thereby identifying the patients who may benefit most from treatment with an IL-4 antagonist. Thus, treatment methods provided herein optionally comprise a first step of measuring a patient's IL-4 level. An IL-4 antagonist may be administered to a patient in whom IL-4 levels are elevated above normal. Alternatively or additionally, a patient may be pre-screened to determine whether the patient has an elevated TH2-type immune response, prior to administration of antagonist(s) against one or more TH2-type cytokines.

A patient's levels of IL-4 (and, optionally, of other TH2-type cytokines) may be monitored during and/or after treatment with an IL-4 antagonist, to detect reduction in the levels of the cytokines. For some disorders, the incidence of elevated IL-4 levels, and the balance between TH1-type and TH2-type immune responses, may vary according to such factors as the stage of the disease or the particular form of the disease. Known techniques may be employed for measuring IL-4 levels, e.g., in a patient's serum, and for assessing TH2-type immune responses. Cytokine levels in blood samples may be measured by ELISA, for example.

Particular embodiments of methods and compositions of the invention involve the use of two or more different IL-4 antagonists. In further embodiments, IL-4 antagonist(s) are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but include treatment regimens in which an IL-4 antagonist is administered at least once during a course of treatment that involves administering at least one other therapeutic agent to the patient.

Examples of other agents that may be co-administered with IL-4 antagonists are other antibodies, cytokines, or cytokine receptors, which are chosen according to the particular condition to be treated. Alternatively, non-proteinaceous drugs that are useful in treating one of the particular conditions discussed above may be co-administered with an IL-4 antagonist.

For treating IgE-mediated conditions, an IL-4 antagonist may be co-administered with an IgE antagonist. One example is an anti-IgE antibody. Humanized anti-IgE monoclonal antibodies are described in Presta et al. (*J. Immunol.* 151(5): 2623-2632, 1993) and Adelroth et al. (*J. Allergy Clin. Immunol.* 106(2):253-259, 2000), for example.

IL-4 antagonists may be co-administered with an IL-5 antagonist, which may be a molecule that interferes with the binding of IL-5 to an IL-5 receptor, such as an anti-IL-5 antibody (e.g., a human or humanized anti-IL-5 monoclonal antibody), or a receptor such as a soluble human IL-5 receptor polypeptide. IL-5 has been implicated as playing a role in mediating allergic responses. Thus, administration of antagonist(s) of IL-4 and IL-5 is contemplated for treatment of allergic reactions, including but not limited to allergic asthma.

IL-4 antagonists may be employed in conjunction with other agent(s) in treating the particular IL-4-induced conditions discussed above. For example, drugs currently employed in treating the conditions may be co-administered with one or more IL-4 antagonists.

For treating asthma, an IL-4 antagonist may be co-administered with other anti-asthma medications, such as inhaled corticosteroids, beta agonists, leukotriene antagonists, xanthines, fluticasone, salmeterol, albuterol, non-steroidal agents such as cromolyn, and the like. IL-4 antagonists may be co-administered with other anti-allergy medications to treat allergic reactions.

One embodiment of the present invention is directed to co-administration of an IL-4 antagonist (such as a soluble human IL-4R) and fluticasone and salmeterol to treat a disorder such as asthma. Compositions comprising an IL-4 inhibitor (e.g., soluble human IL-4R), fluticasone, and salmeterol are provided herein. Advair Diskus (Glaxo Wellcome) comprises fluticasone propionate and salmeterol xinafoate. For treating asthma, Advair Diskus and the IL-4 antagonist preferably are delivered by inhalation.

Another example of combination therapy comprises co-administration of an IL-4 antagonist and an IL-9 antagonist to a patient who has asthma. Any suitable IL-9 antagonist may be employed, such as an IL-9 receptor (preferably a soluble form thereof), an antibody that interferes with binding of IL-9 to a cell surface receptor (wherein the antibody may be raised against IL-9 or an IL-9 receptor polypeptide), or another compound that inhibits IL-9-induced biological activity. IL-9 receptors include those described in WO 93/18047 and U.S. Pat. Nos. 5,789,237 and 5,962,269, which are hereby incorporated by reference herein.

In an additional embodiment of combination therapy, a method for treating ulcerative colitis comprises co-administration of at least one IL-4 antagonist and at least one IL-1 antagonist. Examples of IL-1 antagonists include type I IL-1 receptor, type II IL-1 receptor, IL-1 receptor antagonist (IL-1Ra), antagonistic (blocking) antibodies directed against IL-1, and antagonistic antibodies directed against an IL-1 receptor. Various forms of the receptors may be employed, such as fragments, variants and fusions analogous to those described above for IL-4 receptor. A preferred IL-1 antagonist is a soluble form of type II IL-1 receptor, which is described in U.S. Pat. No. 5,350,683, hereby incorporated by reference herein.

One method of the present invention comprises co-administering IL-4 antagonist(s) and IL-13 antagonist(s) to a patient who has minimal change nephrosis. Alternative embodiments involve administering IL-4 antagonist(s) alone, or IL-13 antagonist(s) alone, to a minimal change nephrosis patient. The IL-4 antagonists(s) and/or IL-13 antagonist(s) may be administered to reduce severity of the disease.

Another method provided herein is a method for treating various allergic inflammatory conditions, comprising co-administering IL-4 antagonist(s) and IL-13 antagonist(s). Conditions such as asthma, allergies, and chronic lung diseases such as cystic fibrosis and chronic obstructive pulmonary disease are treated by such a method.

Any suitable IL-13 antagonist may be employed, including but not limited to IL-13 receptors (preferably soluble forms thereof), IL-13 receptor antagonists, antibodies directed against IL-13 or an IL-13 receptor, other proteins that interfere with the binding of IL-13 to an IL-13 receptor, and compounds that inhibit IL-13-mediated signal transduction. IL-13 receptors and heterodimers comprising IL-13R polypeptides as components thereof are described above. Antibodies that are raised against IL-4R may be screened for the ability to also function as IL-13 antagonists, as discussed above.

A method for treating or preventing a condition characterized by reduced epithelial barrier function comprises co-administering IL-4 antagonist(s) and one or more IL-13 antagonists. Such conditions are discussed above. In one embodiment, the condition is asthma. Particular embodiments are directed to co-administering one or more IL-4 antagonists and one or more IL-13 antagonists to a patient having a condition involving reduction of lung epithelial barrier function or intestinal epithelial barrier function, wherein both IL-4 and IL-13 play a role in the reduced barrier function. The method thus inhibits both IL-4-induced reduction of barrier function and IL-13-induced reduction of barrier function. The adverse effect of IL-13 on lung and intestinal epithelial barrier function can be confirmed using assay techniques such as those described in example 7 below. (See also Zund et al., *J. Biol. Chem.* 271(13):7460-7464, 1996.)

Another method provided herein comprises co-administering IL-4 antagonist(s) and interferon-γ (IFN-γ) to a patient having a condition involving reduction of lung epithelial barrier function. Optionally, such a method further comprises co-administering one or more IL-13 antagonists to the patient (i.e., co-administering an IL-4 antagonist, IFN-γ, and an IL-13 antagonist). Other methods comprise administering IFN-γ as a single agent, or co-administering IFN-γ and an IL-13 antagonist, to a patient having a condition involving reduction of lung epithelial barrier function. In one embodiment, the patient has asthma. For treating asthma, the IL-4 antagonist, IFN-γ, and/or IL-13 antagonist preferably are administered by inhalation.

One method provided herein for treating asthma comprises administering an IL-4 antagonist and interferon-γ to a human who has asthma. Another method for treating asthma comprises co-administering an IL-4 antagonist, IFN-γ, and an IL-13 antagonist to a human who has asthma. In one embodiment, IFN-γ is co-administered to an asthmatic, together with an antibody that functions as an antagonist of both IL-4 and IL-13. Such antibodies are described elsewhere herein.

A single agent may function as an IL-4 antagonist and an IL-13 antagonist, as discussed above. As an example of such an agent, some antibodies raised against IL-4Rα may interfere with the binding of both IL-4 and IL-13 receptor complexes, due to the shared IL-4Rα component in such multi-subunit receptor complexes (discussed above). Thus, a single agent may be employed in a method for inhibiting reduction of barrier function.

Antagonists may be co-administered with one or more leukotriene receptor antagonists to treat disorders such as allergic inflammatory diseases, e.g., asthma and allergies. Examples of leukotriene receptor antagonists include but are not limited to montelukast, pranlukast, and zafirlukast. Drugs that function as 5-lipoxygenase inhibitors may be co-administered with an IL-4 antagonist to treat asthma.

Methods provided herein comprise administering one or more of the following to Churg-Strauss Syndrome patients: IL-4 antagonist(s), IL-5 antagonist(s), IL-13 antagonist(s) or IgE antagonist(s). One example of such a method involves co-administering IL-4 antagonist(s) and IL-5 antagonist(s) to a Churg-Strauss Syndrome patient. In another embodiment, IL-4 antagonist(s) and IgE antagonist(s) are co-administered to the patient. In yet another embodiment, IL-4 antagonist(s) and IL-13 antagonist(s) are co-administered to the patient.

The hormone relaxin may be co-administered with an IL-4 antagonist to treat scleroderma (systemic sclerosis), idiopathic pulmonary fibrosis, or any other disorder characterized by pulmonary fibrosis, such as the conditions involving fibrosis of the lung that are discussed above. Recombinant human relaxin is preferred for use in treating humans.

A method for treating benign prostate hyperplasia comprises co-administering IL-4 antagonist(s) and one or more additional anti-inflammatory agents. Examples of agents that inhibit inflammation include tumor necrosis factor (TNF) antagonists and IL-17 antagonists.

Any suitable IL-17 antagonist may be employed, including but not limited to an IL-17 receptor (preferably soluble forms thereof), IL-17 receptor antagonists, antibodies directed against IL-17 or an IL-17 receptor, other proteins that interfere with the binding of IL-17 to an IL-17 receptor, and compounds that inhibit IL-17-mediated signal transduction. An IL-17 receptor, including soluble forms thereof and oligomers thereof, is described in WO 96/29408, hereby incorporated by reference. An alternative method provided herein comprises administering an IL-17 antagonist to treat a patient with benign prostate hyperplasia.

Likewise, any suitable TNF antagonist may be employed, including but not limited to a TNF receptor (preferably soluble forms thereof), fusion proteins comprising a TNF receptor (or comprising the TNF-binding portion of a TNF receptor), TNF receptor antagonists, antibodies directed against TNF or a TNF receptor, other proteins that interfere with the binding of TNF to a TNF receptor, and compounds that inhibit TNF-mediated signal transduction. Further examples of TNF inhibitors are the drugs thalidomide and pentoxyfylline. The TNF receptor protein known as p75 or p80 TNF-R preferably is employed. A preferred TNF antagonist is a soluble human TNF receptor (sTNF-R) in dimeric form, such as dimers of sTNF-R/Fc fusion proteins. One such dimer is etanercept (Enbrel®, Immunex Corporation, Seattle, Wash.). p75/p80 TNF-R, including soluble fragments and other forms thereof, is described in WO 91/03553, hereby incorporated by reference herein.

In accordance with the present invention, an IL-4 antagonist is co-administered with a TNF antagonist to treat any condition in which undesirable IL-4-induced and TNF-induced immune responses play a role, such as inflammation. One method provided herein comprises co-administering an IL-4 antagonist and a TNF antagonist to a patient with inflammatory bowel disease, Crohn's disease, or ulcerative colitis. Other embodiments are directed to a method comprising co-administering an IL-4 antagonist and a TNF antagonist to a patient who has Kawasaki Disease, autoimmune hemolytic anemia, autoimmune uveoretinitis, autoimmune lymphoproliferative syndrome, Sjogren's syndrome, chronic fatigue syndrome, or hepatotoxicity induced by a drug such as diclofenac.

Another method provided herein comprises co-administering an IL-4 antagonist and a TNF antagonist to a pregnant woman who has developed pre-eclampsia. Administration of the IL-4 antagonist and TNF-antagonist preferably continues for the duration of the pregnancy.

Suitable dosages of etanercept (Enbrel®, Immunex Corporation, Seattle, Wash.) will vary according to the nature of the disease to be treated, disease severity, the size of the patient (e.g., adult or child), and other factors, as is recognized in the pertinent field. In one embodiment of the methods provided herein, Enbrel® is administered twice a week by subcutaneous injection at a dose of from 1 to 25 mg. One embodiment of a pediatric dosage is 0.4 mg/kg. Particular methods provided herein comprise co-administration of an IL-4 antagonist and Enbrel® to a patient has autoimmune lymphoproliferative syndrome or Sjogren's syndrome, wherein Enbrel® is given by subcutaneous injection at a dose of from 1 to 25 mg.

For treating graft versus host disease, an IL-4 antagonist is co-administered with at least one of the following agents: a TNF antagonist, an IL-1 antagonist, steroids, or corticosteroids. The TNF inhibitor preferably is Enbrel®. A preferred IL-1 antagonist is a soluble form of type II IL-1 receptor, which is described in U.S. Pat. No. 5,350,683. In one embodiment, the GVHD is associated with (e.g., develops subsequent to) bone marrow transplantation. An IL-4 antagonist may be employed in combination with at least one of the above-listed agents, in methods for suppressing an immune response directed against transplanted cells, tissue, and/or alloantigen.

A number of cytokine antagonists and other agents/drugs are disclosed herein as being useful for combination therapy (e.g., co-administration with an IL-4 antagonist) in treating particular diseases. It is to be understood that such antagonists, agents, or drugs also find use as single agents in treating those diseases. It also is to be understood that disclosure of methods involving administration of an antagonist to a particular cytokine, to treat a disease, encompasses administration of one type of antagonist, and also encompasses administration of two or more different antagonists for that cytokine, unless specified otherwise.

The following examples are offered by way of illustration, and not by way of limitation.

Example 1

Preparation of Monoclonal Antibodies

IL-4 receptor polypeptides may be employed as immunogens in generating monoclonal antibodies by conventional techniques, e.g., techniques described in U.S. Pat. No. 5,599, 905, hereby incorporated by reference. It is recognized that polypeptides in various forms may be employed as immunogens, e.g., full length proteins, fragments thereof, fusion proteins thereof such as Fc fusions, cells expressing the recombinant protein on the cell surface, etc.

To summarize an example of such a procedure, an IL-4R immunogen emulsified in complete Freund's adjuvant is injected subcutaneously into Lewis rats, in amounts ranging from 10-100 µl. Three weeks later, the immunized animals are boosted with additional immunogen emulsified in incomplete Freund's adjuvant and boosted every three weeks thereafter. Serum samples are periodically taken by retro-orbital bleeding or tail-tip excision for testing by dot-blot assay, ELISA (enzyme-linked immunosorbent assay), or inhibition of binding of $^{125}$I-IL-4 to extracts of IL-4R-expressing cells. Following detection of an appropriate antibody titer, positive animals were given a final intravenous injection of antigen in saline. Three to four days later, the animals are sacrificed, splenocytes harvested, and fused to the murine myeloma cell line AG8653. The resulting hybridoma cell lines are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated are screened for reactivity with IL-4R. Initial screening of hybridoma supernatants utilizes an antibody capture and binding of partially purified $^{125}$I-IL-4 receptor. Hybridomas that are positive in this screening method are tested by a modified antibody capture to detect hybridoma cells lines that are producing blocking antibody. Hybridomas that secrete a monoclonal antibody capable of inhibiting $^{125}$I-IL-4 binding to cells expressing IL-4R are thus detected. Such hydridomas then are injected into the peritoneal cavities of nude mice to produce ascites containing high concentrations (>1 mg/ml) of anti-IL-4R monoclonal antibody. The resulting monoclonal antibodies may be purified by ammonium sulfate precipitation followed by gel exclusion chromatography, and/or affinity chromatography based on binding of antibody to Protein G.

Example 2

Generation of Cmu Targeted Mice

This example describes procedures for generating transgenic mice. Additional procedures for generating transgenic mice, and the use of such mice for preparing human antibodies, are described in Examples 3 and 4.

Construction of a CMD Targeting Vector.

The plasmid pICEmu contains an EcoRI/XhoI fragment of the murine Ig heavy chain locus, spanning the mu gene, that was obtained from a Balb/C genomic lambda phage library (Marcu et al. *Cell* 22: 187, 1980). This genomic fragment was subcloned into the XhoI/EcoRI sites of the plasmid pICEMI9H (Marsh et al; *Gene* 32, 481-485, 1984). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in *E. coli*.

The targeting vector was constructed as follows. (See FIGS. 2A-2C, which depict further details.) A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of Cmu1 to the SmaI site located within Cmu1. The resulting plasmid was digested with SmaI/SpeI and the approximately 4 kb SmaI/XbaI fragment from pICEmu, extending from the Sma I site in Cmu1 3' to the XbaI site located just downstream of the last Cmu exon, was inserted. The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al. (1987) *Gene* 60: 65-74) and containing the pgk polyadenylation site (PvuII/HindIII fragment; Boer et al. (1990) *Biochemical Genetics* 28: 299-308). This cassette was obtained from the plasmid pKJ1 (described by Tybulewicz et al. (1991) *Cell* 65: 1153-1163) from which the neo cassette was excised as an EcoRI/HindIII fragment and subcloned into EcoRI/HindIII digested pGEM-7Zf(+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences.

The resulting plasmid was linearized with Not I, and a herpes simplex virus thymidine kinase (tk) cassette was inserted to allow for enrichment of ES clones bearing homologous recombinants, as described by Mansour et al. (1988) *Nature* 336: 348-352. This cassette consists of the coding sequences of the tk gene bracketed by the mouse pgk promoter and polyadenylation site, as described by Tybulewicz et al. (1991) *Cell* 65:1153-1163.

The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.

Generation and Analysis of Targeted ES Cells.

AB-1 ES cells (McMahon, A. P. and Bradley, A., (1990) *Cell* 62: 1073-1085) were grown on mitotically inactive SNL76/7 cell feeder layers (ibid.), essentially as described in *Teratocarcinomas and Embryonic Stem Cells: a Practical Approach*, E. J. Robertson, Ed., Oxford: IRL Press, 1987, pp. 71-112. The linearized CMD targeting vector was electroporated into AB-1 cells by the methods described in Hasty et al. (1991) *Nature* 350: 243-246. Electroporated cells were plated into 100 mm dishes at a density of 1-2×10$^6$ cells/dish. After 24 hours, G418 (200 micrograms/ml of active component) and FIAU (5×10$^{-7}$ M) were added to the medium, and drug-resistant clones were allowed to develop over 8-9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described by Laird et al., (1991) *Nucleic Acids Res.* 19:4293). Isolated genomic DNA was digested with SpeI and probed with a 915 by SacI fragment, probe A (FIG. 2C), which hybridizes to a sequence between the mu intronic enhancer and the mu switch region.

Probe A detects a 9.9 kb SpeI fragment from the wild type locus, and a diagnostic 7.6 kb band from a mu locus which has homologously recombined with the CMD targeting vector (the neo expression cassette contains a SpeI site).

Of 1132 G418 and FIAU resistant clones screened by Southern blot analysis, 3 displayed the 7.6 kb Spe I band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmu1 exon.

Generation of Mice Bearing the Mutated mu Gene.

The three targeted ES clones, designated number 264, 272, and 408, were thawed and injected into C57BL/6J blastocysts as described by A. Bradley in *Teratocarcinomas and Embryonic Stem Cells: a Practical Approach*, E. J. Robertson, Ed., Oxford: IRL Press, 1987, pp. 113-151. Injected blastocysts were transferred into the uteri of pseudopregnant females to generate chimeric mice representing a mixture of cells derived from the input ES cells and the host blastocyst. The extent of ES cell contribution to the chimera can be visually estimated by the amount of agouti coat coloration, derived from the ES cell line, on the black C57BL/6J background. Clones 272 and 408 produced only low percentage chimeras (i.e. low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BglI digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of Transgenic Mice for Functional Inactivation of mu Gene.

To determine whether the insertion of the neo cassette into Cmu1 has inactivated the Ig heavy chain gene, a clone 264 chimera was bred with a mouse homozygous for the JHD mutation, which inactivates heavy chain expression as a result of deletion of the JH gene segments (Chen et al, (1993) *Immunol*. 5: 647-656). Four agouti offspring were generated. Serum was obtained from these animals at the age of 1 month and assayed by ELISA for the presence of murine IgM. Two of the four offspring were completely lacking IgM (Table 1). Genotyping of the four animals by Southern blot analysis of DNA from tail biopsies by BglI digestion and hybridization with probe A (FIG. 2C), and by StuI digestion and hybridization with a 475 by EcoRI/StuI fragment (ibid.) demonstrated that the animals which fail to express serum IgM are those in which one allele of the heavy chain locus carries the JHD mutation, the other allele the Cmu1 mutation. Mice heterozygous for the JHD mutation display wild type levels of serum Ig. These data demonstrate that the Cmu1 mutation inactivates expression of the mu gene.

Table 1 presents the level of serum IgM, detected by ELISA, for mice carrying both the CMD and JHD mutations (CMD/JHD), for mice heterozygous for the JHD mutation (+/JHD), for wild type (129Sv×C57BL/6J)F1 mice (+/+), and for B cell deficient mice homozygous for the JHD mutation (JHD/JHD).

TABLE 1

| Mouse | Serum IgM (micrograms/ml) | Ig H chain genotype |
|---|---|---|
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | <0.002 | JHD/JHD |

Example 3

Generation of Transgenic Mice

The HCo12 Human Heavy Chain Transgene.

The HCo12 transgene was generated by coinjection of the 80 kb insert of pHC2 (Taylor et al., 1994, *Int. Immunol.*, 6: 579-591) and the 25 kb insert of pVx6. The plasmid pVx6 was constructed as described below.

An 8.5 kb HindIII/SalI DNA fragment, comprising the germline human VH1-18 (DP-14) gene together with approximately 2.5 kb of 5' flanking, and 5 kb of 3' flanking genomic sequence was subcloned into the plasmid vector pSP72 (Promega, Madison, Wis.) to generate the plasmid p343.7.16. A 7 kb BamHI/HindIII DNA fragment, comprising the germline human VH5-51 (DP-73) gene together with approximately 5 kb of 5' flanking and 1 kb of 3' flanking genomic sequence, was cloned into the pBR322 based plasmid cloning vector pGP1f (Taylor et al. 1992, *Nucleic Acids Res*. 20: 6287-6295), to generate the plasmid p251f.

A new cloning vector derived from pGP1f, pGP1k (the sequence of which is presented in FIGS. 3A and 3B and SEQ ID NO:4), was digested with EcoRV/BamHI, and ligated to a 10 kb EcoRV/BamHI DNA fragment, comprising the germline human VH3-23 (DP47) gene together with approximately 4 kb of 5' flanking and 5 kb of 3' flanking genomic sequence. The resulting plasmid, p112.2RR.7, was digested with BamHI/SalI and ligated with the the 7 kb purified BamHI/SalI insert of p251f. The resulting plasmid, pVx4, was digested with XhoI and ligated with the 8.5 kb XhoI/SalI insert of p343.7.16. A clone was obtained with the VH1-18 gene in the same orientation as the other two V genes. This clone, designated pVx6, was then digested with NotI and the purified 26 kb insert coinjected, together with the purified 80 kb NotI insert of pHC2 at a 1:1 molar ratio, into the pronuclei of one-half day (C57BL/6J×DBA/2J)F2 embryos as described by Hogan et al. (B. Hogan et al., Manipulating the Mouse Embryo, A Laboratory Manual, $2^{nd}$ edition, 1994, Cold Spring Harbor Laboratory Press, Plainview N.Y.).

Three independent lines of transgenic mice comprising sequences from both Vx6 and HC2 were established from mice that developed from the injected embryos. These lines are designated (HCo12)14881, (HCo12)15083, and (HCo12) 15087. Each of the three lines were then bred with mice comprising the CMD mutation described in Example 2, the JKD mutation (Chen et al. 1993, EMBO J. 12: 811-820), and the (KCo5)9272 transgene (Fishwild et al. 1996, Nature Biotechnology 14: 845-851). The resulting mice express human heavy and kappa light chain transgenes in a background homozygous for disruption of the endogenous mouse heavy and kappa light chain loci.

Additional Transgenic Mouse Strains

Particular strains of mice that may be used to generate IL-4R-reactive monoclonal antibodies are strain ((CMD)++; (JKD)++; (HCo7)11952+/++; (KCo5)9272+/++), and strain ((CMD)++; (JKD)++; (HCo12)15087+/++; (KCo5) 9272+/++). Each of these transgenic strains is homozygous for disruptions of the endogenous heavy chain (CMD) and kappa light chain (JKD) loci. Both strains also comprise a human kappa light chain transgene (HCo7), with individual animals either hemizygous or homozygous for insertion #11952. The two strains differ in the human heavy chain transgene used. Mice were hemizygous or homozygous for either the HCo7 or the HCo12 transgene. The CMD mutation is described above in Example 2. The generation of (HCo12) 15087 mice is described above (in this example). The JKD mutation (Chen et al. 1993, EMBO J. 12: 811-820) and the (KCo5)9272 (Fishwild et al. 1996, Nature Biotechnology 14: 845-851) and (HCo7)11952 mice, are described in U.S. Pat. No. 5,770,429, which is hereby incorporated by reference.

Example 4

Generation of Human Anti-IL-4R Monoclonal Antibodies

Transqenic Mice

Strain ((CMD)++; (JKD)++; (HCo7)11952+/++; (KCo5) 9272+/++ which is homozygous for disruptions of the endogenous heavy chain (CMD) and kappa light chain (JKD) loci (see example 3), was used to generate IL-4R-reactive monoclonal antibodies. This strain also comprises a human kappa light chain transgene (HCo7) with individual animals either hemizygous or homozygous for insertion #11952. Mice were hemizygous or homozygous for the HCo7 transgene. The CMD mutation is described above in Example 2. The JKD mutation (Chen et al. 1993, EMBO J. 12: 811-820) and the (KCo5)9272 (Fishwild et al. 1996, Nature Biotechnology 14: 845-851) and (HCo7)11952 mice, are described in U.S. Pat. No. 5,770,429, which is hereby incorporated by reference.

Immunization.

Transgenic mice were initially immunized i.p. with 25 ug IL-4R protein in adjuvant (Titermax, available from Cytrx Corporation, Norcross, Ga.). The immunogen was a human IL-4R polypeptide comprising the extracellular domain of the protein of SEQ ID NO:2. Immunized mice were subsequently boosted every 4 weeks i.p. with the IL-4R immunogen in incomplete freunds adjuvant. Animals were kept on protocol for 2 to 5 months. Prior to fusion, animals were boosted i.v. on days −4 and −3 with 5 to 8 ug immunogen.

Fusions.

Spleen cells harvested from the immunized mice were fused to mouse myeloma cells NS-1 by standard procedures (Harlow and Lane, 1988, Antibodies, A Laboratory Manual, Cold Spring Harbor Laboratory Press, Cold Spring Harbor New York; Kennett et al. 1980, Monoclonal Antibodies, Hybridomas: A New Dimension in Biological Analysis. Plenum, New York; Oi and Hertzenberg, 1980, Immunoglobulin Producing Hybrid Cell Lines, in Selected Methods In Cellular Immunology, ed. Mishell and Shiigi, pp. 357-372. Freeman, San Francisco). Cells were cultured in DMEM, 10% FBS, OPI (Sigma O-5003), BME (Gibco 21985-023), 3% Origen Hybridoma Cloning Factor (Igen IG50-0615), and 5% P388d1 (ATCC TIB 63) conditioned media. HAT or HT supplement was added to the medium during initial growth and selection.

Hybridoma Screening.

To identify hybridomas secreting human antibodies against the IL-4R, ELISA plates (Nunc MaxiSorp) were coated overnight at 4° C. with 100 ul/well human IL-4R at 2.0 ug/ml in PBS. Plates were washed with 100 ul/well PBS-Tween (PBST) containing 1% BSA. Fifty ul cell culture supernatent was added followed by a 1.0 hour incubation. Plates were washed and then incubated for one hour with 100 ul/well goat anti-human IgG conjugated to horseradish peroxidase (Sigma #A-3813, or #A-7164). Plates were washed three times in PBS-Tween between each step.

Wells that read positive by ELISA were screened for their ability to block the binding of IL-4 to IL-4R. ELISA plates were coated overnight with a non-neutralizing mouse anti-human IL-4R antibody M10 at 2 ug/ml. Plates were washed 3× with PBST. 100 ul human IL-4R was added at 10 ng/ml in PBST and incubated for 1.0 hour. Plates were washed 4× with PBST and 100 ul supernatant samples were added and incubated for 1.0 hour. Wells were washed 4× with PBST. 5.0 ng/ml biotinylated IL-4 was added in PBST and incubated for 1.0 hour. 100 ul/well poly80 horseradish peroxidase (RDI) was added at 1:5000 in PBST and incubated for 45 minutes. Plates were washed 5× with PBST, and a colorimetric reagent (3,3',5,5' tetramethylbenzidine, available from Kirkegaard and Perry) was added at 100 ul/well until color developed. Reaction was stopped with 100 ul phosphoric acid and plates were read at 450 nm. Absent or reduced signal was interpreted as the antibody binding to receptor in a manner that blocked IL-4 from binding to receptor. Wells that appeared to block binding were expanded and tested for IL-4 and IL-13 blocking in a CD23 expression assay (see example 5).

Example 5

Assay for Assessing Blocking Activity

This assay is based on ability of both IL-4 and IL-13 to enhance the expression of the activation-associated surface antigen CD23 on human B cells. Antibodies are tested for the ability to inhibit CD23 expression induced by IL-4 and by IL-13.

Antibodies raised against human IL-4R (huIL-4R) were tested either in the form of hybridoma supernatants or purified protein. Prior to addition to cultures, the antibodies were buffer exchanged against culture medium (RPMI 1640 plus 10% heat-inactivated fetal bovine serum) by centrifugation, using Centricon filter devices (Amicon) with a 10 kDa cutoff.

Human peripheral blood B cells were purified as described previously (Morris et al., *J. Biol. Chem.* 274:418-423, 1999). The B cells ($3 \times 10^5$/well) in culture medium were placed in 96-well round-bottomed microtiter plates and preincubated at room temperature for 30 min with test antibodies at the final concentrations indicated. Recombinant human IL-4 or IL-13 was then added to the cultures at the concentrations indicated, and cells were cultured for 20-24 hours at 37° C. in a humidified atmosphere of 5% $CO_2$. At the end of the culture period, cells were washed once in PBS+0.02% $NaN_3$ in the 96-well culture plate and were resuspended in blocking buffer (2% normal rabbit serum+1% normal goat serum in PBS+$NaN_3$). Phycoerythrin (PE)-conjugated CD23 monoclonal antibody (mAb) or PE-conjugated isotype control mAb (both from Pharmingen) was then added to cells at a final dilution of 1:10. Cells were incubated for 30 minutes at 4° C., washed x3 in PBS+$NaN_3$ and analyzed on a FacScan (Becton Dickinson) for CD23 expression.

In all experiments, negative controls were included which consisted of cells cultured with hybridoma growth medium or isotype-matched non-blocking human anti-hIL-4R antibody. An anti-huIL-4R murine mAb (R&D Systems), previously shown to block the binding and function of both hIL-4 and hIL-13, was used as a positive control for neutralization of CD23 induction by IL-4 and IL-13.

Example 6

Hybridoma Cell Line

One hybridoma cell line generated by procedures described above (see example 4) is designated 6-2. The anti-IL-4R monoclonal antibody secreted by this hybridoma is a blocking antibody, as determined in a conventional plate binding assay, and thus functions as an IL-4 antagonist. The monoclonal antibody produced by 6-2 also exhibits the ability to reduce an IL-13-induced biological activity.

One embodiment of the invention is directed to a hybridoma cell line produced as described above, wherein the hybridoma secretes an isotype IgM MAb directed against human IL-4R. Also provided herein are IgG1 monoclonal antibodies derived from IgM monoclonal antibodies.

The DNA sequence of the variable region of the light chain of MAb 6-2 has been determined, and is presented in SEQ ID NO:5; the amino acid sequence encoded thereby is presented in SEQ ID NO:6. Complementarity determining regions 1 to 3 (CDR 1-3) are believed to correspond to amino acids 24-35, 51-57, and 90-97, of SEQ ID NO:6, respectively.

The DNA sequence of the variable region of the heavy chain of MAb 6-2 has been determined, and is presented in SEQ ID NO:7; the amino acid sequence encoded thereby is presented in SEQ ID NO:8. Complementarity determining regions 1 to 3 (CDR 1-3) are believed to correspond to amino acids 31-35, 50-66, and 99-107 of SEQ ID NO:8, respectively.

Example 7

Assays for Measuring Loss of Barrier Function

A method provided herein involves use of IL-4 antagonists to inhibit IL-4-induced damage to epithelium, including but not limited to lung epithelium or intestinal epithelium. Damage to epithelium can result in loss of barrier function. A number of techniques are known for determining whether an epithelial layer is intact. The following are examples of techniques that may be employed in assessing the ability of an IL-4 antagonist to inhibit IL-4-induced damage to epithelium and loss of epithelial barrier function.

Cells that may be employed in preparing in vitro models of epithelium (epithelial barriers) are known. For example, Calu-3 human lung epithelial cells are suitable for use in barrier function studies. Another suitable cell line is the human intestinal epithelial cell line designated T84. T84 cells are cultured under conditions that result in formation of a monolayer of epithelial cells on a permeable support, as described in Madara, J. and K. Dharmsathaphorn (*J. Cell Biol.*, 101:2124-2133, 1985), Madara, J. and J. Stafford (*J. Clin. Invest.* 83:724-727, 1989), and Youakim, A. and M. Ahdieh (*Am. J. Physiol.* 276 (Gastrointest. Liver Physiol. 39):G1279-G1288, 1999). The cultured monolayers are tested for properties such as resistance to passive transepithelial ion flow (such resistance indicating an intact monolayer performing a barrier function). The thus-generated epithelial monolayer simulates the intestinal epithelial barrier.

One type of assay determines whether a particular radiolabeled compound is able to cross an epithelial monolayer (e.g., a monolayer generated as described above). Transport of the radiolabeled compound across the monolayer indicates that the barrier is permeable rather than intact. One such procedure is mannitol flux analysis, which assesses movement of radiolabeled mannitol (e.g., $^3$H mannitol) across a monolayer (see Madara and Stafford, supra).

Methods for imaging a monolayer are identified in Madara and Stafford, supra. Such imaging methods are an alternative for assessing the condition of an epithelial layer, after exposure to IL-4 with or without an antagonist.

Youakim and Ahdieh, supra, discuss proteins that are part of "tight junction" complexes in intact intestinal epithelial barriers, and report studies of the effect of IFN-γ on proteins associated with tight junctions. Other techniques for studying the effect of a cytokine on barrier function are described. For example, the effect of a cytokine on monolayer permeability may be assessed by transepithelial electrical resistance measurements, using techniques described in the reference.

U.S. Pat. No. 6,033,688 also describes procedures that may be employed in studies of barrier permeability; see especially examples 1 and 4 of the patent. Human tracheal epithelial cells were cultured under conditions that yielded a monolayer exhibiting transepithelial electrical resistance. Transepithelial resistance (indicating an intact barrier) was determined using a voltmeter. The effect of a particular reagent (HGH) on the epithelial monolayer was assessed by exposing the monolayer to HGH, and then measuring ion transport activities in Ussing chambers, by standard methods (column 8, lines 40-56). Similar studies were conducted on monolayers that were generated from bronchial epithelial cells from a human cystic fibrosis patient (example 4, column 11).

Using any of the above-described barrier function assay procedures, an epithelial monolayer is exposed to IL-4 alone, or exposed to IL-4 in the presence of an IL-4 antagonist. The antagonist's ability to inhibit the IL-4-induced reduction in barrier function thus is assessed.

In one such assay, a monolayer of T84 cells served as an in vitro model of an intestinal epithelial barrier, as discussed above. IL-4 added to the basolateral side of polarized epithelial cells was found to reduce barrier function by 70% within 48-72 hours of treatment. When an IL-4 receptor polypeptide was added at the same time as IL-4, the reduction in barrier function was prevented, and the barrier was maintained at the same level as untreated (control) cells. A soluble human IL-4 receptor polypeptide, consisting of the extracellular domain, was employed in the assay.

The assay procedure also was conducted on a monolayer derived from lung epithelial cells, which served as an in vitro model of a lung epithelial barrier. IL-4 added to the basolateral side of polarized lung epithelial cells was found to reduce barrier function by 50% within 48-72 hours of treatment. When the IL-4 receptor polypeptide was added at the same time as IL-4, the reduction in barrier function was prevented, and the barrier was maintained at the same level as untreated (control) cells.

Example 8

Monoclonal Antibody designated 12B5

A human monoclonal antibody directed against human IL-4 receptor was prepared by the following procedure. The monoclonal antibody, which is designated 12B5, is a blocking antibody that functions as an IL-4 antagonist and as an IL-13 antagonist.

The procedure began with immunization of a transgenic mouse with a soluble human IL-4 receptor polypeptide.

Mouse strain ((CMD)++; (JKD)++; (HCo7)11952+/++; (KCo5)9272+/++), described in example 3 above, was employed. The antigen for immunization was purified soluble IL-4R, comprising the extracellular domain of human IL-4 receptor (500 ug/ml). The mouse was initially immunized with 50 ug antigen emulsified in Complete Freund's Adjuvant, followed by two more immunizations with Incomplete Freund's Adjuvant at 50 ug and then 25 ug. Immunization was every two weeks by intraperitoneal injection. A specific human IgG anti-IL-4R titer from the serum was performed by ELISA, eight days after the last injection. A good titer against the target was detected, and the mouse then was IV/IP boosted 25 ug each on day $^-$3 (i.e., 3 days before the mouse was sacrificed) and 15 ug IV on day $^-$2.

The mouse was sacrificed, and spleen cells were extracted and fused with the murine myeloma cell line P3x63Ag8.653 (ATCC CRL 1580). A conventional PEG fusion protocol was followed. The fusion was screened for HuIgG and HuKappa, followed by a rescreen for human gamma and kappa specific to IL-4R. The positive clones were evaluated, and clone 12B5 was identified as a blocking antibody. The clone was subcloned; a hybridoma cell line that produces MAb 12B5 was isolated; and MAb 12B5 was purified from the supernatant.

12B5 was determined to be an IgG1 antibody, and to be fully human. Antibodies of other subclasses, such as IgG4 or IgM monoclonal antibodies, may be derived from 12B5. Techniques for altering (switching) the subclass/isotype of an antibody are known. The constant region of 12B5 may be replaced, for example, with a constant region derived from a human IgG4 antibody. Sequence information for a human IgG4 heavy chain is presented, for example, in Ellison et al. (*DNA* Vol. 1, no. 1, pp 11-18, 1981), which is hereby incorporated by reference herein.

DNA encoding the variable region of the light chain of MAb 12B5 was isolated, and the nucleotide sequence thereof was determined. The DNA sequence for the light chain variable region is presented as SEQ ID NO:9; the amino acid sequence encoded thereby is presented in SEQ ID NO:10. Complementarity determining regions 1 to 3 (CDR 1-3) are believed to correspond to amino acids 24-35, 51-57, and 90-99, of SEQ ID NO:10, respectively.

DNA encoding the variable region of the heavy chain of MAb 12B5 was isolated, and the nucleotide sequence thereof was determined. The DNA sequence for the heavy chain variable region is presented as SEQ ID NO:11; the amino acid sequence encoded thereby is presented in SEQ ID NO:12. CDR-1 of the heavy chain is believed to correspond to amino acids 31-35; CDR-2 to amino acids 50-65; and CDR-3 to amino acids 98-104 of SEQ ID NO:12.

Example 9

Additional Monoclonal Antibodies that Inhibit Both IL-4 and IL-13

Additional human monoclonal antibodies were raised against human IL-4 receptor, by immunizing transgenic mice with a soluble human IL-4R polypeptide. The transgenic mice employed were selected from the transgenic mouse strains described in example 3.

Hybridoma cell lines secreting human monoclonal antibodies that specifically bind human IL-4R, and which are capable of functioning as IL-4 antagonists and IL-13 antagonists, were identified and isolated. The MAbs are designated 27A1, 5A1, and 63. Another MAb, designated 1B7, was derived from MAb 63, and differs from the parent antibody only in the light chain. 1B7 retains the ability to bind IL-4R and to function as an IL-4 antagonist and an IL-13 antagonist.

The DNA sequence of the variable region of the light chain of MAb 27A1 is presented in SEQ ID NO:13, and the encoded amino acid sequence is presented in SEQ ID NO:14. Complementarity determining regions 1 to 3 (CDR 1-3) are believed to correspond to amino acids 24-35, 51-57, and 90-99, of SEQ ID NO:14, respectively.

The DNA sequence for the variable region of the heavy chain of MAb 27A1 is presented as SEQ ID NO:15, and the encoded amino acid sequence is presented in SEQ ID NO:16. Complementarity determining regions 1 to 3 (CDR 1-3) are believed to correspond to amino acids 31-35, 50-66, and 99-105, of SEQ ID NO:16, respectively.

The DNA sequence of the variable region of the light chain of MAb 5A1 is presented in SEQ ID NO:17, and the encoded amino acid sequence is presented in SEQ ID NO:18. Complementarity determining regions 1 to 3 (CDR 1-3) are believed to correspond to amino acids 24-34, 50-56, and 89-97 of SEQ ID NO:18, respectively.

The DNA sequence for the variable region of the heavy chain of MAb 5A1 is presented as SEQ ID NO:19, and the encoded amino acid sequence is presented in SEQ ID NO:20. Complementarity determining regions 1 to 3 (CDR 1-3) are believed to correspond to amino acids 31-35, 50-65, and 98-112 of SEQ ID NO:20, respectively.

The DNA sequence of the variable region of the light chain of MAb 63 is presented in SEQ ID NO:21, and the encoded amino acid sequence is presented in SEQ ID NO:22. Complementarity determining regions 1 to 3 (CDR 1-3) are believed to correspond to amino acids 24-34, 50-56, and 89-97 of SEQ ID NO:22, respectively.

The DNA sequence for the variable region of the heavy chain of MAb 63 is presented as SEQ ID NO:23, and the encoded amino acid sequence is presented in SEQ ID NO:24. Complementarity determining regions 1 to 3 (CDR 1-3) are believed to correspond to amino acids 31-35, 50-66, and 99-106 of SEQ ID NO:24, respectively.

The DNA sequence of the variable region of the light chain of MAb 1B7 is presented in SEQ ID NO:25, and the encoded amino acid sequence is presented in SEQ ID NO:26. Complementarity determining regions 1 to 3 (CDR 1-3) are believed to correspond to amino acids 24-34, 50-56, and 89-97 of SEQ ID NO:26, respectively.

MAb 1B7 was derived from MAb 63, and the heavy chains of the two MAbs are identical. Thus, the DNA sequence for the variable region of the heavy chain of MAb 1B7 is presented as SEQ ID NO:23, and the encoded amino acid sequence is presented in SEQ ID NO:24. Complementarity determining regions 1 to 3 (CDRs 1-3) are believed to correspond to amino acids 31-35, 50-66, and 99-106 of SEQ ID NO:24, respectively.

What is claimed is:

1. An isolated human antibody that competes with a reference antibody for binding to human IL-4 interleukin-4 (IL-4) receptor, wherein the light chain of said reference antibody comprises the amino acid sequence of SEQ ID NO:10 and the heavy chain of said reference antibody comprises the amino acid sequence of SEQ ID NO:12.

2. The isolated human antibody of claim 1, wherein when said reference antibody is bound to human IL-4 receptor, binding of said isolated antibody to said human IL-4 receptor is inhibited.

3. The isolated human antibody of claim 1, wherein when said isolated human antibody is bound to human IL-4 receptor, binding of said reference antibody to said human IL-4 receptor is inhibited.

4. The isolated human antibody of claim 1, wherein said isolated human antibody inhibits the binding of human IL-4 to human IL-4 receptor.

5. The isolated human antibody of claim 1, wherein said isolated human antibody inhibits the binding of human IL-13 interleukin-13 (IL-13) to human IL-4 receptor.

6. The isolated human antibody of claim 1, wherein said isolated human antibody inhibits human IL-4 signaling through human IL-4 receptor.

7. The isolated human antibody of claim 1, wherein said isolated human antibody inhibits human IL-13 signaling through human IL-4 receptor.

8. The isolated human antibody of claim 1, wherein said isolated human antibody binds to human IL-4 receptor with a binding affinity ($K_a$) of at least $1\times10^8$.

9. The isolated human antibody of claim 1, wherein said isolated human antibody binds to human IL-4 receptor with a binding affinity ($K_a$) of at least $1\times10^9$.

10. The isolated human antibody of claim 1, wherein said isolated human antibody binds to human IL-4 receptor with a binding affinity ($K_a$) of at least $1\times10^{10}$.

11. The isolated human antibody of claim 1, wherein said isolated human antibody is a full-length antibody.

12. The isolated human antibody of claim 1, wherein said isolated human antibody is an IgA antibody, an IgD antibody, an IgE antibody, IgG antibody, an IgG1 antibody, an IgG2 antibody, an IgG3, antibody, an IgG4 antibody, or an IgM antibody.

13. The isolated human antibody of claim 1, wherein said isolated human antibody is a fragment of an antibody.

14. The isolated human antibody of claim 1, wherein said isolated human antibody is a fusion protein.

15. The isolated human antibody of claim 1, wherein said isolated human antibody is a single chain antibody (scFv).

16. A composition comprising said isolated human antibody of claim 1 and a pharmaceutically acceptable diluent, buffer, or excipient.

17. A kit comprising said isolated human antibody of claim 1.

* * * * *

SEQUENCE LISTING

<160> NUMBER OF SEQ ID NOS: 26

<210> SEQ ID NO 1
<211> LENGTH: 2478
<212> TYPE: DNA
<213> ORGANISM: Homo sapiens
<220> FEATURE:
<221> NAME/KEY: CDS
<222> LOCATION: (1)..(2475)
<220> FEATURE:
<221> NAME/KEY: mat_peptide
<222> LOCATION: (76)..()

<400> SEQUENCE: 1

| | | | | | | | | | | | | | | | | |
|---|---|---|---|---|---|---|---|---|---|---|---|---|---|---|---|---|
| atg | ggg | tgg | ctt | tgc | tct | ggg | ctc | ctg | ttc | cct | gtg | agc | tgc | ctg | gtc | 48 |
| Met | Gly | Trp | Leu | Cys | Ser | Gly | Leu | Leu | Phe | Pro | Val | Ser | Cys | Leu | Val | |
| -25 | | | | -20 | | | | | -15 | | | | | -10 | | |

| ctg | ctg | cag | gtg | gca | agc | tct | ggg | aac | atg | aag | gtc | ttg | cag | gag | ccc | 96 |
|---|---|---|---|---|---|---|---|---|---|---|---|---|---|---|---|---|
| Leu | Leu | Gln | Val | Ala | Ser | Ser | Gly | Asn | Met | Lys | Val | Leu | Gln | Glu | Pro | |
| | | | | -5 | | | | -1 | 1 | | | | 5 | | | |

| acc | tgc | gtc | tcc | gac | tac | atg | agc | atc | tct | act | tgc | gag | tgg | aag | atg | 144 |
|---|---|---|---|---|---|---|---|---|---|---|---|---|---|---|---|---|
| Thr | Cys | Val | Ser | Asp | Tyr | Met | Ser | Ile | Ser | Thr | Cys | Glu | Trp | Lys | Met | |
| | | 10 | | | | | 15 | | | | | 20 | | | | |

| aat | ggt | ccc | acc | aat | tgc | agc | acc | gag | ctc | cgc | ctg | ttg | tac | cag | ctg | 192 |
|---|---|---|---|---|---|---|---|---|---|---|---|---|---|---|---|---|
| Asn | Gly | Pro | Thr | Asn | Cys | Ser | Thr | Glu | Leu | Arg | Leu | Leu | Tyr | Gln | Leu | |
| | 25 | | | | | 30 | | | | | 35 | | | | | |

| gtt | ttt | ctg | ctc | tcc | gaa | gcc | cac | acg | tgt | atc | cct | gag | aac | aac | gga | 240 |
|---|---|---|---|---|---|---|---|---|---|---|---|---|---|---|---|---|
| Val | Phe | Leu | Leu | Ser | Glu | Ala | His | Thr | Cys | Ile | Pro | Glu | Asn | Asn | Gly | |
| 40 | | | | | 45 | | | | | 50 | | | | | 55 | |

| ggc | gcg | ggg | tgc | gtg | tgc | cac | ctg | ctc | atg | gat | gac | gtg | gtc | agt | gcg | 288 |
|---|---|---|---|---|---|---|---|---|---|---|---|---|---|---|---|---|
| Gly | Ala | Gly | Cys | Val | Cys | His | Leu | Leu | Met | Asp | Asp | Val | Val | Ser | Ala | |
| | | | 60 | | | | | 65 | | | | | 70 | | | |

| gat | aac | tat | aca | ctg | gac | ctg | tgg | gct | ggg | cag | cag | ctg | ctg | tgg | aag | 336 |
|---|---|---|---|---|---|---|---|---|---|---|---|---|---|---|---|---|
| Asp | Asn | Tyr | Thr | Leu | Asp | Leu | Trp | Ala | Gly | Gln | Gln | Leu | Leu | Trp | Lys | |
| | | 75 | | | | | 80 | | | | | 85 | | | | |

| ggc | tcc | ttc | aag | ccc | agc | gag | cat | gtg | aaa | ccc | agg | gcc | cca | gga | aac | 384 |
|---|---|---|---|---|---|---|---|---|---|---|---|---|---|---|---|---|
| Gly | Ser | Phe | Lys | Pro | Ser | Glu | His | Val | Lys | Pro | Arg | Ala | Pro | Gly | Asn | |
| | 90 | | | | | 95 | | | | | 100 | | | | | |

| ctg | aca | gtt | cac | acc | aat | gtc | tcc | gac | act | ctg | ctg | ctg | acc | tgg | agc | 432 |
|---|---|---|---|---|---|---|---|---|---|---|---|---|---|---|---|---|
| Leu | Thr | Val | His | Thr | Asn | Val | Ser | Asp | Thr | Leu | Leu | Leu | Thr | Trp | Ser | |
| | 105 | | | | | 110 | | | | | 115 | | | | | |

| aac | ccg | tat | ccc | cct | gac | aat | tac | ctg | tat | aat | cat | ctc | acc | tat | gca | 480 |
|---|---|---|---|---|---|---|---|---|---|---|---|---|---|---|---|---|
| Asn | Pro | Tyr | Pro | Pro | Asp | Asn | Tyr | Leu | Tyr | Asn | His | Leu | Thr | Tyr | Ala | |
| 120 | | | | | 125 | | | | | 130 | | | | | 135 | |

| gtc | aac | att | tgg | agt | gaa | aac | gac | ccg | gca | gat | ttc | aga | atc | tat | aac | 528 |
|---|---|---|---|---|---|---|---|---|---|---|---|---|---|---|---|---|
| Val | Asn | Ile | Trp | Ser | Glu | Asn | Asp | Pro | Ala | Asp | Phe | Arg | Ile | Tyr | Asn | |
| | | | | 140 | | | | | 145 | | | | | 150 | | |

| gtg | acc | tac | cta | gaa | ccc | tcc | ctc | cgc | atc | gca | gcc | agc | acc | ctg | aag | 576 |
|---|---|---|---|---|---|---|---|---|---|---|---|---|---|---|---|---|
| Val | Thr | Tyr | Leu | Glu | Pro | Ser | Leu | Arg | Ile | Ala | Ala | Ser | Thr | Leu | Lys | |
| | | | 155 | | | | | 160 | | | | | 165 | | | |

| tct | ggg | att | tcc | tac | agg | gca | cgg | gtg | agg | gcc | tgg | gct | cag | tgc | tat | 624 |
|---|---|---|---|---|---|---|---|---|---|---|---|---|---|---|---|---|
| Ser | Gly | Ile | Ser | Tyr | Arg | Ala | Arg | Val | Arg | Ala | Trp | Ala | Gln | Cys | Tyr | |
| | | 170 | | | | | 175 | | | | | 180 | | | | |

| aac | acc | acc | tgg | agt | gag | tgg | agc | ccc | agc | acc | aag | tgg | cac | aac | tcc | 672 |
|---|---|---|---|---|---|---|---|---|---|---|---|---|---|---|---|---|
| Asn | Thr | Thr | Trp | Ser | Glu | Trp | Ser | Pro | Ser | Thr | Lys | Trp | His | Asn | Ser | |
| | 185 | | | | | 190 | | | | | 195 | | | | | |

| tac | agg | gag | ccc | ttc | gag | cag | cac | ctc | ctg | ctg | ggc | gtc | agc | gtt | tcc | 720 |
|---|---|---|---|---|---|---|---|---|---|---|---|---|---|---|---|---|
| Tyr | Arg | Glu | Pro | Phe | Glu | Gln | His | Leu | Leu | Leu | Gly | Val | Ser | Val | Ser | |
| 200 | | | | | 205 | | | | | 210 | | | | | 215 | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tgc | att | gtc | atc | ctg | gcc | gtc | tgc | ctg | ttg | tgc | tat | gtc | agc | atc | acc | 768  |
| Cys | Ile | Val | Ile | Leu | Ala | Val | Cys | Leu | Leu | Cys | Tyr | Val | Ser | Ile | Thr |      |
|     |     |     | 220 |     |     |     |     | 225 |     |     |     |     | 230 |     |     |      |
| aag | att | aag | aaa | gaa | tgg | tgg | gat | cag | att | ccc | aac | cca | gcc | cgc | agc | 816  |
| Lys | Ile | Lys | Lys | Glu | Trp | Trp | Asp | Gln | Ile | Pro | Asn | Pro | Ala | Arg | Ser |      |
|     |     |     | 235 |     |     |     |     | 240 |     |     |     |     | 245 |     |     |      |
| cgc | ctc | gtg | gct | ata | ata | atc | cag | gat | gct | cag | ggg | tca | cag | tgg | gag | 864  |
| Arg | Leu | Val | Ala | Ile | Ile | Ile | Gln | Asp | Ala | Gln | Gly | Ser | Gln | Trp | Glu |      |
|     |     |     | 250 |     |     |     |     | 255 |     |     |     |     | 260 |     |     |      |
| aag | cgg | tcc | cga | ggc | cag | gaa | cca | gcc | aag | tgc | cca | cac | tgg | aag | aat | 912  |
| Lys | Arg | Ser | Arg | Gly | Gln | Glu | Pro | Ala | Lys | Cys | Pro | His | Trp | Lys | Asn |      |
|     |     |     | 265 |     |     |     |     | 270 |     |     |     |     | 275 |     |     |      |
| tgt | ctt | acc | aag | ctc | ttg | ccc | tgt | ttt | ctg | gag | cac | aac | atg | aaa | agg | 960  |
| Cys | Leu | Thr | Lys | Leu | Leu | Pro | Cys | Phe | Leu | Glu | His | Asn | Met | Lys | Arg |      |
| 280 |     |     |     |     | 285 |     |     |     |     | 290 |     |     |     |     | 295 |      |
| gat | gaa | gat | cct | cac | aag | gct | gcc | aaa | gag | atg | cct | ttc | cag | ggc | tct | 1008 |
| Asp | Glu | Asp | Pro | His | Lys | Ala | Ala | Lys | Glu | Met | Pro | Phe | Gln | Gly | Ser |      |
|     |     |     |     | 300 |     |     |     |     | 305 |     |     |     |     | 310 |     |      |
| gga | aaa | tca | gca | tgg | tgc | cca | gtg | gag | atc | agc | aag | aca | gtc | ctc | tgg | 1056 |
| Gly | Lys | Ser | Ala | Trp | Cys | Pro | Val | Glu | Ile | Ser | Lys | Thr | Val | Leu | Trp |      |
|     |     |     | 315 |     |     |     |     | 320 |     |     |     |     | 325 |     |     |      |
| cca | gag | agc | atc | agc | gtg | gtg | cga | tgt | gtg | gag | ttg | ttt | gag | gcc | ccg | 1104 |
| Pro | Glu | Ser | Ile | Ser | Val | Val | Arg | Cys | Val | Glu | Leu | Phe | Glu | Ala | Pro |      |
|     |     |     | 330 |     |     |     |     | 335 |     |     |     |     | 340 |     |     |      |
| gtg | gag | tgt | gag | gag | gag | gag | gta | gag | gaa | gaa | aaa | ggg | agc | ttc |     | 1152 |
| Val | Glu | Cys | Glu | Glu | Glu | Glu | Val | Glu | Glu | Glu | Lys | Gly | Ser | Phe |     |      |
|     |     | 345 |     |     |     |     | 350 |     |     |     |     | 355 |     |     |     |      |
| tgt | gca | tcg | cct | gag | agc | agc | agg | gat | gac | ttc | cag | gag | gga | agg | gag | 1200 |
| Cys | Ala | Ser | Pro | Glu | Ser | Ser | Arg | Asp | Asp | Phe | Gln | Glu | Gly | Arg | Glu |      |
| 360 |     |     |     |     | 365 |     |     |     |     | 370 |     |     |     |     | 375 |      |
| ggc | att | gtg | gcc | cgg | cta | aca | gag | agc | ctg | ttc | ctg | gac | ctg | ctc | gga | 1248 |
| Gly | Ile | Val | Ala | Arg | Leu | Thr | Glu | Ser | Leu | Phe | Leu | Asp | Leu | Leu | Gly |      |
|     |     |     | 380 |     |     |     |     | 385 |     |     |     |     | 390 |     |     |      |
| gag | gag | aat | ggg | ggc | ttt | tgc | cag | cag | gac | atg | ggg | gag | tca | tgc | ctt | 1296 |
| Glu | Glu | Asn | Gly | Gly | Phe | Cys | Gln | Gln | Asp | Met | Gly | Glu | Ser | Cys | Leu |      |
|     |     |     | 395 |     |     |     |     | 400 |     |     |     |     | 405 |     |     |      |
| ctt | cca | cct | tcg | gga | agt | acg | agt | gct | cac | atg | ccc | tgg | gat | gag | ttc | 1344 |
| Leu | Pro | Pro | Ser | Gly | Ser | Thr | Ser | Ala | His | Met | Pro | Trp | Asp | Glu | Phe |      |
|     |     |     |     | 410 |     |     |     |     | 415 |     |     |     |     | 420 |     |      |
| cca | agt | gca | ggg | ccc | aag | gag | gca | cct | ccc | tgg | ggc | aag | gag | cag | cct | 1392 |
| Pro | Ser | Ala | Gly | Pro | Lys | Glu | Ala | Pro | Pro | Trp | Gly | Lys | Glu | Gln | Pro |      |
|     |     |     | 425 |     |     |     |     | 430 |     |     |     |     | 435 |     |     |      |
| ctc | cac | ctg | gag | cca | agt | cct | cct | gcc | agc | ccg | acc | cag | agt | cca | gac | 1440 |
| Leu | His | Leu | Glu | Pro | Ser | Pro | Pro | Ala | Ser | Pro | Thr | Gln | Ser | Pro | Asp |      |
| 440 |     |     |     |     | 445 |     |     |     |     | 450 |     |     |     |     | 455 |      |
| aac | ctg | act | tgc | aca | gag | acg | ccc | ctc | gtc | atc | gca | ggc | aac | cct | gct | 1488 |
| Asn | Leu | Thr | Cys | Thr | Glu | Thr | Pro | Leu | Val | Ile | Ala | Gly | Asn | Pro | Ala |      |
|     |     |     |     | 460 |     |     |     |     | 465 |     |     |     |     | 470 |     |      |
| tac | cgc | agc | ttc | agc | aac | tcc | ctg | agc | cag | tca | ccg | tgt | ccc | aga | gag | 1536 |
| Tyr | Arg | Ser | Phe | Ser | Asn | Ser | Leu | Ser | Gln | Ser | Pro | Cys | Pro | Arg | Glu |      |
|     |     |     | 475 |     |     |     |     | 480 |     |     |     |     | 485 |     |     |      |
| ctg | ggt | cca | gac | cca | ctg | ctg | gcc | aga | cac | ctg | gag | gaa | gta | gaa | ccc | 1584 |
| Leu | Gly | Pro | Asp | Pro | Leu | Leu | Ala | Arg | His | Leu | Glu | Glu | Val | Glu | Pro |      |
|     |     |     | 490 |     |     |     |     | 495 |     |     |     |     | 500 |     |     |      |
| gag | atg | ccc | tgt | gtc | ccc | cag | ctc | tct | gag | cca | acc | act | gtg | ccc | caa | 1632 |
| Glu | Met | Pro | Cys | Val | Pro | Gln | Leu | Ser | Glu | Pro | Thr | Thr | Val | Pro | Gln |      |
|     |     | 505 |     |     |     |     | 510 |     |     |     |     | 515 |     |     |     |      |
| cct | gag | cca | gaa | acc | tgg | gag | cag | atc | ctc | cgc | cga | aat | gtc | ctc | cag | 1680 |
| Pro | Glu | Pro | Glu | Thr | Trp | Glu | Gln | Ile | Leu | Arg | Arg | Asn | Val | Leu | Gln |      |
| 520 |     |     |     |     | 525 |     |     |     |     | 530 |     |     |     |     | 535 |      |

```
cat ggg gca gct gca gcc ccc gtc tcg gcc ccc acc agt ggc tat cag      1728
His Gly Ala Ala Ala Ala Pro Val Ser Ala Pro Thr Ser Gly Tyr Gln
            540                 545                 550 gag ttt gta cat gcg gtg gag cag ggt ggc acc cag gcc agt gcg gtg      1776
Glu Phe Val His Ala Val Glu Gln Gly Gly Thr Gln Ala Ser Ala Val
        555                 560                 565 gtg ggc ttg ggt ccc cca gga gag gct ggt tac aag gcc ttc tca agc      1824
Val Gly Leu Gly Pro Pro Gly Glu Ala Gly Tyr Lys Ala Phe Ser Ser
    570                 575                 580 ctg ctt gcc agc agt gct gtg tcc cca gag aaa tgt ggg ttt ggg gct      1872
Leu Leu Ala Ser Ser Ala Val Ser Pro Glu Lys Cys Gly Phe Gly Ala
585                 590                 595 agc agt ggg gaa gag ggg tat aag cct ttc caa gac ctc att cct ggc      1920
Ser Ser Gly Glu Glu Gly Tyr Lys Pro Phe Gln Asp Leu Ile Pro Gly
600                 605                 610                 615 tgc cct ggg gac cct gcc cca gtc cct gtc ccc ttg ttc acc ttt gga      1968
Cys Pro Gly Asp Pro Ala Pro Val Pro Val Pro Leu Phe Thr Phe Gly
            620                 625                 630 ctg gac agg gag cca cct cgc agt ccg cag agc tca cat ctc cca agc      2016
Leu Asp Arg Glu Pro Pro Arg Ser Pro Gln Ser Ser His Leu Pro Ser
        635                 640                 645 agc tcc cca gag cac ctg ggt ctg gag ccg ggg gaa aag gta gag gac      2064
Ser Ser Pro Glu His Leu Gly Leu Glu Pro Gly Glu Lys Val Glu Asp
    650                 655                 660 atg cca aag ccc cca ctt ccc cag gag cag gcc aca gac ccc ctt gtg      2112
Met Pro Lys Pro Pro Leu Pro Gln Glu Gln Ala Thr Asp Pro Leu Val
665                 670                 675 gac agc ctg ggc agt ggc att gtc tac tca gcc ctt acc tgc cac ctg      2160
Asp Ser Leu Gly Ser Gly Ile Val Tyr Ser Ala Leu Thr Cys His Leu
680                 685                 690                 695 tgc ggc cac ctg aaa cag tgt cat ggc cag gag gat ggt ggc cag acc      2208
Cys Gly His Leu Lys Gln Cys His Gly Gln Glu Asp Gly Gly Gln Thr
            700                 705                 710 cct gtc atg gcc agt cct tgc tgt ggc tgc tgt tgt gga gac agg tcc      2256
Pro Val Met Ala Ser Pro Cys Cys Gly Cys Cys Cys Gly Asp Arg Ser
        715                 720                 725 tcg ccc cct aca acc ccc ctg agg gcc cca gac ccc tct cca ggt ggg      2304
Ser Pro Pro Thr Thr Pro Leu Arg Ala Pro Asp Pro Ser Pro Gly Gly
    730                 735                 740 gtt cca ctg gag gcc agt ctg tgt ccg gcc tcc ctg gca ccc tcg ggc      2352
Val Pro Leu Glu Ala Ser Leu Cys Pro Ala Ser Leu Ala Pro Ser Gly
745                 750                 755 atc tca gag aag agt aaa tcc tca tcc ttc cat cct gcc cct ggc          2400
Ile Ser Glu Lys Ser Lys Ser Ser Ser Phe His Pro Ala Pro Gly
760                 765                 770                 775 aat gct cag agc tca agc cag acc ccc aaa atc gtg aac ttt gtc tcc      2448
Asn Ala Gln Ser Ser Ser Gln Thr Pro Lys Ile Val Asn Phe Val Ser
            780                 785                 790 gtg gga ccc aca tac atg agg gtc tct tat                              2478
Val Gly Pro Thr Tyr Met Arg Val Ser
            795                 800

<210> SEQ ID NO 2
<211> LENGTH: 825
<212> TYPE: PRT
<213> ORGANISM: Homo sapiens

<400> SEQUENCE: 2

Met Gly Trp Leu Cys Ser Gly Leu Leu Phe Pro Val Ser Cys Leu Val
-25                 -20                 -15                 -10
```

```
Leu Leu Gln Val Ala Ser Ser Gly Asn Met Lys Val Leu Gln Glu Pro
            -5              -1  1              5

Thr Cys Val Ser Asp Tyr Met Ser Ile Ser Thr Cys Glu Trp Lys Met
        10              15              20

Asn Gly Pro Thr Asn Cys Ser Thr Glu Leu Arg Leu Leu Tyr Gln Leu
    25              30              35

Val Phe Leu Leu Ser Glu Ala His Thr Cys Ile Pro Glu Asn Asn Gly
40              45              50              55

Gly Ala Gly Cys Val Cys His Leu Leu Met Asp Asp Val Val Ser Ala
            60              65              70

Asp Asn Tyr Thr Leu Asp Leu Trp Ala Gly Gln Gln Leu Leu Trp Lys
            75              80              85

Gly Ser Phe Lys Pro Ser Glu His Val Lys Pro Arg Ala Pro Gly Asn
        90              95              100

Leu Thr Val His Thr Asn Val Ser Asp Thr Leu Leu Leu Thr Trp Ser
        105             110             115

Asn Pro Tyr Pro Pro Asp Asn Tyr Leu Tyr Asn His Leu Thr Tyr Ala
120             125             130             135

Val Asn Ile Trp Ser Glu Asn Asp Pro Ala Asp Phe Arg Ile Tyr Asn
            140             145             150

Val Thr Tyr Leu Glu Pro Ser Leu Arg Ile Ala Ala Ser Thr Leu Lys
            155             160             165

Ser Gly Ile Ser Tyr Arg Ala Arg Val Arg Ala Trp Ala Gln Cys Tyr
        170             175             180

Asn Thr Thr Trp Ser Glu Trp Ser Pro Ser Thr Lys Trp His Asn Ser
        185             190             195

Tyr Arg Glu Pro Phe Glu Gln His Leu Leu Leu Gly Val Ser Val Ser
200             205             210             215

Cys Ile Val Ile Leu Ala Val Cys Leu Leu Cys Tyr Val Ser Ile Thr
            220             225             230

Lys Ile Lys Lys Glu Trp Trp Asp Gln Ile Pro Asn Pro Ala Arg Ser
            235             240             245

Arg Leu Val Ala Ile Ile Gln Asp Ala Gln Gly Ser Gln Trp Glu
            250             255             260

Lys Arg Ser Arg Gly Gln Glu Pro Ala Lys Cys Pro His Trp Lys Asn
        265             270             275

Cys Leu Thr Lys Leu Leu Pro Cys Phe Leu Glu His Asn Met Lys Arg
280             285             290             295

Asp Glu Asp Pro His Lys Ala Ala Lys Glu Met Pro Phe Gln Gly Ser
            300             305             310

Gly Lys Ser Ala Trp Cys Pro Val Glu Ile Ser Lys Thr Val Leu Trp
            315             320             325

Pro Glu Ser Ile Ser Val Val Arg Cys Val Glu Leu Phe Glu Ala Pro
        330             335             340

Val Glu Cys Glu Glu Glu Glu Val Glu Glu Glu Lys Gly Ser Phe
        345             350             355

Cys Ala Ser Pro Glu Ser Ser Arg Asp Asp Phe Gln Glu Gly Arg Glu
360             365             370             375

Gly Ile Val Ala Arg Leu Thr Glu Ser Leu Phe Leu Asp Leu Leu Gly
            380             385             390

Glu Glu Asn Gly Gly Phe Cys Gln Gln Asp Met Gly Glu Ser Cys Leu
            395             400             405

Leu Pro Pro Ser Gly Ser Thr Ser Ala His Met Pro Trp Asp Glu Phe
            410             415             420
```

```
Pro Ser Ala Gly Pro Lys Glu Ala Pro Pro Trp Gly Lys Glu Gln Pro
    425                 430                 435

Leu His Leu Glu Pro Ser Pro Pro Ala Ser Pro Thr Gln Ser Pro Asp
440                 445                 450                 455

Asn Leu Thr Cys Thr Glu Thr Pro Leu Val Ile Ala Gly Asn Pro Ala
                460                 465                 470

Tyr Arg Ser Phe Ser Asn Ser Leu Ser Gln Ser Pro Cys Pro Arg Glu
            475                 480                 485

Leu Gly Pro Asp Pro Leu Leu Ala Arg His Leu Glu Glu Val Glu Pro
        490                 495                 500

Glu Met Pro Cys Val Pro Gln Leu Ser Glu Pro Thr Thr Val Pro Gln
    505                 510                 515

Pro Glu Pro Glu Thr Trp Glu Gln Ile Leu Arg Arg Asn Val Leu Gln
520                 525                 530                 535

His Gly Ala Ala Ala Pro Val Ser Ala Pro Thr Ser Gly Tyr Gln
                540                 545                 550

Glu Phe Val His Ala Val Glu Gln Gly Gly Thr Gln Ala Ser Ala Val
            555                 560                 565

Val Gly Leu Gly Pro Pro Gly Glu Ala Gly Tyr Lys Ala Phe Ser Ser
        570                 575                 580

Leu Leu Ala Ser Ser Ala Val Ser Pro Glu Lys Cys Gly Phe Gly Ala
    585                 590                 595

Ser Ser Gly Glu Glu Gly Tyr Lys Pro Phe Gln Asp Leu Ile Pro Gly
600                 605                 610                 615

Cys Pro Gly Asp Pro Ala Pro Val Pro Val Pro Leu Phe Thr Phe Gly
                620                 625                 630

Leu Asp Arg Glu Pro Pro Arg Ser Pro Gln Ser Ser His Leu Pro Ser
            635                 640                 645

Ser Ser Pro Glu His Leu Gly Leu Glu Pro Gly Glu Lys Val Glu Asp
        650                 655                 660

Met Pro Lys Pro Pro Leu Pro Gln Glu Gln Ala Thr Asp Pro Leu Val
    665                 670                 675

Asp Ser Leu Gly Ser Gly Ile Val Tyr Ser Ala Leu Thr Cys His Leu
680                 685                 690                 695

Cys Gly His Leu Lys Gln Cys His Gly Gln Glu Asp Gly Gly Gln Thr
                700                 705                 710

Pro Val Met Ala Ser Pro Cys Cys Gly Cys Cys Cys Gly Asp Arg Ser
            715                 720                 725

Ser Pro Pro Thr Thr Pro Leu Arg Ala Pro Asp Pro Ser Pro Gly Gly
        730                 735                 740

Val Pro Leu Glu Ala Ser Leu Cys Pro Ala Ser Leu Ala Pro Ser Gly
    745                 750                 755

Ile Ser Glu Lys Ser Lys Ser Ser Ser Phe His Pro Ala Pro Gly
760                 765                 770                 775

Asn Ala Gln Ser Ser Ser Gln Thr Pro Lys Ile Val Asn Phe Val Ser
                780                 785                 790

Val Gly Pro Thr Tyr Met Arg Val Ser
            795                 800

<210> SEQ ID NO 3
<211> LENGTH: 8
<212> TYPE: PRT
<213> ORGANISM: Artificial
<220> FEATURE:
<223> OTHER INFORMATION: FLAG peptide
```

<400> SEQUENCE: 3

Asp Tyr Lys Asp Asp Asp Asp Lys
1               5

<210> SEQ ID NO 4
<211> LENGTH: 3159
<212> TYPE: DNA
<213> ORGANISM: Artificial
<220> FEATURE:
<223> OTHER INFORMATION: "Cloning vector pGP1k"

<400> SEQUENCE: 4

```
aattagcggc cgctgtcgac aagcttcgaa ttcagtatcg atgtgggta cctactgtcc      60
cgggattgcg gatccgcgat gatatcgttg atcctcgagt gcggccgcag tatgcaaaaa    120
aaagcccgct cattaggcgg gctcttggca gaacatatcc atcgcgtccg ccatctccag    180
cagccgcacg cggcgcatct cgggcagcgt tgggtcctgg ccacgggtgc gcatgatcgt    240
gctcctgtcg ttgaggaccc ggctaggctg gcggggttgc cttactggtt agcagaatga    300
atcaccgata cgcgagcgaa cgtgaagcga ctgctgctgc aaaacgtctg cgacctgagc    360
aacaacatga atggtcttcg gtttccgtgt ttcgtaaagt ctggaaacgc ggaagtcagc    420
gccctgcacc attatgttcc ggatctgcat cgcaggatgc tgctggctac cctgtggaac    480
acctacatct gtattaacga agcgctggca ttgaccctga gtgatttttc tctggtcccg    540
ccgcatccat accgccagtt gtttaccctc acaacgttcc agtaaccggg catgttcatc    600
atcagtaacc cgtatcgtga gcatcctctc tcgtttcatc ggtatcatta cccccatgaa    660
cagaaattcc cccttacacg gaggcatcaa gtgaccaaac aggaaaaaac cgcccttaac    720
atggcccgct ttatcagaag ccagacatta acgcttctgg agaaactcaa cgagctggac    780
gcggatgaac aggcagacat ctgtgaatcg cttcacgacc acgctgatga gctttaccgc    840
agctgcctcg cgcgtttcgg tgatgacggt gaaaacctct gacacatgca gctcccggag    900
acggtcacag cttgtctgta agcggatgcc gggagcagac aagcccgtca gggcgcgtca    960
gcgggtgttg gcgggtgtcg gggcgcagcc atgacccagt cacgtagcga tagcggagtg   1020
tatactggct taactatgcg gcatcagagc agattgtact gagagtgcac catatgcggt   1080
gtgaaatacc gcacagatgc gtaaggagaa ataccgcat caggcgctct ccgcttcct    1140
cgctcactga ctcgctgcgc tcggtcgttc ggctgcggcg agcggtatca gctcactcaa   1200
aggcggtaat acggttatcc acagaatcag gggataacgc aggaaagaac atgtgagcaa   1260
aaggccagca aaaggccagg aaccgtaaaa aggccgcgtt gctggcgttt ttccataggc   1320
tccgcccccc tgacgagcat cacaaaaatc gacgctcaag tcagaggtgg cgaaacccga   1380
caggactata aagataccag gcgtttcccc ctggaagctc cctcgtgcgc tctcctgttc   1440
cgaccctgcc gcttaccgga tacctgtccg cctttctccc ttcgggaagc gtggcgcttt   1500
ctcatagctc acgctgtagg tatctcagtt cggtgtaggt cgttcgctcc aagctgggct   1560
gtgtgcacga accccccgtt cagcccgacc gctgcgcctt atccggtaac tatcgtcttg   1620
agtccaaccc ggtaagacac gacttatcgc cactggcagc agccaggcgc gccttggcct   1680
aagaggccac tggtaacagg attagcagag cgaggtatgt aggcggtgct acagagttct   1740
tgaagtggtg gcctaactac ggctacacta gaaggacagt atttggtatc tgcgctctgc   1800
tgaagccagt taccttcgga aaaagagttg gtagctcttg atccggcaaa caaaccaccg   1860
ctggtagcgg tggttttttt gtttgcaagc agcagattac gcgcagaaaa aaggatctc   1920
```

-continued

```
aagaagatcc tttgatcttt tctacggggt ctgacgctca gtggaacgaa aactcacgtt     1980
aagggatttt ggtcatgaga ttatcaaaaa ggatcttcac ctagatcctt ttaaattaaa     2040
aatgaagttt aaatcaatc taaagtatat atgagtaaac ttggtctgac agttaccaat      2100
gcttaatcag tgaggcacct atctcagcga tctgtctatt tcgttcatcc atagttgcct     2160
gactccccgt cgtgtagata actacgatac gggagggctt accatctggc cccagtgctg     2220
caatgatacc gcgagaccca cgctcaccgg ctccagattt atcagcaata aaccagccag     2280
ccggaagggc cgagcgcaga agtggtcctg caactttatc cgcctccatc cagtctatta     2340
attgttgccg ggaagctaga gtaagtagtt cgccagttaa tagtttgcgc aacgttgttg     2400
ccattgctgc aggcatcgtg gtgtcacgct cgtcgtttgg tatggcttca ttcagctccg     2460
gttcccaacg atcaaggcga gttacatgat cccccatgtt gtgcaaaaaa gcggttagct     2520
ccttcggtcc tccgatcgtt gtcagaagta agttggccgc agtgttatca ctcatggtta     2580
tggcagcact gcataattct cttactgtca tgccatccgt aagatgcttt tctgtgactg     2640
gtgagtactc aaccaagtca ttctgagaat agtgtatgcg gcgaccgagt tgctcttgcc     2700
cggcgtcaac acgggataat accgcgccac atagcagaac tttaaaagtg ctcatcattg     2760
gaaaacgttc ttcggggcga aaactctcaa ggatcttacc gctgttgaga tccagttcga     2820
tgtaacccac tcgtgcaccc aactgatctt cagcatcttt tactttcacc agcgtttctg     2880
ggtgagcaaa acaggaagg caaaatgccg caaaaaggg aataagggcg cacggaaat       2940 gttgaatact catactcttc cttttcaat attattgaag catttatcag ggttattgtc     3000
tcatgagcgg atacatattt gaatgtattt agaaaaataa acaataggg gttccgcgca     3060 catttccccg aaaagtgcca cctgacgtct aagaaaccat tattatcatg acattaacct     3120
ataaaaatag gcgtatcacg aggccctttc gtcttcaag                            3159
```

<210> SEQ ID NO 5
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 5

```
gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc acc agc      96
Glu Arg Ala Thr Leu Ser Cys Arg Ala Ser Gln Ser Val Ser Thr Ser
            20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agt tca ccg     288
Pro Glu Asp Phe Ala Val Tyr Tyr Cys Gln Gln Tyr Gly Ser Ser Pro
                85                  90                  95 acg ttc ggc caa ggg acc aag gtg gaa atc aaa                          321
Thr Phe Gly Gln Gly Thr Lys Val Glu Ile Lys
            100                 105
```

<210> SEQ ID NO 6
<211> LENGTH: 107
<212> TYPE: PRT
<213> ORGANISM: Homo sapiens

<400> SEQUENCE: 6

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gln Gly Thr Lys Val Glu Ile Lys
            100                 105
```

<210> SEQ ID NO 7
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 7

```
cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt gca gcc tct gga ttc gcc ttc agt agc tat      96
Ser Leu Arg Leu Ser Cys Ala Ala Ser Gly Phe Ala Phe Ser Ser Tyr
            20                  25                  30 gct att cag tgg gtc cgc cag gct cca ggc aag ggg ctg gag tgg gtg     144
Ala Ile Gln Trp Val Arg Gln Ala Pro Gly Lys Gly Leu Glu Trp Val
        35                  40                  45 gca gtt ata tca tat gat gga agc aag aaa tac tat gca gac tcc gtg     192
Ala Val Ile Ser Tyr Asp Gly Ser Lys Lys Tyr Tyr Ala Asp Ser Val
 50                  55                  60 aag ggc cga ttc acc atc tcc aga gac aat tcc aag aat acg ctg tat     240
Lys Gly Arg Phe Thr Ile Ser Arg Asp Asn Ser Lys Asn Thr Leu Tyr
65                  70                  75                  80 ttg caa atg aac agc ctg aga gct gag gac acg gct gtg tat tac tgt     288
Leu Gln Met Asn Ser Leu Arg Ala Glu Asp Thr Ala Val Tyr Tyr Cys
                85                  90                  95 gcg aga gag ggg aga cgt ggg tcg ttt gac tac tgg ggc cag gga acc     336
Ala Arg Glu Gly Arg Arg Gly Ser Phe Asp Tyr Trp Gly Gln Gly Thr
            100                 105                 110 ctg gtc acc gtc tcc tca                                              354
Leu Val Thr Val Ser Ser
            115
```

<210> SEQ ID NO 8
<211> LENGTH: 118
<212> TYPE: PRT
<213> ORGANISM: Homo sapiens

<400> SEQUENCE: 8

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Ala Phe Ser Ser Tyr
             20                  25                  30

Ala Ile Gln Trp Val Arg Gln Ala Pro Gly Lys Gly Leu Glu Trp Val
         35                  40                  45

Ala Val Ile Ser Tyr Asp Gly Ser Lys Lys Tyr Tyr Ala Asp Ser Val
     50                  55                  60

Lys Gly Arg Phe Thr Ile Ser Arg Asp Asn Ser Lys Asn Thr Leu Tyr
 65              70                  75                  80

Leu Gln Met Asn Ser Leu Arg Ala Glu Asp Thr Ala Val Tyr Tyr Cys
             85                  90                  95

Ala Arg Glu Gly Arg Arg Gly Ser Phe Asp Tyr Trp Gly Gln Gly Thr
            100                 105                 110

Leu Val Thr Val Ser Ser
            115
```

<210> SEQ ID NO 9  
<211> LENGTH: 327  
<212> TYPE: DNA  
<213> ORGANISM: Homo sapiens  
<220> FEATURE:  
<221> NAME/KEY: CDS  
<222> LOCATION: (1)..(327)

<400> SEQUENCE: 9

```
gaa att gtg ttg acg cag tct cca ggc acc ctg tct ttg tct cca ggg       48
Glu Ile Val Leu Thr Gln Ser Pro Gly Thr Leu Ser Leu Ser Pro Gly
  1               5                  10                  15 gaa aga gcc acc ctc tcc tgc agg gcc agt cag agt gtt agc agc agc       96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agg ctc ctc      144
Tyr Leu Ala Trp Tyr Gln Gln Lys Pro Gly Gln Ala Pro Arg Leu Leu
         35                  40                  45 atc ttt ggt gca tcc agc agg gcc act ggc atc cca gac agg ttc agt      192
Ile Phe Gly Ala Ser Ser Arg Ala Thr Gly Ile Pro Asp Arg Phe Ser
     50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
 65              70                  75                  80 cct gaa gat ttt gca gtg tat tac tgt cag cag tat ggt agc tca cct      288
Pro Glu Asp Phe Ala Val Tyr Tyr Cys Gln Gln Tyr Gly Ser Ser Pro
             85                  90                  95 ccg tgg acg ttc ggc caa ggg acc aag gtg gaa atc aaa                  327
Pro Trp Thr Phe Gly Gln Gly Thr Lys Val Glu Ile Lys
            100                 105
```

<210> SEQ ID NO 10  
<211> LENGTH: 109  
<212> TYPE: PRT  
<213> ORGANISM: Homo sapiens

<400> SEQUENCE: 10

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45
```

```
Ile Phe Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Trp Thr Phe Gly Gln Gly Thr Lys Val Glu Ile Lys
            100                 105

<210> SEQ ID NO 11
<211> LENGTH: 345
<212> TYPE: DNA
<213> ORGANISM: Homo sapiens
<220> FEATURE:
<221> NAME/KEY: CDS
<222> LOCATION: (1)..(345)

<400> SEQUENCE: 11 gag gtt cag ctg gtg cag tct ggg gga ggc ttg gta cat cct ggg ggg      48
Glu Val Gln Leu Val Gln Ser Gly Gly Gly Leu Val His Pro Gly Gly
 1               5                  10                  15 tcc ctg aga ctc tcc tgt gca ggc tct gga ttc acc ttc agt aga aat      96
Ser Leu Arg Leu Ser Cys Ala Gly Ser Gly Phe Thr Phe Ser Arg Asn
             20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
         35                  40                  45 tca ggt att ggt act ggt ggt gcc aca aac tat gca gac tcc gtg aag     192
Ser Gly Ile Gly Thr Gly Gly Ala Thr Asn Tyr Ala Asp Ser Val Lys
     50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
 65                  70                  75                  80 caa atg aac agc ctg aga gcc gag gac atg gct gtg tat tac tgt gca     288
Gln Met Asn Ser Leu Arg Ala Glu Asp Met Ala Val Tyr Tyr Cys Ala
                 85                  90                  95 aga ggg agg tac tac ttt gac tac tgg ggc cag gga acc ctg gtc acc     336
Arg Gly Arg Tyr Tyr Phe Asp Tyr Trp Gly Gln Gly Thr Leu Val Thr
            100                 105                 110 gtc tcc tca                                                         345
Val Ser Ser
        115

<210> SEQ ID NO 12
<211> LENGTH: 115
<212> TYPE: PRT
<213> ORGANISM: Homo sapiens

<400> SEQUENCE: 12

Glu Val Gln Leu Val Gln Ser Gly Gly Gly Leu Val His Pro Gly Gly
 1               5                  10                  15

Ser Leu Arg Leu Ser Cys Ala Gly Ser Gly Phe Thr Phe Ser Arg Asn
             20                  25                  30

Ala Met Phe Trp Val Arg Gln Ala Pro Gly Lys Gly Leu Glu Trp Val
         35                  40                  45

Ser Gly Ile Gly Thr Gly Gly Ala Thr Asn Tyr Ala Asp Ser Val Lys
     50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Met Ala Val Tyr Tyr Cys Ala
```

```
                    85                  90                  95
Arg Gly Arg Tyr Tyr Phe Asp Tyr Trp Gly Gln Gly Thr Leu Val Thr
            100                 105                 110

Val Ser Ser
        115

<210> SEQ ID NO 13
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 13 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
            20                  25                  30 tac tta gcc tgg tac caa cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca cct     288
Pro Glu Asp Phe Ala Val Tyr Tyr Cys Gln Gln Tyr Gly Ser Ser Pro
                85                  90                  95 ccg tgg acg ttc ggc caa ggg acc aag gtg gaa atc aaa                 327
Pro Trp Thr Phe Gly Gln Gly Thr Lys Val Glu Ile Lys
            100                 105

<210> SEQ ID NO 14
<211> LENGTH: 109
<212> TYPE: PRT
<213> ORGANISM: Homo sapiens

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 15
<211> LENGTH: 348
<212> TYPE: DNA
```

<213> ORGANISM: Homo sapiens
<220> FEATURE:
<221> NAME/KEY: CDS
<222> LOCATION: (1)..(348)

<400> SEQUENCE: 15

```
cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt tca gcg tct gga ttc acc ttc agt aga tat      96
Ser Leu Arg Leu Ser Cys Ser Ala Ser Gly Phe Thr Phe Ser Arg Tyr
            20                  25                  30 ggc atg cac tgg gtc cgc cag gct cca ggc agg ggg ctg gag tgg gtg     144
Gly Met His Trp Val Arg Gln Ala Pro Gly Arg Gly Leu Glu Trp Val
        35                  40                  45 gca att ata tgg ttt gaa gga aat aat caa tac tat gca gac tcc gtg     192
Ala Ile Ile Trp Phe Glu Gly Asn Asn Gln Tyr Tyr Ala Asp Ser Val
    50                  55                  60 aag ggc cga ttc acc gtc tcc aga gac aat tcc aag aac acg ctg tat     240
Lys Gly Arg Phe Thr Val Ser Arg Asp Asn Ser Lys Asn Thr Leu Tyr
65                  70                  75                  80 ctg gaa atg aac agc ctg aga gcc gag gac acg gct gtg tat tac tgt     288
Leu Glu Met Asn Ser Leu Arg Ala Glu Asp Thr Ala Val Tyr Tyr Cys
                85                  90                  95 gcg aga ggg aag tac tac ttt gac tac tgg ggc cag gga acc ctg gtc     336
Ala Arg Gly Lys Tyr Tyr Phe Asp Tyr Trp Gly Gln Gly Thr Leu Val
            100                 105                 110 acc gtc tcc tca                                                     348
Thr Val Ser Ser
        115
```

<210> SEQ ID NO 16
<211> LENGTH: 116
<212> TYPE: PRT
<213> ORGANISM: Homo sapiens

<400> SEQUENCE: 16

```
Gln Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Arg Tyr
            20                  25                  30

Gly Met His Trp Val Arg Gln Ala Pro Gly Arg Gly Leu Glu Trp Val
        35                  40                  45

Ala Ile Ile Trp Phe Glu Gly Asn Asn Gln Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Gly Lys Tyr Tyr Phe Asp Tyr Trp Gly Gln Gly Thr Leu Val
            100                 105                 110

Thr Val Ser Ser
        115
```

<210> SEQ ID NO 17
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 17

| | | | | | | | | | | | | | | | | |
|---|---|---|---|---|---|---|---|---|---|---|---|---|---|---|---|---|
| gaa | att | gtg | ttg | aca | cag | tct | cca | gcc | acc | ctg | tct | ttg | tct | cca | ggg | 48 |
| Glu | Ile | Val | Leu | Thr | Gln | Ser | Pro | Ala | Thr | Leu | Ser | Leu | Ser | Pro | Gly | |
| 1 | | | | 5 | | | | | 10 | | | | | 15 | | |
| gaa | aga | gcc | acc | ctc | tcc | tgc | agg | gcc | agt | cag | agt | gtt | agc | agc | tac | 96 |
| Glu | Arg | Ala | Thr | Leu | Ser | Cys | Arg | Ala | Ser | Gln | Ser | Val | Ser | Ser | Tyr | |
| | | | 20 | | | | | 25 | | | | | 30 | | | |
| tta | gcc | tgg | tac | caa | cag | aaa | cct | ggc | cag | gct | ccc | agg | ctc | ctc | atc | 144 |
| Leu | Ala | Trp | Tyr | Gln | Gln | Lys | Pro | Gly | Gln | Ala | Pro | Arg | Leu | Leu | Ile | |
| | | 35 | | | | | 40 | | | | | 45 | | | | |
| tat | cat | gca | tcc | aac | agg | gcc | act | ggc | atc | cca | gcc | agg | ttc | agt | ggc | 192 |
| Tyr | His | Ala | Ser | Asn | Arg | Ala | Thr | Gly | Ile | Pro | Ala | Arg | Phe | Ser | Gly | |
| 50 | | | | | 55 | | | | | 60 | | | | | | |
| agt | ggg | tct | ggg | aca | gac | ttc | act | ctc | acc | atc | agc | agc | cta | gag | cct | 240 |
| Ser | Gly | Ser | Gly | Thr | Asp | Phe | Thr | Leu | Thr | Ile | Ser | Ser | Leu | Glu | Pro | |
| 65 | | | | 70 | | | | | 75 | | | | | 80 | | |
| gaa | gat | ttt | gca | gtt | tat | tac | tgt | cag | cag | cgt | agc | aac | tgg | cct | ctc | 288 |
| Glu | Asp | Phe | Ala | Val | Tyr | Tyr | Cys | Gln | Gln | Arg | Ser | Asn | Trp | Pro | Leu | |
| | | | 85 | | | | | 90 | | | | | 95 | | | |
| act | ttc | ggc | gga | ggg | acc | aag | gtg | gag | atc | aaa | | | | | | 321 |
| Thr | Phe | Gly | Gly | Gly | Thr | Lys | Val | Glu | Ile | Lys | | | | | | |
| | | 100 | | | | | 105 | | | | | | | | | |

<210> SEQ ID NO 18
<211> LENGTH: 107
<212> TYPE: PRT
<213> ORGANISM: Homo sapiens

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr His Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 19
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 19

| | | | | | | | | | | | | | | | | |
|---|---|---|---|---|---|---|---|---|---|---|---|---|---|---|---|---|
| gag | gtg | caa | ctg | gtg | cag | tct | ggg | gga | ggc | ttg | gta | cat | cct | ggg | ggg | 48 |
| Glu | Val | Gln | Leu | Val | Gln | Ser | Gly | Gly | Gly | Leu | Val | His | Pro | Gly | Gly | |
| 1 | | | | 5 | | | | | 10 | | | | | 15 | | |
| tcc | ctg | aga | ctc | acc | tgt | gca | ggc | tct | gga | ttc | acc | ttc | agt | aac | ttt | 96 |
| Ser | Leu | Arg | Leu | Thr | Cys | Ala | Gly | Ser | Gly | Phe | Thr | Phe | Ser | Asn | Phe | |
| | | | 20 | | | | | 25 | | | | | 30 | | | |
| gtt | atg | cac | tgg | gtt | cgc | cag | act | cca | gga | caa | ggt | ctg | gag | tgg | gtt | 144 |
| Val | Met | His | Trp | Val | Arg | Gln | Thr | Pro | Gly | Gln | Gly | Leu | Glu | Trp | Val | |

```
                         35                  40                  45
tca gct att ggt act ggt ggt ggc aca tac tat gca gac tcc gtg aag         192
Ser Ala Ile Gly Thr Gly Gly Gly Thr Tyr Tyr Ala Asp Ser Val Lys
 50                  55                  60 ggc cga ttc acc atc tcc aga gac aat gcc aag agc tcc tta tat ctt         240
Gly Arg Phe Thr Ile Ser Arg Asp Asn Ala Lys Ser Ser Leu Tyr Leu
 65                  70                  75                  80 caa atg aac agc ctg aga gcc gag gac atg gct gtg tat tac tgt gca         288
Gln Met Asn Ser Leu Arg Ala Glu Asp Met Ala Val Tyr Tyr Cys Ala
                 85                  90                  95 aga gat cgg cct atg gtt cgg gga gtc att ata gac tac ttt gac tac         336
Arg Asp Arg Pro Met Val Arg Gly Val Ile Ile Asp Tyr Phe Asp Tyr
            100                 105                 110 tgg ggc cag gga acc ctg gtc acc gtc tcc tca                             369
Trp Gly Gln Gly Thr Leu Val Thr Val Ser Ser
        115                 120

<210> SEQ ID NO 20
<211> LENGTH: 123
<212> TYPE: PRT
<213> ORGANISM: Homo sapiens

<400> SEQUENCE: 20

Glu Val Gln Leu Val Gln Ser Gly Gly Gly Leu Val His Pro Gly Gly
 1               5                  10                  15

Ser Leu Arg Leu Thr Cys Ala Gly Ser Gly Phe Thr Phe Ser Asn Phe
                20                  25                  30

Val Met His Trp Val Arg Gln Thr Pro Gly Gln Gly Leu Glu Trp Val
            35                  40                  45

Ser Ala Ile Gly Thr Gly Gly Gly Thr Tyr Tyr Ala Asp Ser Val Lys
 50                  55                  60

Gly Arg Phe Thr Ile Ser Arg Asp Asn Ala Lys Ser Ser Leu Tyr Leu
 65                  70                  75                  80

Gln Met Asn Ser Leu Arg Ala Glu Asp Met Ala Val Tyr Tyr Cys Ala
                 85                  90                  95

Arg Asp Arg Pro Met Val Arg Gly Val Ile Ile Asp Tyr Phe Asp Tyr
            100                 105                 110

Trp Gly Gln Gly Thr Leu Val Thr Val Ser Ser
        115                 120

<210> SEQ ID NO 21
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 21 gac atc cag atg acc cag tct cca tct tcc gtg tct gca tct gta gga         48
Asp Ile Gln Met Thr Gln Ser Pro Ser Ser Val Ser Ala Ser Val Gly
 1               5                  10                  15 gac aga gtc acc atc act tgt cgg gcg agt cag ggt att agc acc tgg         96
Asp Arg Val Thr Ile Thr Cys Arg Ala Ser Gln Gly Ile Ser Thr Trp
                20                  25                  30 tta gcc tgg tat cag cat aaa cca ggg aaa gcc cct aag ctc ctg atc        144
Leu Ala Trp Tyr Gln His Lys Pro Gly Lys Ala Pro Lys Leu Leu Ile
            35                  40                  45 tat gtt gca tcc agt ttg caa agt ggg gtc cca tca agg ttc agc ggc        192
Tyr Val Ala Ser Ser Leu Gln Ser Gly Val Pro Ser Arg Phe Ser Gly
 50                  55                  60
```

```
agt gga tct ggg aca gat ttc act ctc acc atc agc agc ctg cag cct    240
Ser Gly Ser Gly Thr Asp Phe Thr Leu Thr Ile Ser Ser Leu Gln Pro
 65              70                  75                  80 gaa gat ttt gca act tac tat tgt caa cag gct aat agt ttc cca ttc    288
Glu Asp Phe Ala Thr Tyr Tyr Cys Gln Gln Ala Asn Ser Phe Pro Phe
                 85                  90                  95 act ttc ggc cct ggg acc aaa gtg gat atc aaa                        321
Thr Phe Gly Pro Gly Thr Lys Val Asp Ile Lys
            100                 105
```

<210> SEQ ID NO 22
<211> LENGTH: 107
<212> TYPE: PRT
<213> ORGANISM: Homo sapiens

<400> SEQUENCE: 22

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Thr Trp
                20                  25                  30

Leu Ala Trp Tyr Gln His Lys Pro Gly Lys Ala Pro Lys Leu Leu Ile
            35                  40                  45

Tyr Val Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Ala Asn Ser Phe Pro Phe
                 85                  90                  95

Thr Phe Gly Pro Gly Thr Lys Val Asp Ile Lys
            100                 105
```

<210> SEQ ID NO 23
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 23

```
gag gtg cag gtg ttg gag tcg ggg gga aac ttg gta cag cct ggg ggg     48
Glu Val Gln Val Leu Glu Ser Gly Gly Asn Leu Val Gln Pro Gly Gly
 1               5                  10                  15 tcc ctg aga ctc tcc tgt gca gcc tct gga ttc acc ttt agc agc tat     96
Ser Leu Arg Leu Ser Cys Ala Ala Ser Gly Phe Thr Phe Ser Ser Tyr
                20                  25                  30 gcc atg agc tgg gtc cgc cag gct cca ggg aag ggg ctg gag tgg gtc    144
Ala Met Ser Trp Val Arg Gln Ala Pro Gly Lys Gly Leu Glu Trp Val
            35                  40                  45 tct tct att act ggt agt ggg ggt agc aca tac tac gca gac tcc gtg    192
Ser Ser Ile Thr Gly Ser Gly Gly Ser Thr Tyr Tyr Ala Asp Ser Val
         50                  55                  60 aag ggc cgg ttc acc atc tcc aga gac aat tcc aag aac acg ctg tat    240
Lys Gly Arg Phe Thr Ile Ser Arg Asp Asn Ser Lys Asn Thr Leu Tyr
 65              70                  75                  80 ctg caa atg aac agc ctg aga gcc gag gac acg gcc att ttt tac tgt    288
Leu Gln Met Asn Ser Leu Arg Ala Glu Asp Thr Ala Ile Phe Tyr Cys
                 85                  90                  95 gcg aaa gat aac cgg gga ttc ttt cac tat tgg ggc cag gga acc ctg    336
Ala Lys Asp Asn Arg Gly Phe Phe His Tyr Trp Gly Gln Gly Thr Leu
            100                 105                 110
```

```
gtc acc gtc tcc tca                                                   351
Val Thr Val Ser Ser
        115
```

<210> SEQ ID NO 24
<211> LENGTH: 117
<212> TYPE: PRT
<213> ORGANISM: Homo sapiens

<400> SEQUENCE: 24

```
Glu Val Gln Val Leu Glu Ser Gly Gly Asn Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Thr Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Phe Tyr Cys
                85                  90                  95

Ala Lys Asp Asn Arg Gly Phe Phe His Tyr Trp Gly Gln Gly Thr Leu
            100                 105                 110

Val Thr Val Ser Ser
        115
```

<210> SEQ ID NO 25
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 25

```
gaa att gtg ttg aca cag tct cca tct tcc gtg tct gca tct gta gga    48
Glu Ile Val Leu Thr Gln Ser Pro Ser Ser Val Ser Ala Ser Val Gly
1               5                   10                  15 gac aga gtc acc atc act tgt cgg gcg agt cag ggt att agc aat cgg    96
Asp Arg Val Thr Ile Thr Cys Arg Ala Ser Gln Gly Ile Ser Asn Arg
            20                  25                  30 tta gcc tgg tat cag cag aaa cca gga aaa gcc cct aaa ctc ctc atc   144
Leu Ala Trp Tyr Gln Gln Lys Pro Gly Lys Ala Pro Lys Leu Leu Ile
        35                  40                  45 tat att gca tcc att ttg caa agg ggg gtc cca tca aga ttc agc ggc   192
Tyr Ile Ala Ser Ile Leu Gln Arg Gly Val Pro Ser Arg Phe Ser Gly
50                  55                  60 agt gga tct ggg aca gat ttc act ctc acc atc acc agg ctg cag cct   240
Ser Gly Ser Gly Thr Asp Phe Thr Leu Thr Ile Thr Arg Leu Gln Pro
65                  70                  75                  80 gaa gat ttt gca acc tac tat tgt caa cag gca aac agt ttc cca ttc   288
Glu Asp Phe Ala Thr Tyr Tyr Cys Gln Gln Ala Asn Ser Phe Pro Phe
                85                  90                  95 act ttc ggc cct ggg acc aaa gtg gat atc aaa                       321
Thr Phe Gly Pro Gly Thr Lys Val Asp Ile Lys
            100                 105
```

<210> SEQ ID NO 26
<211> LENGTH: 107
<212> TYPE: PRT

```
<213> ORGANISM: Homo sapiens

<400> SEQUENCE: 26

Glu Ile Val Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Arg
            20                  25                  30

Leu Ala Trp Tyr Gln Gln Lys Pro Gly Lys Ala Pro Lys Leu Leu Ile
        35                  40                  45

Tyr Ile Ala Ser Ile Leu Gln Arg Gly Val Pro Ser Arg Phe Ser Gly
    50                  55                  60

Ser Gly Ser Gly Thr Asp Phe Thr Leu Thr Ile Thr Arg Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
                100                 105
```